US012678095B2

(12) United States Patent
Yu et al.

(10) Patent No.: US 12,678,095 B2
(45) Date of Patent: Jul. 14, 2026

(54) SYSTEMS, METHODS, AND COMPUTER READABLE MEDIA FOR BREATHING SIGNAL ANALYSIS AND EVENT DETECTION AND GENERATING RESPIRATORY FLOW AND EFFORT ESTIMATE SIGNALS

(71) Applicant: BRESOTEC INC., Toronto (CA)

(72) Inventors: Jinxin Yu, Toronto (CA); Richard George Hummel, Toronto (CA); Cristiano Santos De Aguiar, Toronto (CA); Wei Fan, Vaughan (CA); Devin Packer, Hamilton (CA)

( * ) Notice: Subject to any disclaimer, the term of this patent is extended or adjusted under 35 U.S.C. 154(b) by 0 days.

(21) Appl. No.: 18/400,137

(22) Filed: Dec. 29, 2023

(65) Prior Publication Data

US 2025/0387078 A1     Dec. 25, 2025

Related U.S. Application Data

(63) Continuation of application No. PCT/CA2022/051031, filed on Jun. 28, 2022.

(Continued)

(51) Int. Cl.
*A61B 5/00*     (2006.01)
*A61B 5/08*     (2006.01)
*A61B 5/145*    (2006.01)

(52) U.S. Cl.
CPC ........ *A61B 5/4818* (2013.01); *A61B 5/14542* (2013.01); *A61B 5/725* (2013.01);
(Continued)

(58) Field of Classification Search
CPC ..... A61B 5/4818; A61B 5/08; A61B 5/14542; A61B 5/725; A61B 5/7257; A61B 5/7278;
(Continued)

(56) References Cited

U.S. PATENT DOCUMENTS

2013/0245502 A1     9/2013   Lange et al.
2013/0289401 A1     10/2013  Colbaugh et al.
(Continued)

FOREIGN PATENT DOCUMENTS

CA     2888394 A1     11/2015
WO     2019122412 A1   6/2019
WO     2020132315 A1   6/2020

OTHER PUBLICATIONS

CIPO, "International Search Report and The Written Opinion," mailed Sep. 1, 2022, PCT Application No. PCT/CA2022/051031, 15 pages.

(Continued)

*Primary Examiner* — Robert L Nasser
(74) *Attorney, Agent, or Firm* — Dickinson Wright LLP; Yuri Chumak

(57)     ABSTRACT

Provided are systems, methods and computer-readable media for breathing signal analysis and event detection and systems, methods and computer-readable media for generating respiratory flow and/or effort signals from accelerometer signals using trained models. Breathing signal analysis may characterize at least one recorded signal as indicative of one of Obstructive Sleep Apnea (OSA) and Central Sleep Apnea (CSA). This analysis includes determining a frequency domain representation of an audio signal; sorting at least one frequency interval component into at least one corresponding frequency bin; determining a signal-to-noise ratio (SNR) signal for each frequency bin during a candidate time period; and determining an indication of an OSA event or a CSA event.

15 Claims, 36 Drawing Sheets

Related U.S. Application Data

(60) Provisional application No. 63/236,852, filed on Aug. 25, 2021, provisional application No. 63/216,385, filed on Jun. 29, 2021.

(52) U.S. Cl.
CPC .......... *A61B 5/7257* (2013.01); *A61B 5/7278* (2013.01); *A61B 2562/0204* (2013.01); *A61B 2562/0219* (2013.01)

(58) Field of Classification Search
CPC .......... A61B 5/7282; A61B 2562/0204; A61B 2562/0219
See application file for complete search history.

(56) References Cited

U.S. PATENT DOCUMENTS

| | | | |
|---|---|---|---|
| 2014/0128697 A1 | 5/2014 | Parfenova et al. | |
| 2018/0070890 A1 | 3/2018 | Bradley et al. | |
| 2020/0365271 A1 | 11/2020 | Huang et al. | |
| 2021/0077013 A1 | 3/2021 | Mistrorigo De Almeida | |

OTHER PUBLICATIONS

Cohen, I. and B. Berdugo, "Noise estimation by minima controlled recursive averaging for robust speech enhancement," in IEEE Signal Processing Letters, vol. 9, No. 1, pp. 12-15, Jan. 2002, doi: 10.1109/97.988717.

Hummel, R, T. D. Bradley, D. Packer and H. Alshaer, "Distinguishing obstructive from central sleep apneas and hypopneas using linear SVM and acoustic features," 2016, 38th Annual International Conference of the IEEE Engineering in Medicine and Biology Society (EMBC), 2016, pp. 2236-2240, doi: 10.1109/EMBC.2016.7591174.

Cohen, I "Noise spectrum estimation in adverse environments: improved minima controlled recursive averaging," in IEEE Transactions on Speech and Audio Processing, vol. 11, 110. 5, pp. 466-475, Sep. 2003, doi: 10.1109/TSA.2003.811544.

500

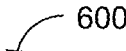

600

```
┌─────────────────────────────────────┐
│ Receiving, at a processor, an audio  │─── 602
│ signal and a corresponding           │
│ accelerometer signal                 │
└─────────────────────────────────────┘
                  │
┌─────────────────────────────────────┐
│ Determining, at the processor, a     │
│ frequency domain representation of   │─── 604
│ the audio signal                     │
└─────────────────────────────────────┘
                  │
┌─────────────────────────────────────┐
│ Sorting, at the processor, at least  │
│ one frequency interval component of  │
│ the frequency domain representation  │─── 606
│ of the audio signal into a           │
│ corresponding frequency bin in an    │
│ at least one frequency bin           │
└─────────────────────────────────────┘
                  │
┌─────────────────────────────────────┐
│ Determining, at the processor, a     │─── 608
│ signal-to-noise ratio signal for     │
│ each frequency bin in the at least   │
│ one frequency bin for a candidate    │
│ time period                          │
└─────────────────────────────────────┘
                  │
┌─────────────────────────────────────┐
│ Determining, using a machine         │─── 610
│ learning model at the processor, an  │
│ indication of an OSA event or a CSA  │
│ event based on the signal-to-noise   │
│ ratio signal for each frequency bin  │
│ of the candidate time periods, the   │
│ audio signal for the candidate time  │
│ period, and the accelerometer signal │
│ for the candidate time period        │
└─────────────────────────────────────┘
```

FIG. 6

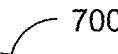
700

Receiving, at the processor, an audio
signal for a candidate time period, and a
corresponding accelerometer signal for the
candidate time period
— 702

Determining, at the processor, an input
sequence for a machine learning model
based on a signal-to-noise ratio signal for a
plurality of frequency bins of the audio
signal for the candidate time period, the
audio signal for the candidate time period,
and the accelerometer signal for the
candidate time period
—704

Determining, using the machine learning
model at the processor, an occurrence of
an OSA event or an CSA event based on
the signal-to-noise ratio signal for each
frequency bin of the candidate time
periods, the audio signal for the candidate
time period, and the accelerometer signal
for the candidate time period
—706

FIG. 7A

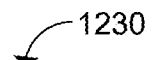
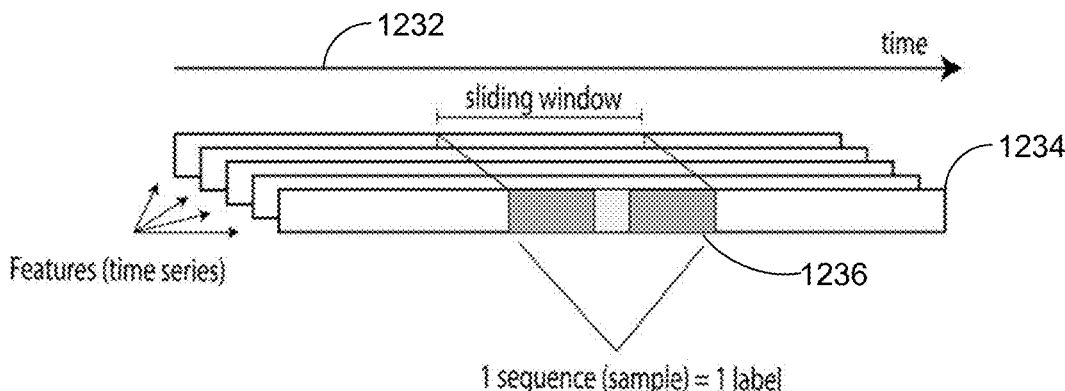
FIG. 12B

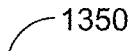
1350

Receiving, at a processor, training data comprising a plurality of audio signals and a plurality of accelerometer signals corresponding to the plurality of audio signals ⟋1352

Extracting, at the processor, a plurality of feature values from the training data, the plurality of feature values corresponding to a plurality of predetermined features ⟋1354

Training, at the processor, the at least one machine learning model for event detection of Obstructive Sleep Apnea (OSA) events and Central Sleep Apnea (CSA) events from recorded breath sounds based on the plurality of feature values ⟋1356

FIG. 13B

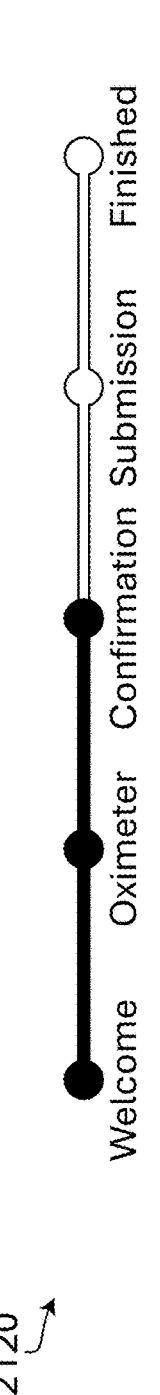
2120
Welcome   Oximeter   Confirmation   Submission   Finished
The following sensors will be linked:
OXIMETER
Not Connected
H/W ID
H/W Revision    V303
Serial          08:6B:D7:1F:CF:E0
S/W Revision    V303
PATCH
Not Connected   96.92%
H/W ID          0xfea667c6
H/W Revision    1.0.0
Serial
S/W Revision    V1.0.0-18-g609b645-dirty
ALL DATA ON THE DCU WILL BE ERASED. Continue?
▼ Previous
Prime ▲
2122
FIG. 21C 2130
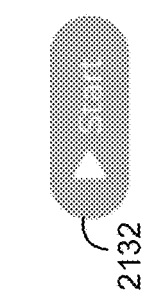
2132
Recording: Inactive
Idle
Accessories
URU Sensor
N/A
Other Accessories
N/A
Recording Session
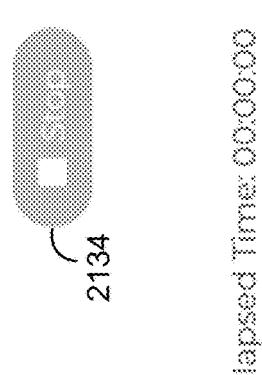
2134
Elapsed Time: 00:00:00
FIG. 21D

Upload Sleep Study

2140

Select recordings on this BresoHub to upload to BresoConnect for Processing

2142

| Start Date | Start Time | End Time | Duration |
|---|---|---|---|
| 2022-05-19 | 11:40:55 AM | 11:44:07 AM | 00:03:12 |

⬆ Upload    2144

| Sensor | Hardware ID | Serial Number | Software Version | Hardware Version |
|---|---|---|---|---|
| BresoSensor SN | fea667bf | 1234567890 | 1.4.0 | 1.0.0 |
| Nonin WristOX2 3150 | 3150 | 502799515 | 3.0.4 | 1.0.0 |

Previous    Next

Tests

My Tests  Shared with me

| Search 🔍 | Advanced ⌄ |

| Upload | Tracking No. | Device | Status | Shared | View/Edit |
|---|---|---|---|---|---|
| 2021/06/09 02:19:22 PM | 12341234 | Patch | ✓ Analysis Complete | 2 ❋ | ✎ |
| 2021/06/09 02:19:22 PM | 54415020 | Patch | ✓ Analysis Complete | 🔒 | ✎ |
| 2021/06/09 02:19:22 PM | 55707828 | BresoDX | ! Analysis Error | 🔒 | ✎ |

SYSTEMS, METHODS, AND COMPUTER READABLE MEDIA FOR BREATHING SIGNAL ANALYSIS AND EVENT DETECTION AND GENERATING RESPIRATORY FLOW AND EFFORT ESTIMATE SIGNALS

CROSS REFERENCE TO PRIOR APPLICATIONS

This application is a continuation of PCT application no. PCT/CA2022/051031, filed Jun. 28, 2022, and titled "SYSTEMS, METHODS, AND COMPUTER READABLE MEDIA FOR BREATHING SIGNAL ANALYSIS AND EVENT DETECTION AND GENERATING RESPIRATORY FLOW AND EFFORT ESTIMATE SIGNALS", which claims priority to U.S. provisional patent application no. 63/216,385, filed Jun. 29, 2021, and titled "SYSTEMS, METHODS, AND COMPUTER READABLE MEDIA FOR BREATHING SIGNAL ANALYSIS AND EVENT DETECTION" and U.S. provisional patent application No. 63/236,852, filed Aug. 25, 2021, and titled "METHOD AND SYSTEM FOR GENERATING RESPIRATORY FLOW AND EFFORT ESTIMATE SIGNALS", the contents of which are incorporated herein by reference in their entirety.

FIELD

The described embodiments relate to the detection of breathing disorders and in particular to systems, methods, and computer-readable media for breathing disorder identification, prediction, characterization and diagnosis.

BACKGROUND

Sleep apnea (SA) is a breathing disorder characterized by repetitive complete or partial cessations of breathing (apneas and hypopneas, respectively) during sleep. The frequency of these events ranges from 5 to 100 times/hour depending on the severity of the case. As a result, patients suffer from poor sleep quality, daytime sleepiness, and poor cognitive performance. Sleep apnea can generally be characterized as one of two types Obstructive and Central sleep apnea (OSA and CSA, respectively). It has been observed that OSA, which is the most common type, increases the risk of developing hypertension, heart failure (HF), and stroke by 3 to 4 fold. Also, patients with untreated sleep apnea generally consume twice as many healthcare resources for treatment of cardio-respiratory diseases than subjects without the disease. On the other hand, it has been demonstrated that treating OSA in patients with hypertension or HF lowers blood pressure, and dramatically improves cardiovascular function. Therefore, diagnosing and treating such patients could have a very substantial beneficial medical and public health impact.

Most people with sleep apnea remain undiagnosed due to the lack of accessibility to expensive overnight monitoring in a sleep laboratory presently required for diagnosis. Testing can occur at home but requires the uncomfortable use of a mask or other on-face device to be worn by a subject.

Obstructive sleep apnea (OSA) is generally understood to result from partial or complete collapse of the pharynx or the upper airway (UA) resulting in obstruction of the airflow pathway. In OSA, the respiratory drive is still present, but the patient is breathing against a high resistance tube—a situation that mimics choking. Thus, the hallmark of OSA is narrowing, obstruction, or total closure of the upper airway (pharynx). This results in characteristic breath sounds such as the occurrence of snoring and turbulent sounds. Each event generally lasts 10 to 60 seconds, thus generally causing episodes of oxygen deprivation and often provoking arousals from sleep and consequent sleep fragmentation. As a result, patients suffer from poor sleep quality, daytime sleepiness, and impaired cognitive performance, it is a common disease affecting approximately 7% of adults. Nevertheless, most patients with OSA remain undiagnosed; in one study, it was shown that 93% of women and 82% of men with moderate to severe OSA had not been diagnosed.

Central sleep apnea (CSA) on the other hand, is generally understood to occur when there is a temporary cessation of respiratory output from the respiratory neurons in the brainstem to the muscles of respiration. This lack of respiratory muscle activation causes a temporary cessation of airflow (i.e., central apnea), during which there is no respiratory ventilation. In contrast to OSA, the upper airway is usually open during CSA, and thus choking sounds and snoring are less likely to occur. Further, when airflow resumes, snoring does not necessarily occur because the pharynx is usually not obstructed.

The distinction between CSA and OSA can be of particular importance in choosing the management of the sleep apnea and associated diseases. This is especially important in patients with heart failure (HF) or stroke in whom CSA is common and is associated with increased mortality risk. Patients with HF have a very high prevalence of both OSA and CSA. The distinction is important for choosing the appropriate therapy. For example, in OSA, therapy usually consists of Continuous Positive Airway Pressure (CPAP), whereas in CSA the treatment strategy is generally to first treat the underlying HF, and if CSA persists, to use adaptive servo ventilation, oxygen or CPAP. It has also been shown that suppression of CSA by CPAP in patients improves the cardiovascular function and tends to improve survival.

Presently, the standard means of identifying and diagnosing sleep apnea is via overnight polysomnography (PSG), in which the patients must sleep in a laboratory attached to many monitoring electrodes under the supervision of a technician. PSG is expensive and access to it is limited, resulting in long waiting lists in the limited areas where PSG is available.

For this reason, interest has been raised in devising new methods to diagnose sleeping disorders, such as SA. For example, acoustic analysis of respiratory sounds has gained an increasing role in the study of respiratory disorders such as in identifying pathological respiratory sounds. In some sleep studies, snoring sounds were captured above the mouth level, as were tracheal sounds, to study snoring, particularly as snoring is a component of the disease itself and is produced at the very location where narrowing and obstruction takes place.

Despite recent findings, snore-driven techniques have fundamental limitations from the clinical perspective. For instance, snoring does not necessarily occur in all types of SA, such as in CSA. Furthermore, snore-driven techniques generally fail to assess the severity of an identified condition. For example, while snoring is a hallmark of OSA, it might not necessarily take place with each apnea and hypopnea. Accordingly, assessing the disease severity in terms of frequency of apneas per hour might be underestimated if some apneas are missed due to absence of snoring, for example. As knowledge about the disease severity can be beneficial in selecting an appropriate treatment strategy, snore-driven techniques can be less than ideal.

Accordingly, while some work has been done to detect the occurrence of OSA from snoring sounds, there remains much room for improvement. Demand is also increasing for reliable sleep apnea identification, characterization and/or diagnostic techniques that can be accessed by a wider base of the population for example, as compared to the technician-assisted PSG techniques currently implemented in dedicated sleep laboratories.

There remains therefore a need for new breathing disorder identification, characterization and diagnosis methods, devices and systems that overcome at least some of the drawbacks of known techniques, or at least, provides the public with a useful alternative.

SUMMARY

In a first aspect, some embodiments of the invention provide a computer-implemented method for breathing signal analysis for characterizing at least one recorded signal as indicative of one of Obstructive Sleep Apnea (OSA) and Central Sleep Apnea (CSA), the method comprising: receiving, at a processor, an audio signal and a corresponding accelerometer signal; determining, at the processor, a frequency domain representation of the audio signal; sorting, at the processor, at least one frequency interval component of the frequency domain representation of the audio signal into at least one corresponding frequency bin; determining, at the processor, a signal-to-noise ratio (SNR) signal for each frequency bin during a candidate time period; and determining, using a machine learning model at the processor, an indication of an OSA event or a CSA event based on the SNR signal for each frequency bin during the candidate time period, the audio signal for the candidate time period, and the accelerometer signal for the candidate time period.

In one or more embodiments, the method further comprises: determining a local minima for each frequency bin during the candidate time period; and wherein the determining the SNR signal for each frequency bin may comprise performing a minima controlled recursive averaging of the local minima for each frequency bin with a corresponding local minima for each frequency bin in at least one preceding time period.

In one or more embodiments, the minima controlled recursive averaging may comprise Cohen's method.

In one or more embodiments, the method may further comprise sampling the audio signal and the accelerometer signal based on a sliding window, and wherein the candidate time period may comprise the sliding window and the indication of the OSA event or CSA event may be determined for each of a plurality of time periods.

In one or more embodiments, the sliding window may be 61 seconds long.

In one or more embodiments, the method may further comprise applying, at the processor, a band-pass filter to the audio signal, the band-pass filter allowing frequencies between 200 Hz and 4000 Hz.

In one or more embodiments, the method may further comprise: outputting, at a user interface device in communication with the processor, the indication of the OSA event or the CSA event.

In one or more embodiments, the method may further comprise: determining, at the processor, a Hilbert envelope of the accelerometer signal; normalizing, at the processor, the accelerometer signal using the Hilbert envelope; and wherein the determining, using the machine learning model at the processor, the indication of the OSA event or the CSA event may be further based upon the normalized accelerometer signal.

In one or more embodiments, the method may further comprise: determining, at the processor, a spectral peak of the accelerometer signal; generating, at the processor, a breathing signal based on a frequency and a phase of the spectral peak; and wherein the determining, using the machine learning model at the processor, the indication of the OSA event or the CSA event is further based upon the breathing signal.

In one or more embodiments, the breathing signal may comprise a sinusoidal breathing signal model.

In one or more embodiments, the determining, using the machine learning model at the processor, the indication of the OSA event or the CSA event may further comprise: determining, at the processor, a plurality of sleep feature values based on the audio signal and the accelerometer signal, the plurality of sleep feature values corresponding to a plurality of sleep features; and wherein the plurality of sleep features may comprise at least one selected from the group of one or more audio features, and one or more accelerometer features.

In one or more embodiments, the one or more audio feature may comprise an audio signal-to-noise ratio signal statistic and an audio signal MFC coefficient.

In one or more embodiments, the one or more accelerometer features may comprise an accelerometer signal absolute rotation angle and pitch angle, and an accelerometer signal statistic.

In one or more embodiments, the method may further comprise receiving, at the processor, an oximeter signal; and wherein the plurality of sleep features may comprise at least one oximeter feature, and the at least one oximeter feature may comprise an oximeter signal drop and an oximeter signal slope.

In one or more embodiment, the determining the signal-to-noise ratio (SNR) signal for each frequency bin may further comprise: determining a total signal energy; determining a total noise energy; and determining the SNR based on a log of the ratio of the total signal energy to the total noise ratio.

In a second aspect, there is provided a breathing signal analysis system for characterizing at least one recorded signal as indicative of one of Obstructive Sleep Apnea (OSA) and Central Sleep Apnea (CSA) wherein the system is configured for performing the methods described herein.

In a third aspect, there is provided a non-transitory computer-readable medium with instructions stored thereon for breathing signal analysis for characterizing recorded breath sounds as indicative of one of Obstructive Sleep Apnea (OSA) and Central Sleep Apnea (CSA), that when executed by a processor, performs the methods described herein.

In a fourth aspect, there is provided a computer-implemented method for event detection of Obstructive Sleep Apnea (OSA) events and Central Sleep Apnea (CSA) events from recorded breath sounds of a subject, the method comprising: receiving, at the processor, an audio signal for a candidate time period, and a corresponding accelerometer signal for the candidate time period; determining, at the processor, an input sequence for a machine learning model based on a signal-to-noise ratio signal for a plurality of frequency bins of the audio signal for the candidate time period, the audio signal for the candidate time period, and the accelerometer signal for the candidate time period; and determining, using the machine learning model at the processor, an occurrence of an OSA event or a CSA event based on the signal-to-noise ratio signal for each frequency bin of the candidate time periods, the audio signal for the candidate time period, and the accelerometer signal for the candidate time period.

In one or more embodiments, the machine learning model may comprise: at least one neural network; at least one recurrent neural network; at least one dense layer; wherein the at least one neural network and the at least one recurrent neural network may receive the input sequence; wherein the at least one dense layer may receive a concatenated output of the at least one neural network and the at least one recurrent neural network; and wherein the occurrence of an OSA event or a CSA event may be determined based on the output of the at least one dense layer.

In one or more embodiments, the at least one neural network may comprise at least one convolutional neural network.

In one or more embodiments, the at least one recurrent neural network may comprise at least one long short-term memory (LSTM).

In one or more embodiments, the method may further comprise: outputting, at an output device in communication with the processor, the occurrence of the OSA event or the CSA event.

In one or more embodiments, the method may further comprise: receiving, at the processor, an oximetry signal for the candidate time period; and wherein the input sequence for the machine learning model may be further based upon the oximetry signal for the candidate time period.

In one or more embodiments, the method may further comprise: determining, at the processor, a sleep state of the subject, the sleep state determined using the audio signal and the accelerometer signal based on a statistical sleep model; and wherein the occurrence of an OSA event or a CSA event may be determined based on the sleep state of the subject.

In a fifth aspect, there is provided a system for event detection of Obstructive Sleep Apnea (OSA) events and Central Sleep Apnea (CSA) events from recorded breath sounds of a subject wherein the system is configured for performing the methods described herein.

In a sixth aspect, there is provided a non-transitory computer-readable medium with instructions stored thereon for event detection of Obstructive Sleep Apnea (OSA) events and Central Sleep Apnea (CSA) events from recorded breath sounds of a subject, that when executed by a processor, performs the methods herein.

In a seventh aspect, there is provided a computer-implemented method for training at least one machine learning model for event detection of Obstructive Sleep Apnea (OSA) events and Central Sleep Apnea (CSA) events from recorded breath sounds of a subject, the method comprising: receiving, at a processor, training data comprising a plurality of audio signals and a plurality of accelerometer signals corresponding to the plurality of audio signals; extracting, at the processor, a plurality of feature values from the training data, the plurality of feature values corresponding to a plurality of predetermined features; training, at the processor, the at least one machine learning model for event detection of Obstructive Sleep Apnea (OSA) events and Central Sleep Apnea (CSA) events from recorded breath sounds based on the plurality of feature values.

In one or more embodiments, the method may further comprise: wherein the at least one machine learning model may comprise: at least one neural network; at least one recurrent neural network; and at least one dense layer, and wherein the training the machine learning model further comprises: training, at the processor, the at least one neural network based on the plurality of feature values; training, at the processor, the at least one recurrent neural network based on the plurality of feature values; and training, at the processor, the at least one dense layer based on the plurality of feature values.

In one or more embodiments, the method may further comprise: processing, at the processor, the plurality of feature values corresponding to the plurality of predetermined features, the processing comprising at least one selected from the group of normalization, removal of one or more outlier values, and data interpolation.

In one or more embodiments, the training data may further comprise a plurality of oximetry signals.

In one or more embodiments, the training data may further comprise a plurality of signal-to-noise ratio signals for a corresponding plurality of frequency bins for each audio signal in the plurality of audio signals in the training data.

In one or more embodiments, the training data may further comprise a plurality of breathing signals corresponding to the plurality of accelerometer signals.

In one or more embodiments, the method may further comprise: wherein the at least one machine learning model further may comprise a statistical sleep model for predicting a sleep state of a subject; determining, at the processor, a plurality of sleep feature values corresponding to a plurality of sleep features; and training, at the processor, the statistical sleep model based on the plurality of sleep feature values.

In one or more embodiments, the plurality of sleep features may comprise at least one selected from the group of one or more audio features, one or more accelerometer features, and optionally one or more oximetry features.

In one or more embodiments, the plurality of sleep features may comprise at least one selected from the group of an audio signal-to-noise ratio signal statistic, an audio signal MFC (mel-frequency cepstrum) coefficient, an accelerometer signal absolute rotation angle and pitch angle, and an accelerometer signal statistic.

In an eighth aspect, there is provided a system for training a breathing event detection model for event detection of Obstructive Sleep Apnea (OSA) events and Central Sleep Apnea (CSA) events from recorded breath sounds of a subject wherein the system is configured for performing the methods herein.

In a ninth aspect, there is provided a non-transitory computer-readable medium with instructions stored thereon for training a breathing event detection model for event detection of Obstructive Sleep Apnea (OSA) events and Central Sleep Apnea (CSA) events from recorded breath sounds of a subject, that when executed by a processor, performs the methods herein.

In a tenth aspect, there is provided a computer-implemented method for generating acceleration-based respiratory effort predictions, the method comprising: receiving, at a processor, at least one accelerometer signal and a corresponding polysomnography (PSG)-based signal; aligning, by the processor, the at least one accelerometer signal with the PSG-based signal in a time domain to generate at least one aligned accelerometer signal; training a respiratory effort estimation model using the at least one aligned accelerometer signal and the PSG-based signal; and generating a trained respiratory effort estimation model.

In one or more embodiments, the PSG-based signal is a RIP sum signal.

In one or more embodiments, the method further comprising, prior to aligning, pre-processing the at least one accelerometer signal and the PSG-based signal.

In one or more embodiments, the pre-processing a signal comprises: applying one or more filters to the signal to generate a filtered signal; down-sampling the filtered signal to generate a down-sampled signal; applying a change-point detection method to the down-sampled signal to determine one or more shift points; segmenting the signal into one or more segments around the one or more determined shift points; and normalizing each of the one or more segments to generate a normalized signal.

In one or more embodiments, the one or more filters comprise a bandpass filter having a bandpass of 0.2 Hz to 5 Hz.

In one or more embodiments, the signal has a sampling frequency of 100 Hz, and down-sampling the signal comprises down-sampling the signal to 10 Hz.

In some cases, the change-point detection method comprises a pruned exact linear time (PELT) method.

In one or more embodiments, the method further comprises, after normalizing, applying a smoothing filter to the signal.

In one or more embodiments, the smoothing filter comprises a Savitzky-Golay filter.

In one or more embodiments, the aligning comprises: applying a cross-correlation method between the at least one accelerometer signal and the PSG-based signal; determining a time offset between the at least one accelerometer signal and the PSG-based signal that maximizes the cross-correlation; and applying the time offset to each of the at least one accelerometer signal.

In one or more embodiments, applying the cross-correlation method comprises: applying a plurality of time increment shifts to the at least one accelerometer signal within a pre-determined time range; for each of the plurality of time increment shifts, determining a cross-correlation value; identifying the time increment shift, of the plurality of time increment shifts, having a maximum cross-correlation value; and determining the time offset as the identified time increment shift.

In one or more embodiments, the pre-determined time range is ±5 seconds.

In one or more embodiments, the at least one accelerometer signal comprises an x-channel accelerometer signal and a z-channel accelerometer signal, wherein the x-channel is defined along a transverse axis and the z-channel is defined along a frontal axis.

In one or more embodiments, applying the cross-correlation method comprises: determining a cross-correlation value between one of the x-channel and z-channel accelerometer signals and the PSG-based signal; and applying the time offset comprises applying the time offset to each of the x-channel and z-channel accelerometer signals.

In one or more embodiments, the model is a linear regression model.

In one or more embodiments, training the model comprises using one or more of ridge regression and lasso regression.

In one or more embodiments, receiving the at least one accelerometer signal comprises receiving the at least one accelerometer signal from an accelerometer located within a patch sensor device mounted around a subject's suprasternal notch.

In one or more embodiments, the method further comprises: receiving at least one new accelerometer signal; inputting the at least one new accelerometer signal into the trained model to output an acceleration-based effort estimation.

In an eleventh aspect, there is provided a system for generating acceleration-based respiratory effort predictions, wherein the system comprises one or more processor configured to perform the method of generating acceleration-based respiratory effort predictions.

In a twelfth aspect, there is provided a non-transitory computer-readable medium with instructions stored thereon for generating acceleration-based respiratory effort predictions, that when executed by one or more processors, perform the method of generating acceleration-based respiratory effort predictions.

In a thirteenth aspect, there is provided a computer-implemented method for generating acceleration-based respiratory flow predictions, the method comprising: receiving, at a processor, at least one accelerometer signal and a corresponding polysomnography (PSG)-based signal; aligning, by the processor, the at least one accelerometer signal with the PSG-based signal in a time domain to generate at least one aligned accelerometer signal; training a respiratory flow estimation model using the at least one new accelerometer signal and the PSG-based signal; and generating a trained respiratory effort estimation model.

In one or more embodiments, the PSG-based signal comprises nasal pressure data.

In one or more embodiments, the method comprises: receiving at least one new accelerometer signal; inputting the at least one new accelerometer signal into the trained model to output an acceleration-based flow estimation.

In one or more embodiments, the method further comprises: receiving tracheal sound data recorded concurrently with the at least one new accelerometer signal; processing the tracheal sound data to generate an audio-based modulator signal; and modulating the acceleration-based flow estimation with the audio-based modulator signal to generate an output modulated flow estimation.

In one or more embodiments, processing the tracheal sound data to generate the audio-based modulator signal comprises: applying a bandpass filter to the sound data to generate filtered sound data; deriving an audio magnitude signal from the filtered sound data; extracting an envelope signal from the audio magnitude signal; and applying log scale-based normalization to the envelope signal.

In one or more embodiments, the method further comprises: applying a gating to a log scaled-based normalized signal to generate the audio-based modulator signal.

In one or more embodiments, the method further comprises, prior to the modulating, processing the acceleration-based flow estimation to exclude from modulation pre-defined window segments corresponding to regular steady sleep.

In one or more embodiments, the method further comprises segmenting the acceleration-based flow estimation into one or more window segments, and for each window segment: determining a spectral density of the window segment; determining from the spectral density a ratio of 1/7.5 Hz to ½ Hz components; and determining if the ratio is greater than a pre-determined threshold, wherein if the ratio is greater than the pre-determined threshold, excluding the window segment from modulation.

In one or more embodiments, the method further comprises segmenting the acceleration-based flow estimation into one or more window segments, and for each window segment: determining a flatness-based metric; and determining if the metric is greater than a pre-determined threshold, wherein if the metric is greater than the pre-determined threshold, excluding the window segment from modulation.

In one or more embodiments, the method further comprises excluding a window segment if the ratio and the flatness-based metric are each greater than their respective pre-determined threshold.

In a fourteenth aspect, there is provide a system for generating acceleration-based respiratory flow predictions, wherein the system comprises one or more processor configured to perform the method for generating acceleration-based respiratory flow predictions.

In a fifteenth aspect, there is provided a non-transitory computer-readable medium with instructions stored thereon for generating acceleration-based respiratory flow predictions, that when executed by one or more processors, perform the method for generating acceleration-based respiratory flow predictions.

BRIEF DESCRIPTION OF THE DRAWINGS

A preferred embodiment of the present invention will now be described in detail with reference to the drawings, in which:

FIG. 6 shows an example breathing signal analysis method in accordance with one or more embodiments.

FIG. 7A shows an example breathing event detection method in accordance with one or more embodiments.

FIG. 12B shows a sliding window sampling technique of FIG. 12A in accordance with one or more embodiments.

FIG. 13B shows another example event detection model training method in accordance with one or more embodiments.

FIG. 21C shows another example user interface for hub device and patch device setup in accordance with one or more embodiments.

FIG. 21D shows an example user interface for subject sleep session recording control in accordance with one or more embodiments.

FIG. 21E shows an example user interface for uploading sleep session recording data in accordance with one or more embodiments.

FIG. 21F shows an example clinician interface in accordance with one or more embodiments.

DESCRIPTION OF EXEMPLARY EMBODIMENTS

Figures 1A, 1B, 1C, 1D:
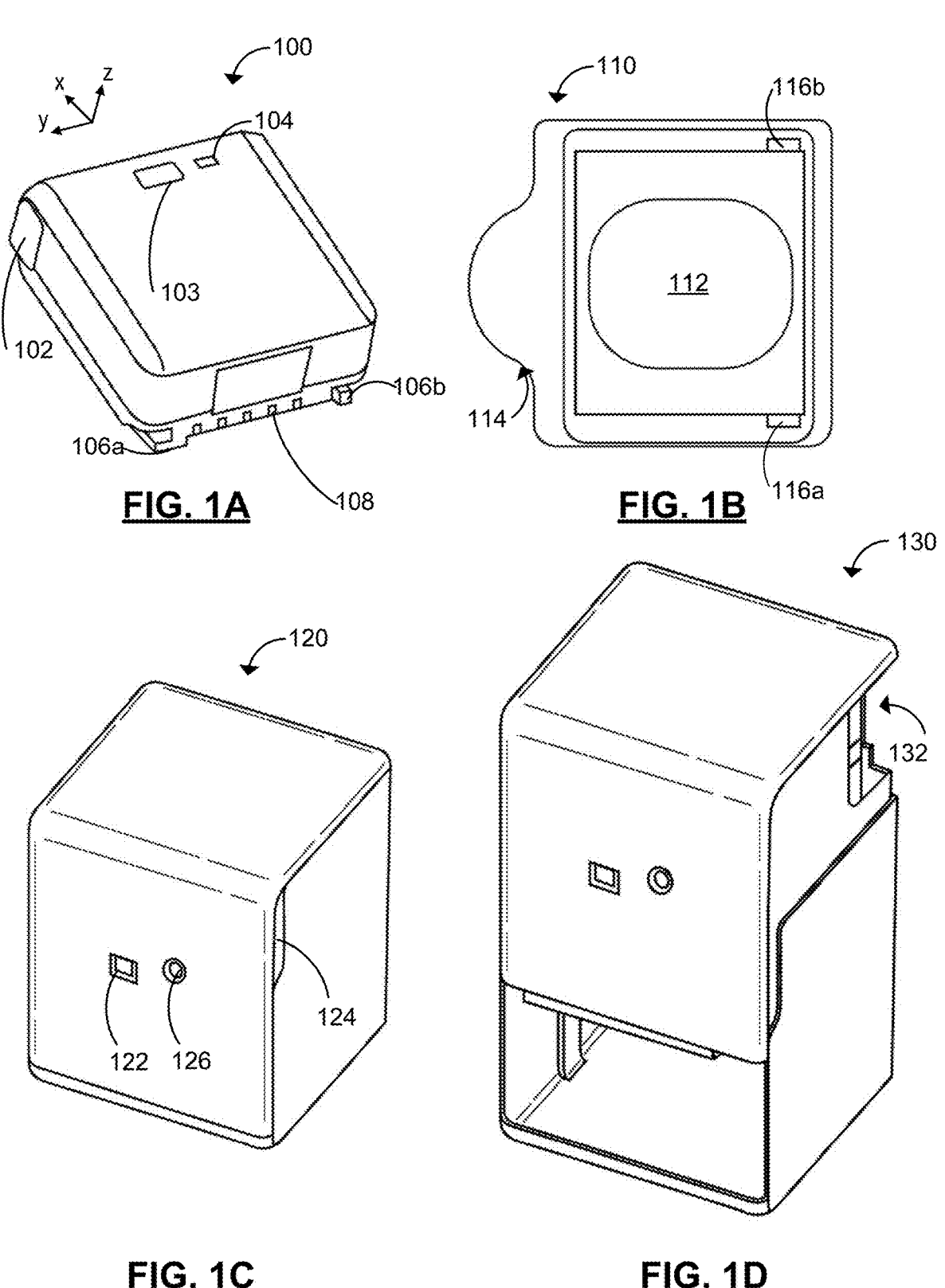
FIG. 1A shows an example patch sensor device in accordance with one or more embodiments.
FIG. 1B shows an example placement device for the patch sensor device in accordance with one or more embodiments.
FIG. 1C shows an example hub device in accordance with one or more embodiments.
FIG. 1D shows an example hub device in an open position for docking the patch device in accordance with one or more embodiments.

It will be appreciated that numerous specific details are set forth to provide a thorough understanding of the example embodiments described herein. However, it will be understood by those of ordinary skill in the art that the embodiments described herein may be practiced without these specific details. In other instances, well-known methods, procedures, and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

The embodiments of the systems and methods described herein may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication interface. For example, and without limitation, the programmable computers (referred to below as computing devices) may be a server, network appliance, embedded device, computer expansion module, personal computer, laptop, personal data assistant, cellular telephone, smart-phone device, tablet computer, wireless device or any other computing device capable of being configured to carry out the methods described herein.

In some embodiments, the communication interface may be a network communication interface. In embodiments in which elements are combined, the communication interface may be a software communication interface, such as those for inter-process communication (IPC). In still other embodiments, there may be a combination of communication interfaces implemented such as hardware, software, and combinations thereof.

Program code may be applied to input data to perform the functions described herein and to generate output information. The output information is applied to one or more output devices, in known fashion.

Each program may be implemented in a high-level procedural or object-oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g., ROM, magnetic disk, optical disc) readable by a general or special purpose programmable computer, for configuring and operating the computer when the storage media or device is read by the computer to perform the procedures described herein. Embodiments of the system may also be implemented as a non-transitory computer-readable storage medium, configured with a computer program, where the storage medium so configured causes a computer to operate in a specific and predefined manner to perform the functions described herein.

Furthermore, the systems, processes and methods of the described embodiments are capable of being distributed in a computer program product comprising a computer readable medium that bears computer usable instructions for one or more processors. The medium may be provided in various forms, including one or more diskettes, compact disks, tapes, chips, wireline transmissions, satellite transmissions, internet transmissions or downloads, magnetic and electronic storage media, digital and analog signals, and the like. The computer useable instructions may also be in various forms, including compiled and non-compiled code.

i. General System Architecture

Reference is first made to FIG. 1A, which shows an example patch device 100 in accordance with one or more embodiments. The patch device 100 may have an locking button 102, an activation button 103, an activation display means 104, a placement device attachment means 106, and a data connector 108.

Figures 3, 4:
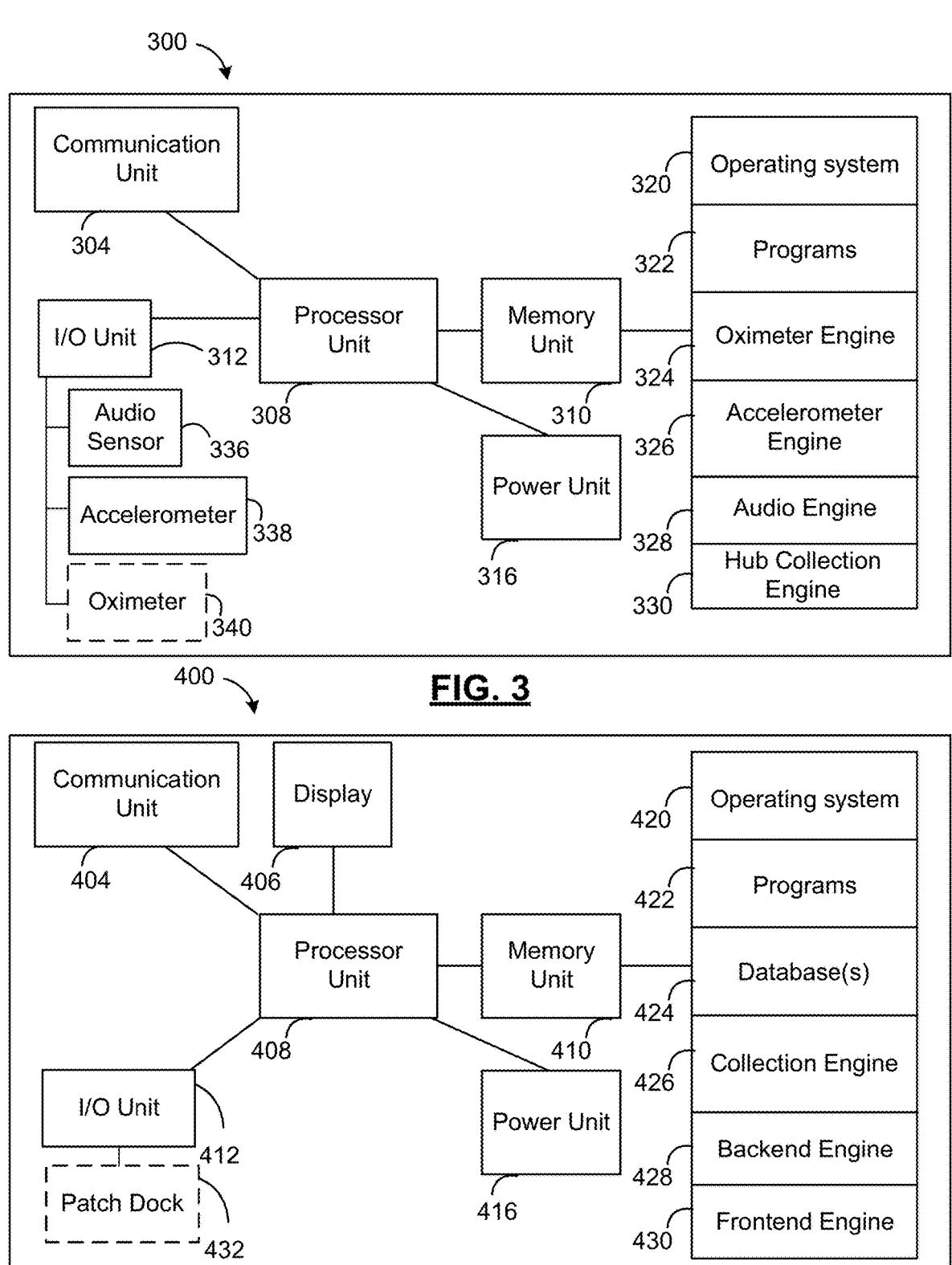
FIG. 3 shows an example patch device for breathing signal analysis and breathing event detection in accordance with one or more embodiments.
FIG. 4 shows an example hub device for breathing signal analysis and breathing event detection in accordance with one or more embodiments.

The patch device 100 may be the patch device described in FIG. 3, and elsewhere herein. The patch device 100 may be activated for recording using the activation button 103, and when activated, may display an indication to the subject that it is recording using activation display means 104. The activation display means 104 may be a light-emitting diode, or another display means as known. When activated, the patch device 100 may record sensor data using one or more sensor devices as described herein. The sensor devices may include one or more microphones, one or more accelerometers, and optionally one or more oximeter devices. In an alternate embodiment, the oximeter may be a separate device such as the one shown in FIG. 1E.

In use, the subject may attach a placement device such as the one shown in FIG. 1B on their skin and may connect the patch device to the placement device using the placement device attachment means 106. The placement device attachment means 106 may be tabs, as shown, that may fit inside complementary grooves on the placement device to affix the patch device to the subject. The placement device attachment means 106 may be another fastener, such as hook and loop tape, adhesive, magnets, etc. The patch device may be detached from the placement device using locking button 102.

The patch device 100 may dock with a hub device, and when docked, may communicate with the hub device using data connector 108. The patch device 100 may also communicate wirelessly with the hub device.

Referring next to FIG. 1B there is shown an example placement device 110 for the patch sensor device in accordance with one or more embodiments. The placement device 110 may have adhesive film 114 with a removeable backing for attachment to the subject's skin. The placement device 110 may be disposable and may be replaced after each use. The placement device 110 may have a sensor aperture 112 which may position the sensors of the patch device near the subject's skin exposed beneath. The placement device 110 may have placement device attachment means 116a and 116b for attachment of the patch device.

The placement device 110 may be shaped as shown or may be shaped to fit in the suprasternal notch of a subject.

In use, the subject may clean their skin with a swab, may remove the backing of the placement device 110, and then may place the placement device 110 on their skin with the tab pointed towards the stomach, so half the frame is above the upper edge of the manubrium, and half is below. The subject may then place the patch device inside the placement device 110 using the attachment means 116a and 116b and the complementary placement tabs on the patch device.

Referring next to FIGS. 1C and 1D together, there is shown a closed position of an example hub device 120, and a docking position of the hub device 120 in accordance with one or more embodiments. The hub device 120 may have a data connector 122 which may be used by a clinician user to download collected subject data from the hub device 120. The clinician user may also access a web server of the hub device 120 wirelessly and may initiate a data transfer from the hub device 120 of the collected sensor data. The hub device 120 may have a power connector 126 for providing power, and a docking button 124 for expanding the hub device 120 into a docking position as shown in FIG. 1D. The subject or clinician may push the docking button 124 and lift a first portion of the hub device 120 and put it into a docking position 130 to expose a docking port 132. The docking port 132 may accept the patch device (such as shown in FIG. 1A) and may charge the battery of the patch device and/or transfer collected sensor data from the patch device.

The hub device 120 may be given by a clinician to a subject for sleep monitoring and may be connected to power and placed in a locale proximate to the subject's bed.

Figure 1E:
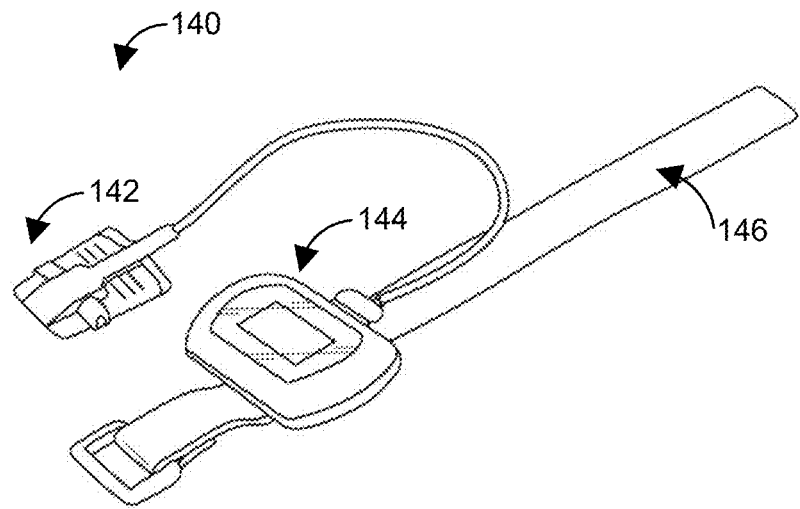
FIG. 1E shows an example oximeter sensor device in accordance with one or more embodiments.

Referring next to FIG. 1E there is shown an example oximeter sensor device 140 in accordance with one or more embodiments. The oximeter sensor device 140 may have a body contact portion 142, a processor portion 144, an attachment means 146 such as a hook and loop fastener, or a watch strap style attachment, or another attachment means as known.

In one embodiment, the oximeter device may be integrated with the one or more sensors of the patch device. The skin portion 142 in this case may be incorporated into the patch device and the patch may collect oximeter data from the skin portion that the patch device is attached to.

In an alternate embodiment, the oximeter device 140 may be a separate device that may communicate with the hub device. The skin portion 142 may be attached to a subject's fingertip, and the attachment means 146 may attach the processor portion 144 to the wrist of the subject. The processor portion 144 may collect the oximeter data and transmit it to the hub device wirelessly.

Figure 1F:
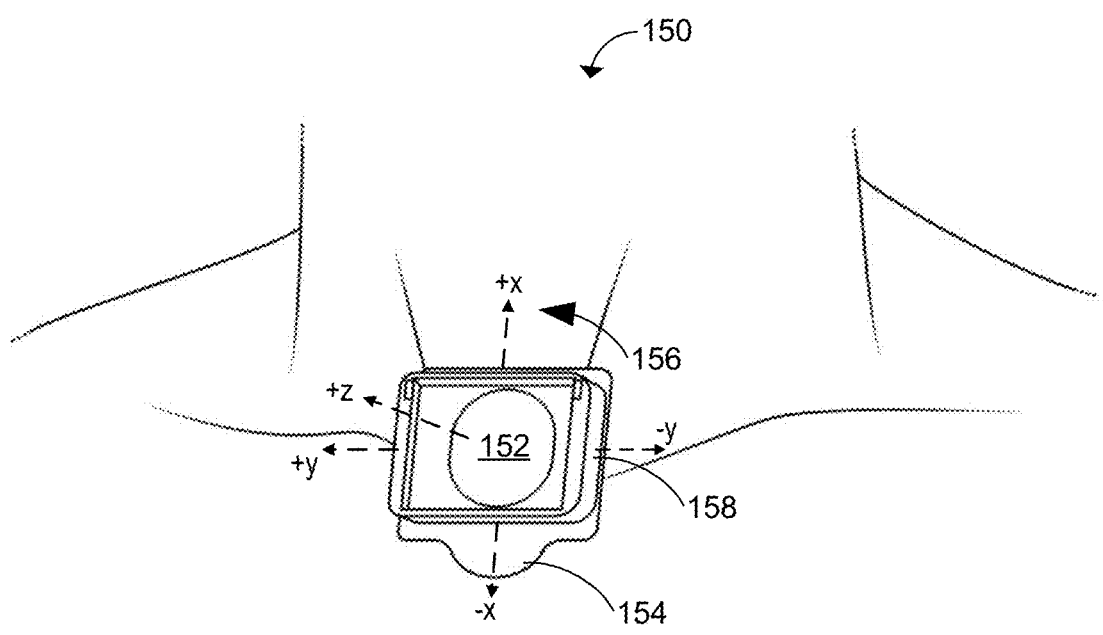
FIG. 1F shows the placement device in position on a subject's suprasternal notch in preparation for receiving an example patch sensor device in accordance with one or more embodiments.

Referring next to FIG. 1F there is shown the placement device 158 in position 150 on a subject's suprasternal notch in preparation for receiving an example patch sensor device in accordance with one or more embodiments. The placement device 158 may be attached to the skin of the subject's suprasternal notch 156 using an adhesive tape 154, glue, or another attachment means. The patch device (not shown) may be attached to the placement device 158 such that the one or more sensors of the patch device may be proximate to the sensor aperture 152.

A subject may attach or affix a patch device on their body using the placement device 158. The patch device 110 may be attached or affixed using the placement device 158 on the chest, on the back, or in a preferred embodiment, at the suprasternal notch as shown. The placement device 158 may be incorporated into the patch device in some embodiments.

In one or more embodiments, there may be two or more patch devices affixed to the subject, and the two or more patch devices may communicate with a hub device proximate to the subject's bed.

Each patch device may include a plurality of sensor devices, including but not limited to, one or more audio input devices such as one or more microphones, one or more accelerometers, and one or more oximeters.

In one or more embodiments, the one or more audio input devices may collect audio data of the subject as they fall asleep, and during the period of time they sleep.

In one or more embodiments, the one or more accelerometers may measure the subject's movement in one or more dimensions. The audio data may include audio data in a variety of different formats.

In one or more embodiments, the subject may also wear an oximeter device for collecting blood oxygenation data from the subject on their hands, fingers, toes, or another body part separate from the patch device. In one or more embodiments, each patch device may further include an oximeter sensor device.

While the one or more patch devices (and optionally the oximeter device) are attached to the subject's body, the subject may go to sleep. The subject may set up the hub proximate to their bed, for example, on a nightstand, desk, table, or somewhere within the bedroom. The patch device and the hub system may be "paired" or otherwise connected wirelessly or using a wired connection as described herein.

Figure 2A:
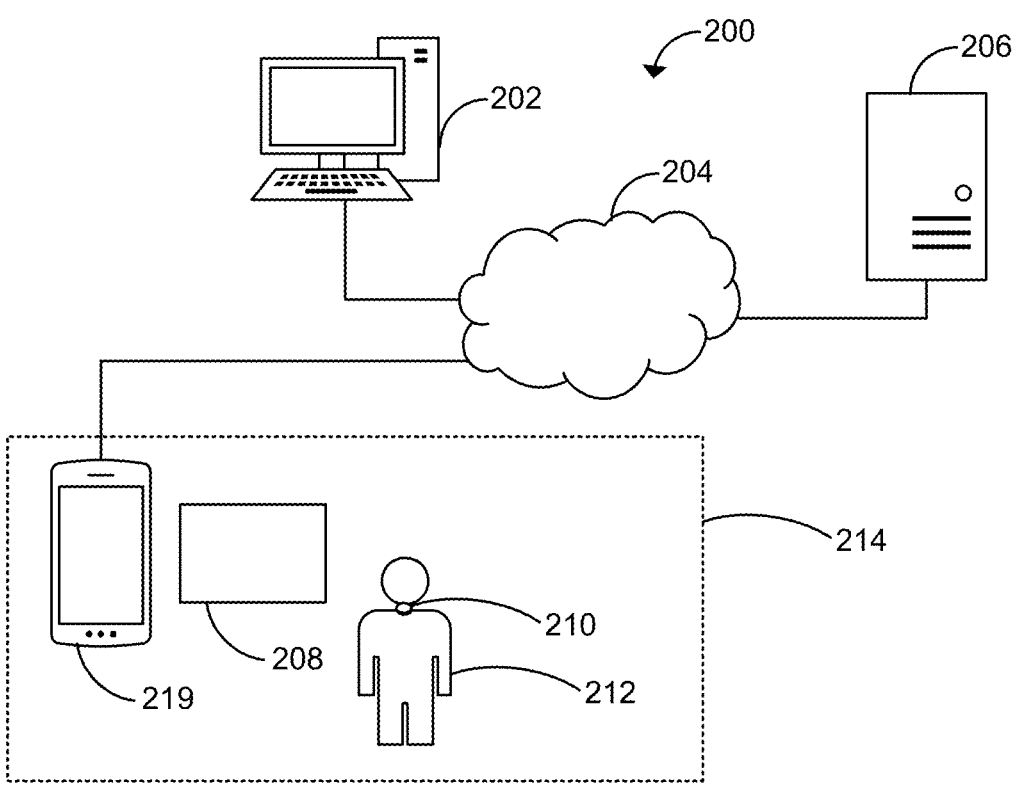
FIG. 2A shows an example breathing prediction system for breathing signal analysis and breathing event detection in accordance with one or more embodiments.

Referring next to FIG. 2A there is shown a system diagram 200 of an example breathing prediction system for breathing signal analysis and breathing event detection in accordance with one or more embodiments. The system 200 has a clinician device 202, network 204, server 206, hub device 208, subject device 219 and patch device 210 for subject 212 at locale 214.

The one or more clinician devices 202 may be desktop computers, laptop computers, portable computers, mobile devices such as an Apple® iOS® based device or Google® Android® based device, etc. The clinician device 202 may be any two-way communication devices with capabilities to communicate with other devices.

The clinician device 202 may include a web browser and may access a web application of server 206. Alternatively, the clinician device 202 may execute an application that communicates with server 206 in a client-server manner. For example, the application may be distributed via the Google Play Store® or the Apple® AppStore®. In addition to the client application and/or the web application, the server 206 may further provide an Application Programming Interface (API) for the clinician device 202, the hub device 208 and/or the patch device 210. The clinician device 202 may be used by a clinician to access clinician interfaces such as those found in FIGS. 21F and 21G.

Figure 5:
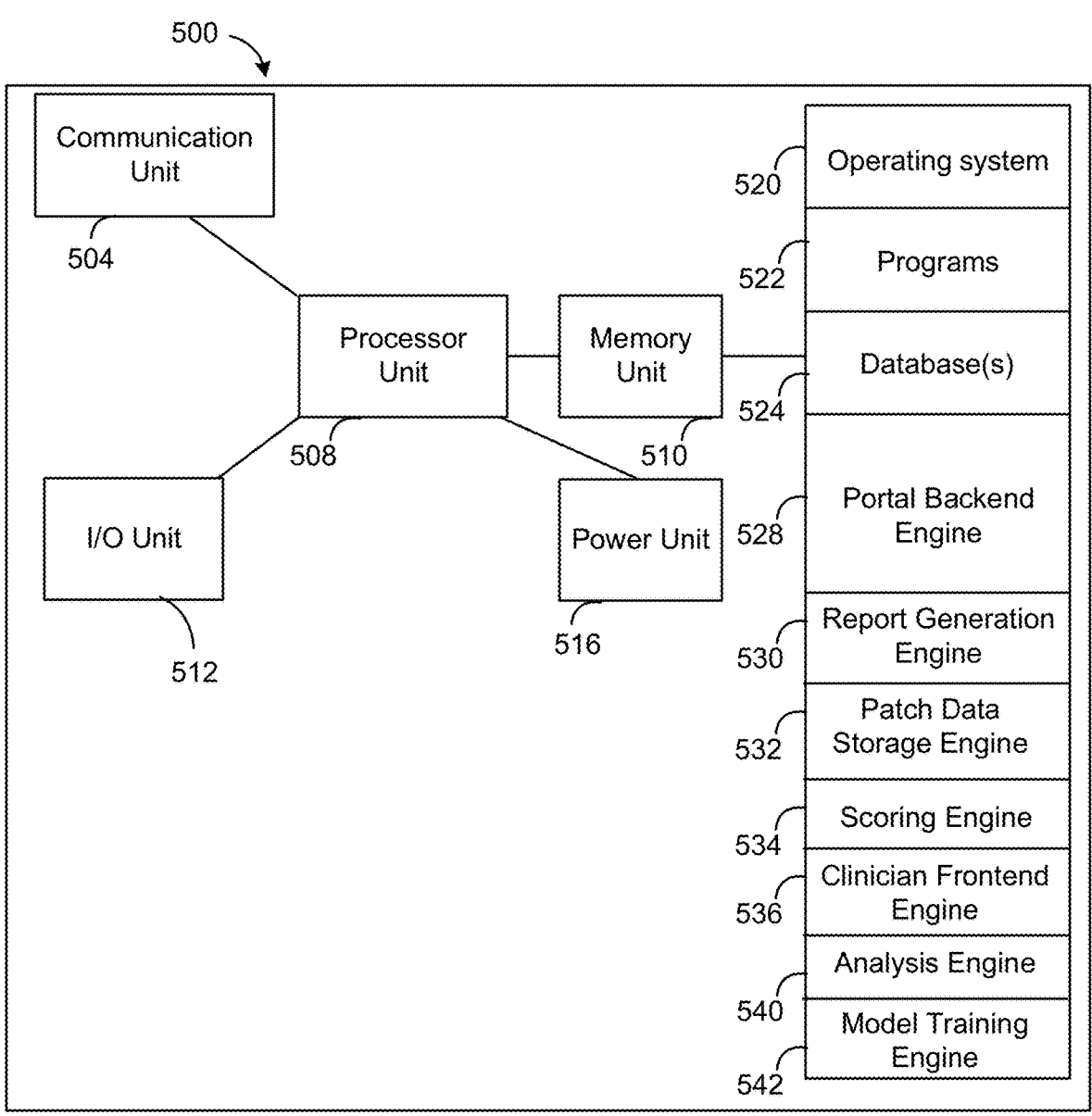
FIG. 5 shows an example server device for breathing signal analysis and breathing event detection in accordance with one or more embodiments.

Each of server 206 and hub device 208 may have an API to provide for various functions as described in FIG. 5 for patch device 210 and in FIG. 4 for hub device 208 to collect sensor data from subject 212 while the subject 212 sleeps. The hub device 208 may have an API for receiving sensor data from the patch device 210, which may be received when the patch is docked, or may be received generally in real-time via wireless communication. The server 206 may have an API for receiving data uploads from the hub device 208 and/or the patch device 210, processing sensor data, manual scoring, and report generation. The sensor data transmission between patch device 210, hub device 208 and server 206 may be generally in real-time. In an alternate embodiment, the sensor data transmission between patch device 210, hub device 208 and server 206 may be performed at the end of the subject's 212 sleep session, or periodically during the sleep session. The subject 212, or a clinician associated with the subject 212 may initiate the data upload from hub device 208 to the server 206 by accessing a user interface provided by the hub device 208 (or by an application running on a subject or clinician device 219) and initiating the sensor data upload (for example, as described in FIG. 21E). In an alternate embodiment, the data upload from hub device 208 to the server 206 may be initiated automatically.

In one embodiment, a separate hub device 208 is provided, where the hub device 208 receives data from the patch device 210 as described herein. In an alternate embodiment, the functionality of the hub device 208 may alternatively be provided by server 206 where the patch device 210 communicates with the server 206.

The client application or the web application provided by server 206 may provide functionality for a user of the clinician device 202 to review and present sleep events detected during the sleep session of subject 212 (see e.g. FIG. 21G), including for example, sleep time, sleep score, number of detected respiratory (OSA and CSA) events within the sleep session, number of oxygen desaturations, oxygen desaturation index, upright position time, number of supine events, supine time, severity of supine events such as a respiratory event index, severity of the respiratory events (OSA and CSA) such as a respiratory event index, number of non-supine events, severity of non-supine events such as a respiratory event index, minimum oxygen saturation, maximum oxygen saturation, average oxygen saturation, minimum heart rate, maximum heart rate, and other test data for the subject 212.

The network 204 may be any network or network components capable of carrying data including the Internet, Ethernet, fiber optics, satellite, mobile, wireless (e.g. Wi-Fi, WiMAX), SS7 signaling network, fixed line, local area network (LAN), wide area network (WAN), a direct point-to-point connection, mobile data networks (e.g., Universal Mobile Telecommunications System (UMTS), 3GPP Long-Term Evolution Advanced (LTE Advanced), Worldwide Interoperability for Microwave Access (WiMAX), etc.) and others, including any combination of these.

The server 206 may be the server 500 as shown in FIG. 5. The server 206 manages the collected sensor data generated by hub device 208 and patch device 210 and facilitates the generation, storage, and presentation of reports and other information for clinicians at clinician device 202. For example, the server 206 may allow a user at clinician device 202 to add OSA/CSA scores based on the collected sensor data of a subject 212. The server 206 may include user authentication of clinician users at the clinician device 202, or the hub device 208 and patch device 210. The server 206 may perform analysis of the collected sensor data to identify OSA and CSA events during the sleep of subject 212, such as the automatic analysis described herein (see e.g. 268 in FIG. 2B). The server 206 may receive encrypted sensor data from the hub device 208 and may decrypt the sensor data and store it on a storage device (not shown) or database (not shown). The server 206 may use a local file storage device or may be in communication with a cloud-based storage system such as Amazon® S3. The server 206 may use a local database running on the server 206 or may communicate with a cloud-based database system such as Amazon® Relational Database Service (RDS).

The database of server 206 may be a Structured Query Language (SQL) such as PostgreSQL or MySQL or a not only SQL (NoSQL) database such as MongoDB, or Graph Databases etc.

The hub device 208 may be the hub device 400 in FIG. 4. The hub device 208 and patch device 210 may be any two-way communication devices with capabilities to communicate with other devices.

The hub device 208 may execute an application that communicates with server 206 in a client-server manner, and further may communicate with the patch device 210. The hub device 208 may be in wired or wireless communication with patch device 210. For example, the hub device 208 may have a client application thereon which may be distributed via the Google® Play Store® or the Apple® AppStore®. In addition to the client application and/or the web application, the server 206 may further provide an Application Programming Interface (API) for the hub device 208 and/or the patch device 210.

The subject device 219 may be a desktop computer, laptop computer, portable computer, mobile device such as an Apple® iOS® based device or Google® Android® based device, etc. The subject device 219 may be on the same network as the hub device 208 and the patch device 210. The subject device 219 may allow a user to access an ad hoc wireless network generated by the hub device 208. The subject device 219 may access a web-based interface such as those found in FIGS. 21A, 21B, 21C, 21D, and 21E on the hub device 208 to receive user interfaces of the hub device, including for configuration and to initiate sensor data collection when they are about to go to bed. The subject device 219 may have an application such as an app downloaded from an app store or a browser that can access the user interfaces of the hub device 208 such as FIGS. 21A, 21B, 21C, 21D, and 21E. This may include communicating with an API of the hub device 208 to perform configuration and to initiate sensor data collection as described herein. The hub device 208 may be configured by the subject user device 219 or may be configured by a clinician or administrator user using their own device also.

The patch device 210 may be the patch device 300 in FIG. 3 and may be affixed or attached to the body of the subject 212. The patch device 210 may have one or more sensor devices for collecting data about subject 212 as the subject 212 falls asleep and while the subject 212 is asleep.

The locale 214 may be a room, including at the residence of the subject 212 such as the subject's 212 bedroom. In one or more embodiments the locale 214 may be a clinical sleep facility, for example at a medical center or medical organization. The patch device 210, the subject user device 219 and the hub device 208 may be proximate to one another in the locale 214.

Figure 2B:
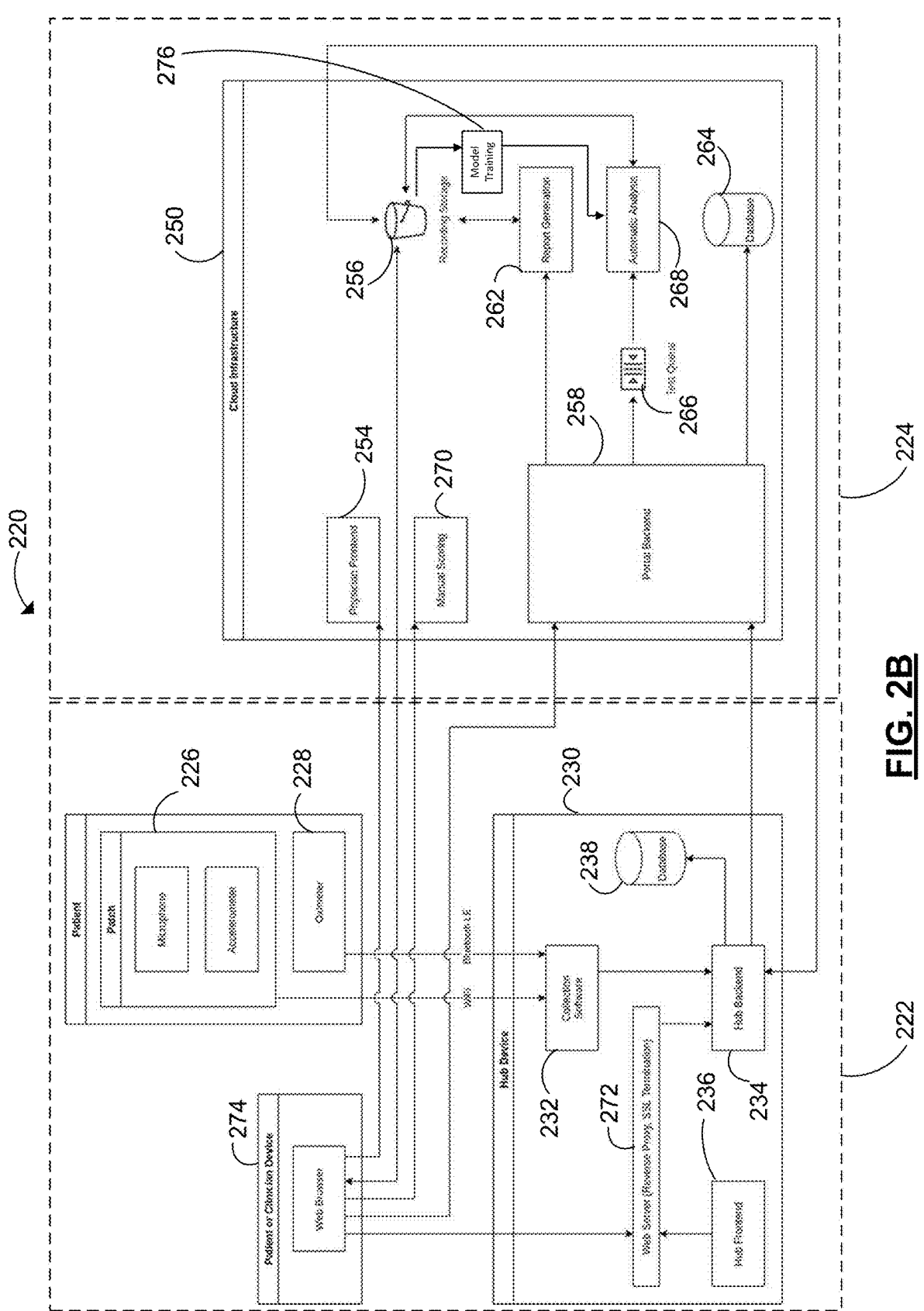
FIG. 2B shows another example breathing prediction system for breathing signal analysis and breathing event detection in accordance with one or more embodiments.

Referring next to FIG. 2B there is shown a system diagram 220 of another example breathing prediction system for breathing signal analysis and breathing event detection in accordance with one or more embodiments.

The system 220 may include an on-locale portion 222 and a server portion 224.

The on-locale portion 222 may include a patch device 226, a hub device 230, an optional oximeter 228, and a hub frontend 236. The oximeter 228 and the patch device 226 may be in wireless communication with the hub device 230 for the transfer of sensor data. In some cases, the patch device may be in wired communication with the hub device 230 for sensor data transfer. In some cases, the patch device 226 may attach or "dock" with the hub device 230 for transfer of sensor data.

The patch device 226 may be the patch device 300 in FIG. 3 and may be attached to a subject's body. The patch device 226 may include one or more sensor devices for recording sensor data, including one or more microphones and one or more accelerometers.

The oximeter 228 may be a pulse oximeter worn on, for example, a fingertip, a toe-tip, or another portion of a subject's skin. The oximeter may be one such as a Masimo Radical-7 (USA), Nihon Kohden OxyPal Neo (Japan), Nellcor N-600 (USA) and a Philips Intellivue MP5 (USA).

The subject or clinician device 274 may be the subject or clinician device as shown in system 220 (see FIG. 2A). The subject device 274 may have a web browser or another software application to access a web server 272 of the hub device 230, physician frontend 254 of server 250, or manual scoring interface 270 of server 250.

The hub device 230 may be one such as the hub device 400 in FIG. 4. The hub device 230 may have hub collection engine 232, one or more databases 238, a hub backend engine 234, and a backend database 238. The hub device 230 may provide an ad hoc wireless network and a web server 272 which may provide for hub device pairing and configuration as described in FIGS. 21A, 21B, and 21C.

The web server 272 may be nginx, Apache, or an embedded web server as known, which may provide user interfaces to a user, subject, or clinician who wishes to interact with hub device 230 and patch device 226. The web server 272 may provide the user interfaces found in FIGS. 21A, 21B, 21C, 21D, and 21E.

The hub collection engine 232 may receive sensor data from oximeter device 228 and patch device 226, via wireless communication, wired communication, or via docking of the patch device 226 with the hub device 230. The sensor data received by hub collection engine 232 may include accelerometer data, one or more channels of audio data, and blood oxygen saturation data. The audio data received by hub collection engine 232 may be in an uncompressed audio format such as WAV, AIFF, AU or raw headerless PCM, lossless compression such as FLAC, Monkey's Audio (filename extension .ape), WavPack (filename extension .wv), TTA, ATRAC Advanced Lossless, ALAC (filename extension .m4a), MPEG-4 SLS, MPEG-4 ALS, MPEG-4 DST, Windows Media Audio Lossless (WMA Lossless), and Shorten (SHN), or lossy compression such as Opus, MP3, Vorbis, Musepack, AAC, ATRAC and Windows Media Audio Lossy (WMA lossy). The audio data may be received at a variety of bit rates, such as any resolution of 4 to 32 bits, or higher. The audio data may be received at a variable bit-rate. The audio data may include a plurality of channels. The sampling rate of the audio data may be a fixed sampling rate from 1 Hz to 65,535 Hz in 1 Hz increments or from 10 Hz to 655,350 Hz in 10 Hz increments. The sampling rate of audio data may be variable. In an exemplary embodiment, the sampling frequency of the audio data may be 8 kHz. The sleep session recording may be controlled by a user accessing a web server 272 on hub device 230, as described in FIG. 21D.

The accelerometer data received by the hub collection engine 232 may be a time series of acceleration values from the one or more accelerometers. The accelerometer on the patch device 226 may be multidimensional and there may be a plurality of channels of accelerometer data corresponding to a plurality of directional acceleration components, such as translational acceleration in x, y, and z axes. The accelerometer data may be generated as triplets of (x, y, z) components. The sensitivity of the accelerometer in an exemplary embodiment may be +/−2 g. The sensitivity of the accelerometer may be impacted by the bit depth of each sample. In an exemplary embodiment, the accelerometer data may have a bit depth of 12 bits per axis per sample, or 36 bits total per sample. The accelerometer may further include a gyroscope and the accelerometer data may include rotational gyroscopic measurements in pitch, yaw, and roll axes. The sampling rate of the accelerometer data may be a fixed sampling rate from 1 Hz to 65,535 Hz in 1 Hz increments or from 10 Hz to 655,350 Hz in 10 Hz increments. The sampling rate of accelerometer data may be variable. In an exemplary embodiment, the sampling rate of the accelerometer may be 100 Hz.

The one or more databases 238 may store collected sleep sensor data from the patch device 226, oximeter 228, and related sleep session metadata. The database 238 may be in memory or on a storage device of the hub device 230. The database 238 may be an SQLlite database, a MySQL database, an embedded database, or another database as known. The sleep sensor data and the sleep session metadata in database 238 may be encrypted at rest on the hub device 230.

The oximeter data received by the hub collection engine 232 may be time series data including a plurality of pulse rates and oxygen saturation levels. The sampling rate of the oximeter data may be a fixed sampling rate from 1 Hz to 65,535 Hz in 1 Hz increments or from 10 Hz to 655,350 Hz in 10 Hz increments. The sampling rate of oximeter data may be variable.

The hub collection engine 232 may receive the sensor data including oximeter data, accelerometer data, and audio data, and may store it in the one or more databases 238. The one or more databases 238 may store the sensor data measurements together with other subject data or subject metadata. The one or more databases 238 may be a variety of different databases as known, either file-based or in-memory.

The hub collection engine 232 may provide sleep session metadata to the hub backend engine 234. The sleep session metadata may include traceability information regarding devices used in the recording, which may include serial numbers and software/hardware versions involved in the data collection. Further, the metadata may include timestamps of recording start and end times.

The hub backend engine 234 communicates with the server portion 224, provides a user interface such as the hub frontend 236 with sleep session metadata, and performs registration of the hub device 230 with the server portion 224 to authenticate the hub device with the server portion 224. The hub frontend 236 may be supported by the hub backend engine 234 by way of API calls to the server portion 224.

The hub backend engine 234 may store sleep sensor data and sleep session metadata in database 238.

The hub backend engine 234 may transmit collected sensor data in the one or more databases 238 to the server portion 224. The transmission of the collected sensor data in database 238 may be generally in real-time with its reception at the hub, i.e., the patch device 226 and the oximeter 228 may collect the sensor data and the hub device 230 may generally retransmit it to the server portion 224 generally in real-time. In one or more cases, the sensor data may be transmitted periodically during a sleep session to the server portion 224. The transmission of the collected sensor data may be an encrypted transmission, for example, using TLS. In one or more cases, a batch transfer of the sensor data may occur at the end of the sleep session, when the subject "docks" the patch device 226 in the hub device 230. The hub backend engine 234 may transmit the sensor data to recording storage 256 of server portion 224, for example the recording storage 256 may be cloud-based storage such as Amazon® S3.

The hub backend engine 234 may authenticate the hub with the server portion 224. This may include a public key encryption public key exchange, to allow for encrypted communications between the hub device 230 and the server portion 224.

The hub frontend 236 may be a user interface on the hub device 230. The hub frontend 236 may allow for user interaction with the hub device. The hub frontend 236 may enable a subject to begin a sleep session, calibrate the sensors, connect the patch device 226 with the hub device 230, connect the hub device 230 with the server portion 224. The hub frontend 236 may further enable the control and configuration of the patch device 226, oximeter device 228, and hub device 230. The hub frontend 236 may appear on the display device of a mobile device or may have a dedicated display device.

The hub backend engine 234 may provide an API that may be accessed by the server portion 224 in a "pull" architecture to collect sensor data. In one or more cases, the hub backend engine 234 may alternatively "push" sensor data to the server portion 224.

The server portion 224 including cloud infrastructure 250 may be a physical server or may be a cloud-based provider such as Amazon® Web Services (AWS). The server portion 224 and the on-locale portion 222 are in communication over the internet, or another network.

The server portion 224 may have cloud infrastructure 250, and a clinician frontend 254.

The cloud infrastructure 250 may include recording storage 256, manual scoring interface 270, report generation 262, portal backend 258, one or more server databases 264, an analysis engine 268 and a processing queue 266.

The recording storage 256 may be a file storage device at server portion 224, or alternatively may be cloud storage service such as Amazon® S3.

As sensor data is received by recording storage 256, it may be automatically analyzed by automatic analysis engine 268. In some cases, a clinician user may request automatic analysis at clinician frontend 254, and portal backend 258 may enqueue the request for automatic processing in processing queue 266. In some cases, once a sensor data collection complete message is received from the hub device, the sensor data and/or metadata may be enqueued in processing queue 266 for processing. In some cases, the automatic analysis engine 268 may request sensor data from recording storage 256. The automatic analysis engine 268 may receive a message from the processing queue 266 corresponding to a request for processing from a clinician, based on the completion of sensor data collection. The automatic analysis engine 268 may dequeue an analysis request including sensor data and/or metadata from the processing queue 266.

Figure 7B:
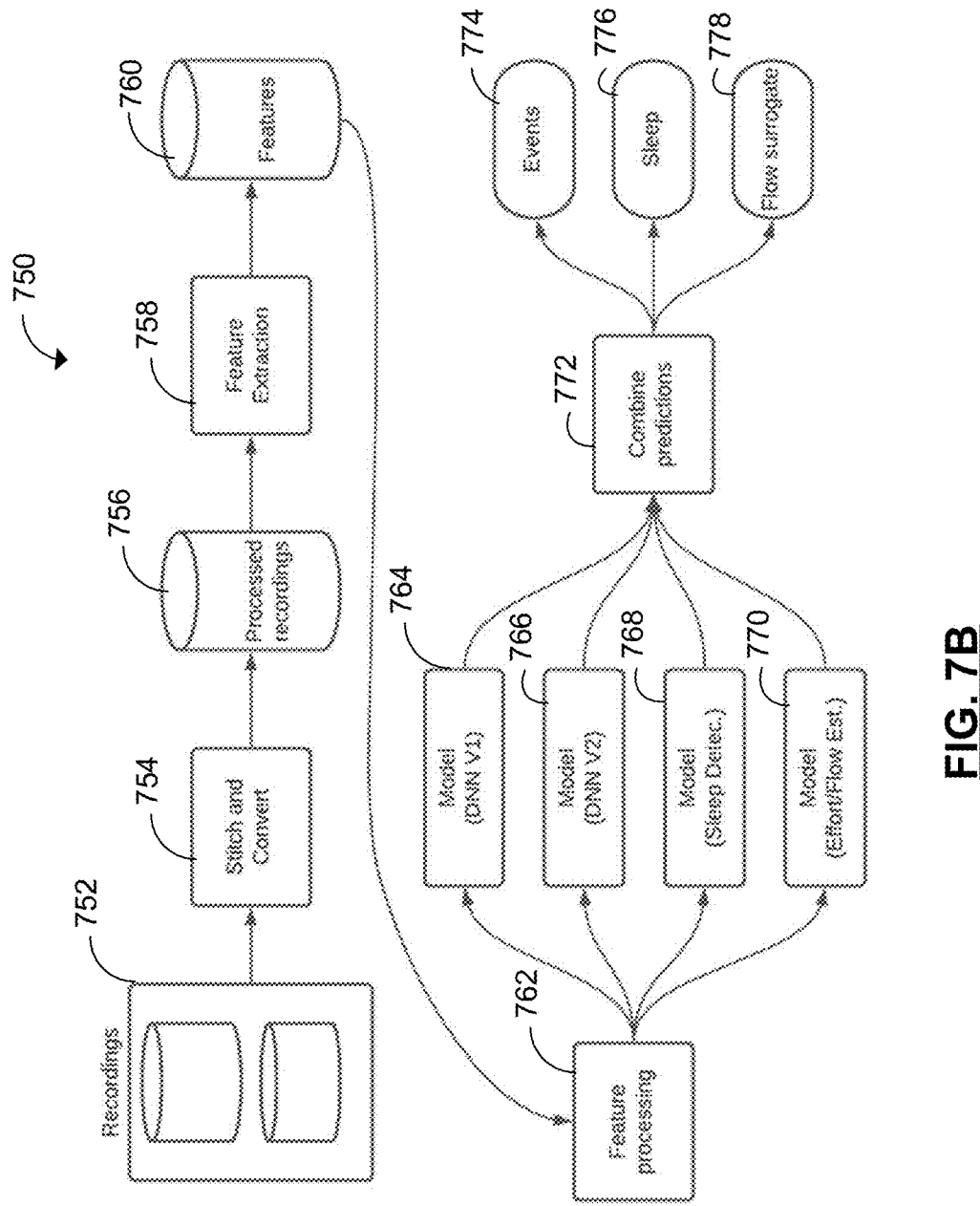
FIG. 7B shows an example method of breathing event inference and prediction in accordance with one or more embodiments.

The automatic analysis engine 268 may receive sensor data and metadata and may use a predictive model to identify portions of the sensor data that are indicative of OSA or CSA in the subject, as described in FIGS. 7A and 7B. The automatic analysis engine 268 may perform signal processing on the sensor data, as described in FIG. 6. The automatic analysis engine 268 may transmit analysis information back to the portal backend 258, which may be stored in database 264 including analysis information that may be reviewed as a report by a clinician at clinician frontend 254. The analysis information generated at automatic analysis engine 268 may include time referenced annotations of the sensor data. The automatic analysis algorithm may create a European Data Format (EDF) file, or EDF-like file with automatically scored events, sleep status, etc., encoded therein. This file may then be loaded into the manual scoring application 270 for review by a clinician before a report is generated at 262. The completion of the automatic analysis may notify the portal backend 258, which may in turn trigger report generation 262.

A user may access the manual scoring interface 270 using a web browser or using an application in communication with an API of the server portion 224 to review collected sensor data and score portions of the sensor data as indicative of OSA or CSA. The manual scoring interface 270 may allow a user to review the sensor data and download it from recording storage 256. The manual scoring interface 270 may allow a user to create an annotation at a time-index of the sensor data indicating an event or indication of OSA or CSA. The generated annotations indicating OSA or CSA events may be used as training data in order to generate a predictive model. The manual scoring interface 270 may be provided via clinician frontend 254. Based on the user's interaction with manual scoring interface 270, a call may be made to the portal backend 258. This may include the annotations created by the user of the manual scoring interface 270, or other metadata. A revision of the test results may be created as the user of the manual scoring interface 270 modifies the existing annotations. The revision may consist of the updated annotations stored in cloud storage 256 and a portal backend database record in database 264 containing metrics computed from the annotations, for example respiratory event index (REI), monitoring time, number of events, etc.

In an exemplary embodiment, a user may access the report generation 262 using a web browser or using an application in communication with an API of the server portion 224 to request a report for a subject using a patch device 226 and a hub device 230.

In an alternate embodiment, the report generation 262 may also be automatically triggered once analysis information is received at portal backend 258, and report generation engine 262 is triggered.

The reports generated by report generation engine 262 may include a variety of information, including statistics related to the sensor data, metadata associated with the sensor data collection, the sensor data itself, and analysis information generated by the automated analysis engine 268.

The portal backend 258 may send and receive messages with the hub devices 230. The portal backend 258 may provide an API for the clinician frontend 254, such that a user of the clinician frontend 254 may view subject information, sensor data, and report data generated by report generation engine 262.

The portal backend 258 may authenticate hub devices 230. The portal backend 258 may check permissions of a requesting hub device and may provide a response to the hub device based on the message or request. These messages or requests may include configuration requests and messages indicating the completion of a sleep session by a subject. The hub backend 234 may request authorization from portal backend 258 to upload sleep recording data to cloud storage 256.

The portal backend 258 may send and receive requests and responses from a plurality of hub devices including hub device 230. The portal backend 258 may facilitate communications between the hub device 230 and the cloud infrastructure 250. This communication may include requests from the hub device 230 to the cloud infrastructure 250, for example, when the hub device 230 transmits sensor data to the server portion 224, a request may be generated including subject metadata, patch metadata, or hub metadata which corresponds to the transmitted sensor data. The portal backend 258 may send and receive messages with a hub backend 234 of the hub device 230. The hub device 230 may transmit a message to portal backend 258 when sensor data is finished being collected. The portal backend 258 may receive the sensor data complete message and may request processing of the collected sensor data, and responsive to the processing request, the portal backend 258 may enqueue the sensor data and metadata received from the hub device in processing queue 266 for processing by automatic analysis engine 268.

The portal backend 258 may receive manual scoring requests from the manual scoring interface 270 and may store them in the database 264. The portal backend 258 may receive analysis information for a sleep session from automatic analysis engine 268 and may store the analysis information in database 264. The portal backend 258 may trigger a report to be generated by report generation engine 262 based on analysis information received from the automatic analysis engine 268 or stored in database 264.

The portal backend 258 may enqueue requests for analysis including sensor data and metadata in the processing queue 266. The portal backend 258 may receive notifications from the analysis engine 268 once analysis of a request in the processing queue 266 is competed.

The server portion 224 may have one or more server databases 264, which may be of a variety of different types as known, for example, a Postgres database or a MySQL database. The one or more server databases 264 may contain subject information, hub device information, patch device information, sensor data, test metadata associated with subject sleep sessions, generated report information for sleep sessions including result metrics and report revisions (produced by the analysis engine 268 or manual scoring interface 270), configuration options, test access permissions (such that clinicians can share test report information with one another, user data, and user authentication information). The one or more databases 264 may include a plurality of sleep session records, including corresponding sensor data and one or more annotations of the corresponding sensor data. The plurality of sleep session records may be used by the model training engine 276 as described herein in FIG. 13B to generate a predictive model that may be used by automatic analysis engine 268.

The model training engine 276 may query recording storage 256 and may execute the method of FIG. 13B in order to train one or more models.

The processing queue 266 may be a queue such as Amazon® Simple Queue Service (SQS), or ActiveMQ. The processing queue 266 may be a first-in-first-out (FIFO) queue.

The clinician frontend 254 may be an interface that allows for the review of information stored in database 264 or recording storage 256, including subject reports generated by report generation engine 262, analysis data 268, sensor data, metadata, manual scoring data, or any other data required by the clinician to review the collected sleep sensor data and related analysis and reporting by the server portion 224.

Referring next to FIG. 3 there is shown a device diagram 300 of an example patch device for breathing signal analysis and breathing event detection in accordance with one or more embodiments. The patch device 300 may be the patch device 210 (see FIG. 2A) and/or the patch device 226 (see FIG. 2B). As noted above, the patch device 300 may communicate wirelessly with a hub device. Alternatively, the patch device 300 may communicate via a wired connection with a hub device. Alternatively, the patch device 300 may communicate with a hub device by way of its attachment to the hub device by "docking".

The patch device 300 is affixed or attached to the skin of the subject being monitored. This may include using glue, adhesive, straps, or other skin attachments such that the patch device 300 is directly connected to the skin of the subject.

The patch device 300 includes a communication unit 304, a processor unit 308, a memory unit 310, an I/O unit 312 and a power unit 316.

The patch device 300 may be, for example, an Arduino® or Raspberry Pi® device.

The communication unit 304 can include wired or wireless connection capabilities. The communication unit 304 can include a radio that communicates utilizing CDMA, GSM, GPRS or Bluetooth protocol according to standards such as IEEE 802.11a, 802.11b, 802.11g, or 802.11n. The communication unit 304 may implement a bespoke communication protocol that operates at lower power. The communication unit 304 may communicate using Bluetooth or Bluetooth Low Energy. The communication unit 304 can be used by the patch device 300 to communicate with the hub device.

Communication unit 304 may communicate wirelessly with the hub device to transfer sensor data. Communication unit 304 may alternately connect to the hub device by a physical connection, e.g., by "docking" with the hub device. In an alternate embodiment, the communication unit 304 may transmit and receive information via local wireless network with the hub device. In an alternate embodiment, the patch device 300 may communicate directly with a server, and the functions of the hub device may be performed by the server.

The processor unit 308 controls the operation of the patch device 300. The processor unit 308 can be any suitable processor, controller or digital signal processor that can provide sufficient processing power depending on the configuration, purposes, and requirements of the patch device 300 as is known by those skilled in the art. For example, the processor unit 308 may be a low power mobile processor such as an ARM-based processor. In alternative embodiments, the processor unit 308 can include more than one processor with each processor being configured to perform different dedicated tasks. In alternative embodiments, it may be possible to use specialized hardware to provide some of the functions provided by the processor unit 308. For example, the processor unit 308 may include a standard processor, such as a Qualcomm® Snapdragon® processor, an ARM® processor or a microcontroller.

The memory unit 310 comprises software code for implementing an operating system 320, programs 322, oximeter engine 324, accelerometer engine 326, audio engine 328, and a hub engine 330.

The memory unit 310 can include RAM, ROM, one or more hard drives, one or more flash drives, or some other suitable data storage elements such as disk drives, etc. The memory unit 310 is used to store an operating system 320 and programs 322 as is commonly known by those skilled in the art.

The I/O unit 312 can include at least one of a button, an indicator light, a speaker, a display, voice recognition software and the like again depending on the particular implementation of the patch device 300. The I/O unit 312 is further connected to an audio sensor 336, an accelerometer 338, and optionally an oximeter 340. In some cases, some of these components can be integrated with one another.

The audio engine 328 may receive audio sensor data from the audio sensor 336 of the patch device from a subject. The audio sensor 336 may collect the audio sensor data from a subject and may include one or more microphones. The audio sensor 336 may collect audio data at a variety of bit rates, such as any resolution of 4 to 32 bits, or higher. The audio sensor 336 may receive audio data at a variable bit rate. The audio sensor 336 may receive audio data that includes a plurality of channels. The sampling rate of the audio data by the audio sensor 336 may be a fixed sampling rate from 1 Hz to 65,535 Hz in 1 Hz increments or from 10 Hz to 655,350 Hz in 10 Hz increments. The sampling rate of audio data by the audio sensor 336 may be variable.

The accelerometer engine 326 may receive accelerometer data from the accelerometer 338. The accelerometer 338 may collect a plurality of accelerometer signals from a subject as they fall asleep and while they are sleeping. The accelerometer data may be a time series of acceleration values from the plurality of accelerometer signals. The accelerometer 338 on the patch device 300 may be multi-dimensional and there may be a plurality of channels of accelerometer data produced corresponding to a plurality of directional acceleration components, such as translational acceleration in x, y, and z axes. The accelerometer 338 may further include a gyroscope and the accelerometer data may include rotational gyroscopic measurements in pitch, yaw, and roll axes. The sampling rate of the accelerometer 338 may be a fixed sampling rate from 1 Hz to 65,535 Hz in 1 Hz increments or from 10 Hz to 655,350 Hz in 10 Hz increments. The sampling rate of accelerometer data may be variable.

In one embodiment, the oximeter is optionally integrated with the patch device and the oximeter engine 324 may receive oximeter data from an oximeter 340, and the oximeter data may be time series data including a plurality of pulse rate and oxygen saturation levels. The sampling rate of the oximeter 340 may be a fixed sampling rate from 1 Hz to 65,535 Hz in 1 Hz increments or from 10 Hz to 655,350 Hz in 10 Hz increments. The sampling rate of oximeter data may be variable.

In an alternate embodiment, the oximeter is a separate $3^{rd}$ party oximeter and may send oximeter data to the hub device. In this alternate embodiment, the functionality of the oximeter engine 324 may be instead performed at the hub device and the oximeter may transmit the oximeter data wirelessly to the hub device.

The operating system 320 may provide various basic operational processes for the patch device 300. The operating system 320 may be an embedded operating system, such as a real-time operating system. The operating system 320 may be embedded Linux, Android, FreeRTOS, or another embedded operating system as known.

The programs 322 may include various user programs so that a user can interact with the patch device 300 to perform various functions such as, but not limited to collecting, processing, and transmitting sensor data.

The oximeter engine 324 may receive oximeter data from oximeter 340 and may perform pre-processing of oximeter data.

The accelerometer engine 326 may receive accelerometer data from one or more accelerometers 338 and may perform pre-processing of the accelerometer data.

The audio engine 328 may receive audio data from the one or more audio sensors 336.

The hub collection engine 330 may receive sensor data including audio data from the audio engine 328, accelerometer data from the accelerometer engine 326, and optionally oximeter data from the oximeter engine 324. The hub collection engine 330 may compress and prepare the sensor data for transmission via communication unit 304 to a hub device. The hub collection engine 330 may receive configuration requests or other messages from the hub device via communication unit 304.

The hub collection engine 330 may store collected sensor data in memory unit 310, either in a database or another data structure. The hub collection engine 330 may detect the docking of the patch device 300 in a hub device and may initiate the transmission of the collected sensor data from the patch device to the hub device. In some cases, the hub collection engine may receive a request from a hub device to transmit sensor data wirelessly to the hub device. The hub collection engine 330 may supplement the sensor data with other patch device data and patch device metadata.

The power unit 316 can be any suitable power source that provides power to the patch device 300 such as a power adaptor or a rechargeable battery pack depending on the implementation of the patch device 300 as is known by those skilled in the art. The hub device may charge the power unit 316 of the patch device 300 when the patch device 300 is docked with the hub device.

Referring next to FIG. 4 there is shown another device diagram 400 of an example hub device for breathing signal analysis and breathing event detection in accordance with one or more embodiments. The hub device 400 may be the hub device 208 (see FIG. 2A) or the hub device 230 (see FIG. 2B). The hub device 400 has a communication unit 404, a display 406, a processor unit 408, a memory unit 410, an I/O unit 412 and a power unit 416. The hub device 400 may be a mobile device such as one running Google® Android® or Apple® iOS®.

The communication unit 404 can include wired or wireless connection capabilities. The communication unit 404 can include a radio that communicates utilizing 4G, LTE, 5G, CDMA, GSM, GPRS or Bluetooth protocol according to standards such as IEEE 802.11a, 802.11b, 802.11g, or 802.11n, etc. The communication unit 404 can be used by the hub device 400 to communicate with other devices or computers including the patch device and the server.

The display 406 may be an LED or LCD based display and may be a touch sensitive user input device that supports gestures. Alternatively, user interfaces may be provided via a web server running on the hub device 400 to a clinician or subject device in wireless communication.

The processor unit 408 controls the operation of the hub device 400. The processor unit 408 can be any suitable processor, controller or digital signal processor that can provide sufficient processing power depending on the configuration, purposes, and requirements of the hub device 400 as is known by those skilled in the art. For example, the processor unit 408 may be a high-performance general processor. In alternative embodiments, the processor unit 408 can include more than one processor with each processor being configured to perform different dedicated tasks. In alternative embodiments, it may be possible to use specialized hardware to provide some of the functions provided by the processor unit 408. For example, the processor unit 408 may include a standard processor, such as an Intel® processor, a Qualcomm processor, or an ARM®-based processor.

The memory unit 410 can include RAM, ROM, one or more hard drives, one or more flash drives, or some other suitable data storage elements such as disk drives, etc. The memory unit 410 may have an operating system 420, programs 422, one or more databases 424, collection engine 426, backend engine 428, and frontend engine 430.

The memory unit 410 is used to store an operating system 420 and programs 422 as is commonly known by those skilled in the art. For instance, the operating system 420 provides various basic operational processes for the hub device 400. For example, the operating system 420 may be a mobile operating system such as Google® Android® operating system, Apple® iOS® operating system, or a Raspberry Pi®-based Linux operating system, or another operating system.

The I/O unit 412 can include at least one of a mouse, a keyboard, a touch screen, a thumbwheel, a track-pad, a track-ball, a card-reader, voice recognition software, a button based interface and the like again depending on the particular implementation of the hub device 400. In some cases, some of these components can be integrated with one another. The I/O unit 412 may have an optional patch dock 432, which may receive the patch device and when docked may trigger a sensor data transfer from the patch device to the hub device.

The power unit 416 can be any suitable power source that provides power to the hub device 400 such as a power adaptor or a rechargeable battery pack depending on the implementation of the hub device 400 as is known by those skilled in the art.

The programs 422 may include various user programs so that a user can interact with the hub device 400 to perform various functions such as, but not limited to collecting, processing, and transmitting sensor data.

The one or more databases 424 may be configured to store sensor data, or other received patch data from the patch device. The database 424 may include file-based storage of the patch sensor data or an SQL database system such as PostgreSQL or MySQL or a not only SQL (NoSQL) database such as MongoDB, or Graph Databases etc.

The collection engine 426 may receive data from the communication unit 404 from a patch device. In some cases, the patch device may be docked in patch dock 432 on the hub device 400, and the collection engine 426 may receive data from the patch device by way of I/O unit 412. The collection engine 426 may store the received sensor data from the patch device in database 424.

The backend engine 428 may receive information from the patch device via the patch dock 432, or via wireless communication with communication unit 404. The backend engine 428 may send and receive configuration and control messages with a server. The backend engine 428 may store sensor data in the one or more databases 424, including sensor data, user input data, or other data.

The backend engine 428 may provide an API and/or support to the frontend engine 430 so that a user may interact with the hub device 400 and control its operation. This may include turning the device on and off, transmitting data, configuring the hub device or the patch device, etc.

The backend engine 428 may transmit sensor data to a remote server for analysis via communication unit 404.

The frontend engine 430 may provide a user interface via display 406 and may receive user input from a user input device connected to I/O unit 412 for operation of the hub device 400 or the patch device.

Referring next to FIG. 5 there is shown another device diagram 500 of an example server device for breathing signal analysis and breathing event detection in accordance with one or more embodiments. The server device 500 may be the server 206 (see FIG. 2A). The server 500 may be a physical server or may be a cloud-based provider such as Amazon® Web Services (AWS). The server portion 224 and the on-locale portion 222 are in communication over the internet, or another network.

The server 500 includes a communication unit 504, processor unit 508, memory unit 510, I/O unit 512, and power unit 516.

The communication unit 504 can include wired or wireless connection capabilities. For example, the communication unit 504 can include a radio that communicates utilizing 4G, LTE, 5G, CDMA, GSM, GPRS or Bluetooth protocol according to standards such as IEEE 802.11a, 802.11b, 802.11g, or 802.11n, etc.

The processor unit 508 controls the operation of the server 500. The processor unit 508 can be any suitable processor, controller or digital signal processor that can provide sufficient processing power depending on the configuration, purposes, and requirements of the server 500 as is known by those skilled in the art. For example, the processor unit 508 may be a high-performance general processor. In alternative embodiments, the processor unit 508 can include more than one processor with each processor being configured to perform different dedicated tasks. In alternative embodiments, it may be possible to use specialized hardware to provide some of the functions provided by the processor unit 508.

The memory unit 510 can include RAM, ROM, one or more hard drives, one or more flash drives, or some other suitable data storage elements such as disk drives, etc. The memory unit 510 comprises software code for implementing an operating system 520, programs 522, database(s) 524, portal backend engine 528, report generation engine 530, patch data storage engine 532, scoring engine 534, and clinician frontend engine 536, analysis engine 540, and model training engine 542.

The operating system 520 provides various basic operational processes for the operation of the server 500. For example, the operating system 520 may be a Microsoft® Windows Server® operating system, or a Linux®-based operating system, Unix® or macOS® or another operating system.

The programs 522 comprise program code that, when executed, configures the processor unit 508 to operate in a particular manner to implement various functions and tools for the server 500.

The database(s) 524 may be configured to collect the sensor data for all subjects using the patch and hub devices. The database(s) 524 may be on the server 500 or may be in network communication with the server 500. The database(s) 524 may be any database, such as, for example, MySQL®, Postgres®, or MongoDB®.

The portal backend engine 528 may send and receive requests and responses from a plurality of hub devices via communication unit 504. This communication between the hub device and the portal backend engine 528 may include requests from the hub devices to the portal backend engine 528, for example, when the hub device transmits sensor data to the server 500, a request may be generated including subject metadata, patch metadata, or hub metadata which corresponds to the transmitted sensor data. The portal backend engine 528 may receive the sensor data complete message, and may request processing of the collected sensor data, and responsive to the processing request, the portal backend engine 528 may enqueue the sensor data and metadata received from the hub device in a processing queue for processing by analysis engine 540.

As sensor data is received by patch data storage engine 532, it may be automatically analyzed by analysis engine 540. In some cases, a clinician user may request automatic analysis at clinician frontend engine 536, and portal backend engine 528 may enqueue the request for automatic processing in a processing queue. In some cases, once a sensor data collection complete message is received from the hub device via communication unit 504, the sensor data and/or metadata may be enqueued in a processing queue for processing. In some cases, the analysis engine 540 may request sensor data from patch data storage engine 532 and database(s) 524. The analysis engine 540 may receive a message corresponding to a request for processing from a clinician, based on the completion of sensor data collection, or as data is received from the hub device. The analysis engine 540 may dequeue an analysis request including sensor data and/or metadata from the processing queue.

The analysis engine 540 may receive sensor data and metadata and may use a predictive model to identify portions of the sensor data that are indicative of OSA or CSA in the subject, as described in FIGS. 7A and 7B. The analysis engine 540 may perform signal processing on the sensor data, as described in FIG. 6. The analysis engine 540 may transmit analysis information back to the portal backend engine 528, which may trigger a report based on the analysis information that may be reviewed by a clinician at clinician frontend engine 536. The report generation engine 530 may store the report in database 524. The analysis information generated at analysis engine 540 may include time referenced annotations of the sensor data. The completion of the analysis may notify the portal backend engine 528, which may in turn trigger report generation engine 530.

A user may access the scoring engine 534 via communication unit 504 using a web browser or using an application in communication with an API to review collected sensor data and score portions of the sensor data as indicative of OSA or CSA. The scoring engine 534 may allow a user to review the sensor data and download it from patch data storage engine 532. The scoring engine 534 may allow a user to create an annotation at a time-index of the sensor data indicating an event or indication of OSA or CSA. The generated annotations indicating OSA or CSA events may be used by the model training engine 542 as training data in order to generate a predictive model as described in FIG. 13B. The model training engine 542 may update the predictive model used by the analysis engine 540. The model training engine 542 may be, for example, the model training engine 276 (see e.g. FIG. 2B). The scoring engine 534 may be provided via clinician frontend engine 536 using communication unit 504. Based on the user's interaction with scoring engine 534, a call may be made to the portal backend engine 528. This may include the annotations created by the user of the scoring engine 534, or other metadata.

A user may access the report generation engine 530 via communication unit 504 using a web browser or using an application in communication with an API to request a report for a subject using a patch device and a hub device. The report generation engine 530 may also be automatically triggered once analysis information is received at portal backend engine 528, and report generation engine 530 is triggered. The reports generated by report generation engine 530 may include a variety of information, including statistics related to the sensor data, metadata associated with the sensor data collection, the sensor data itself, and analysis information generated by the analysis engine 540.

The portal backend engine 528 may send and receive messages with the hub devices via communication unit 504. The portal backend engine 528 may provide an API for the clinician frontend engine 536, such that a user of the clinician frontend engine 536 may view subject information, sensor data, and report data generated by report generation engine 530.

The portal backend engine 528 may authenticate hub devices via public key cryptography. The portal backend engine 528 may receive messages and requests from the hub devices, may check permissions of a requesting hub device, and may provide a response to the hub device based on the message or request via communication unit 504. These messages or requests may include configuration requests and messages indicating the completion of a sleep session by a subject.

The portal backend engine 528 may receive manual scoring requests from the scoring engine 534 and may store them in the database 524. The portal backend engine 528 may receive analysis information for a sleep session from analysis engine 540 and may store the analysis information in database 524. The portal backend engine 528 may trigger a report to be generated by report generation engine 530 based on analysis information received from the analysis engine 540 or stored in database 524.

The portal backend engine 528 may enqueue requests for analysis including sensor data and metadata in a processing queue. The portal backend engine 528 may receive notifications from the analysis engine 540 once analysis of a request in the processing queue is competed.

The clinician frontend engine 536 may be an interface that allows for the review of information stored in database 524 or storage system 532, including subject reports generated by report generation engine 530, analysis engine 540, sensor data, metadata, manual scoring data, or any other data required by the clinician to review the collected sleep sensor data and related analysis and reporting.

ii. Methods for Breathing Signal Analysis and Event Detection

Referring next to FIG. 6 there is shown a method diagram 600 of an example breathing signal analysis method in accordance with one or more embodiments. Method 600 may be a computer-implemented method for breathing signal analysis for characterizing at least one recorded signal as indicative of one of Obstructive Sleep Apnea (OSA) and Central Sleep Apnea (CSA). The method 600 may be performed at hub backend 234 (see FIG. 2B) or 428 (see FIG. 4) on the collected sensor data from the patch device. The method 600 may be performed at portal backend engine 258 (see FIG. 2B) or 528 (see FIG. 5) on the collected sensor data from the patch device. The method 600 may be performed at analysis engine 268 (see FIG. 2B) or 540 (see FIG. 5) on the collected sensor data from the patch device.

At 602, an audio signal and a corresponding accelerometer signal are received at a processor.

At 604, a frequency domain representation of the audio signal is determined at the processor.

At 606, at least one frequency interval component of the frequency domain representation of the audio signal is sorted at the processor into at least one corresponding frequency bin.

In some cases, the corresponding frequency bins may be centered $$\text{around } bin[n] = \frac{n * Fs}{num(DFTpoints)}.$$

At 608, a signal-to-noise ratio (SNR) signal is determined by the processor for each frequency bin during a candidate time period.

In some cases, the SNR for each frequency bin may be determined based on the signal content. The signal content determined from the frequency bin may be the "total signal energy", and a corresponding value for "total noise energy" may also be determined. The SNR may be determined as $$10\log 10\left(\frac{\text{total signal energy}}{\text{total noise } energ}\right).$$

At 610, an indication of an OSA event or a CSA event based on the SNR signal for each frequency bin during the candidate time period is determined using a machine learning model at the processor, the audio signal for the candidate time period, and the accelerometer signal for the candidate time period.

In some cases, the method may further comprise determining a local minima for each frequency bin during the candidate time period; and wherein the determining the SNR signal for each frequency bin comprises performing a minima controlled recursive averaging of the local minima for each frequency bin with a corresponding local minima for each frequency bin in at least one preceding time period. The recursive averaging for each frequency bin may determine a statistical averaged signal such as the one shown in FIG. 9 (or may use another statistical determination).

In some cases, the minima controlled recursive averaging may comprise Cohen's method. Cohen's method is useful for identifying speech in audio. The present recursive averaging may differ from Cohen's method since here a longer search window is used for finding minima.

In some cases, an SNR may be determined by performing spectral subtraction and setting a minimum value of lambda*signal[k].

Figure 12A:
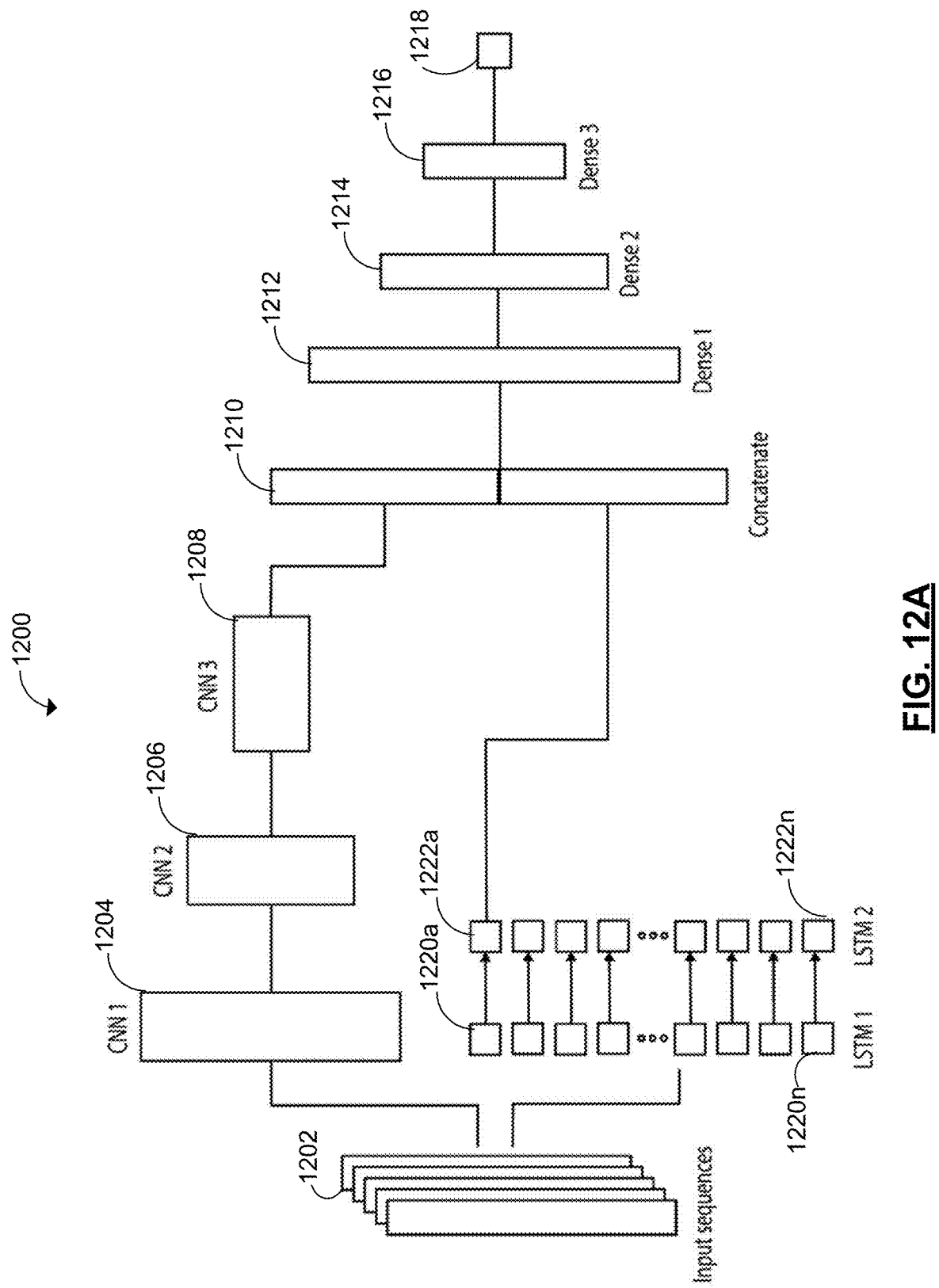
FIG. 12A shows an example event detection model in accordance with one or more embodiments.
Figure 12C:
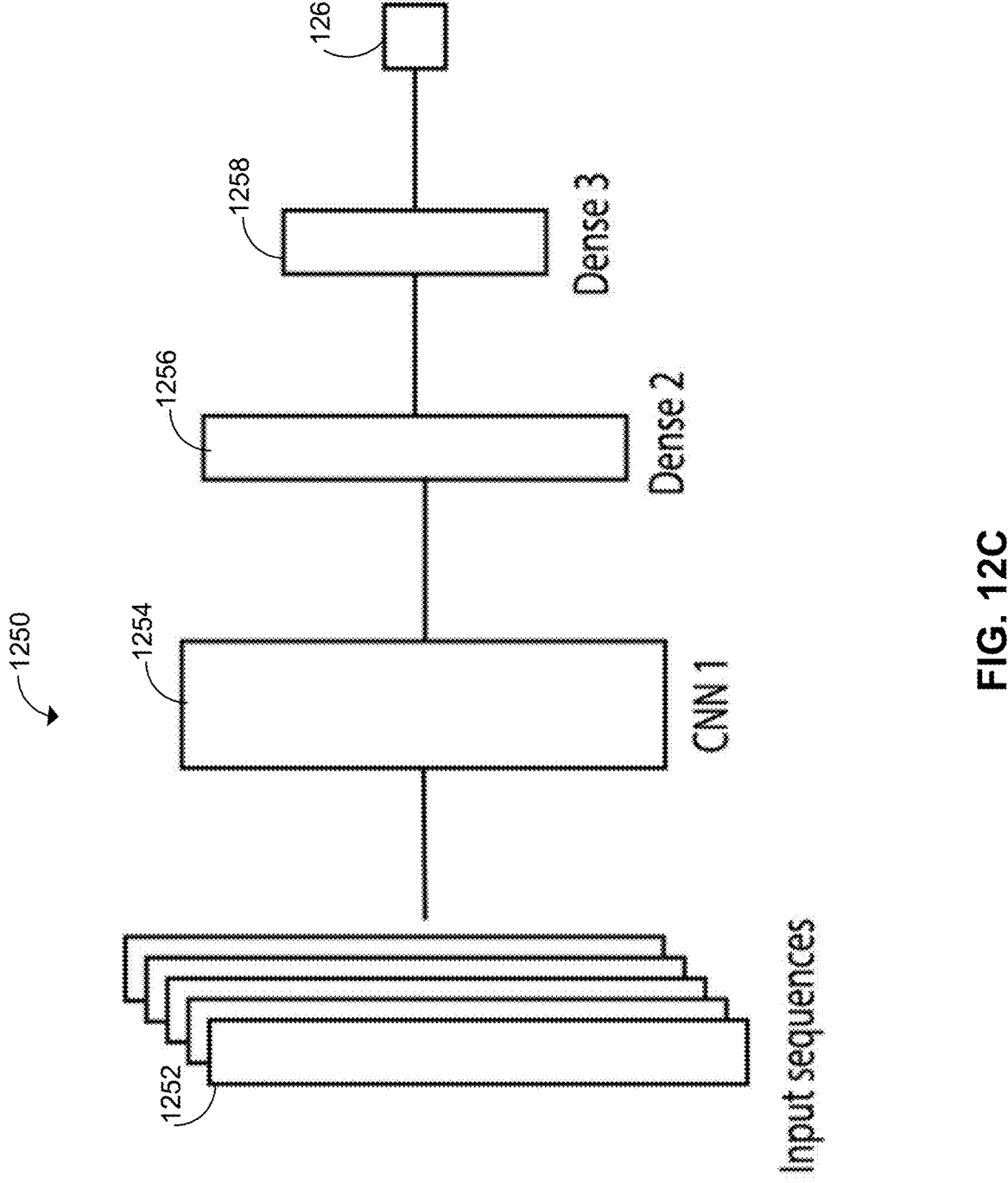
FIG. 12C shows another example event detection model in accordance with one or more embodiments.
Figure 12D:
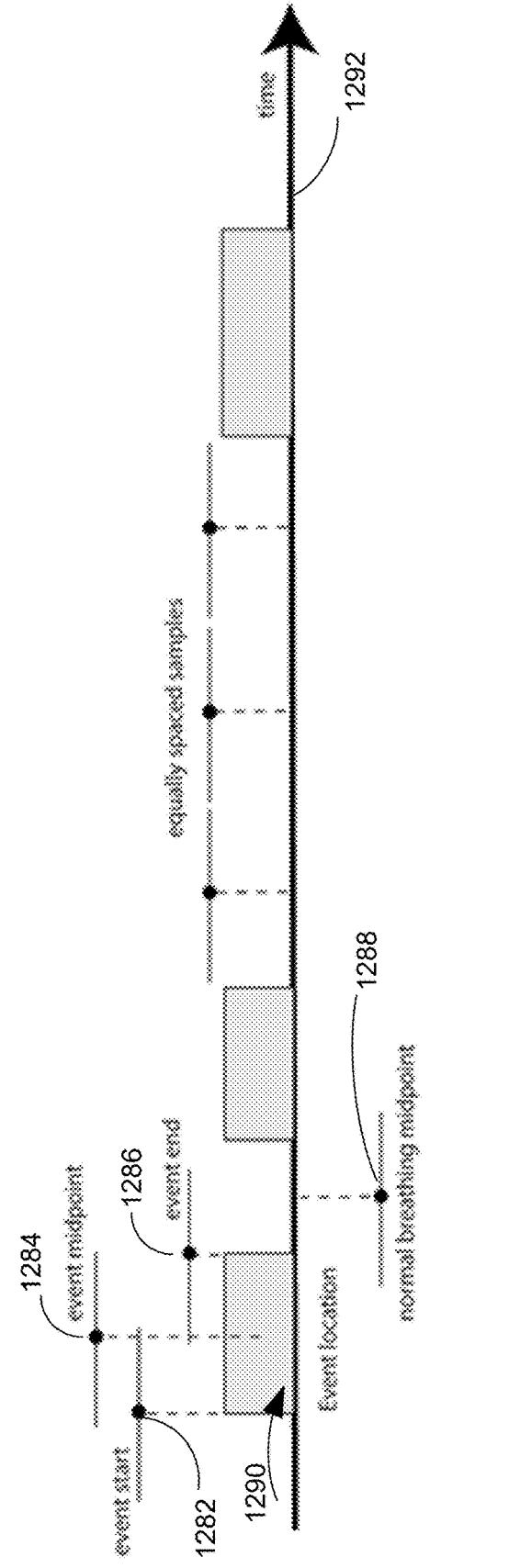
FIG. 12D shows a sliding window sampling technique of FIG. 12C in accordance with one or more embodiments.

In some cases, the candidate time period may comprise a sliding window and the indication of the OSA event or CSA event is determined for a plurality of time periods (as described in further detail in FIGS. 12B and 12D).

In some cases, the sliding window may be 61 seconds long.

In some cases, the method may further comprise applying, at the processor, a band-pass filter to the audio signal, the band-pass filter allowing frequencies between 200 Hz and 4000 Hz.

In some cases, the method may further comprise outputting, at a user interface device in communication with the processor, the indication of the OSA event or the CSA event.

In some cases, the method may further comprise determining, at the processor, a Hilbert envelope of the accelerometer signal; normalizing, at the processor, the accelerometer signal using the Hilbert envelope. For example, this may assume a signal in the form A(t)sin (omega (t)+c), and the normalization may be performed using the Hilbert envelope to remove an envelope (by setting A(t)=1). The spectral peak in a range of frequencies may be identified and this frequency/phase may model the breathing signal (this may also include some harmonics). The root mean squared error of the envelope-normalized signal may be compared to a sinusoidal model to determine a breathing signal.

In some cases, a sinusoidal breathing signal may be determined from the accelerometer signal. To do so, the sinusoidal model may be created by taking a Fourier transform of one axis (for example, the x-axis) of the accelerometer signal, and then finding a peak within the range of possible breathing frequencies. The Fourier coefficients around this peak and around a number of harmonics (integer multiples of the frequency of the chosen peak) may be kept and the rest are set to zero. Then an Inverse FFT may be performed, with phase information being preserved. Amplitude between the sinusoidal model and the accelerometer segment being considered may be matched in amplitude by first multiplying by the inverse of the Hilbert envelope.

Figures 10, 11:
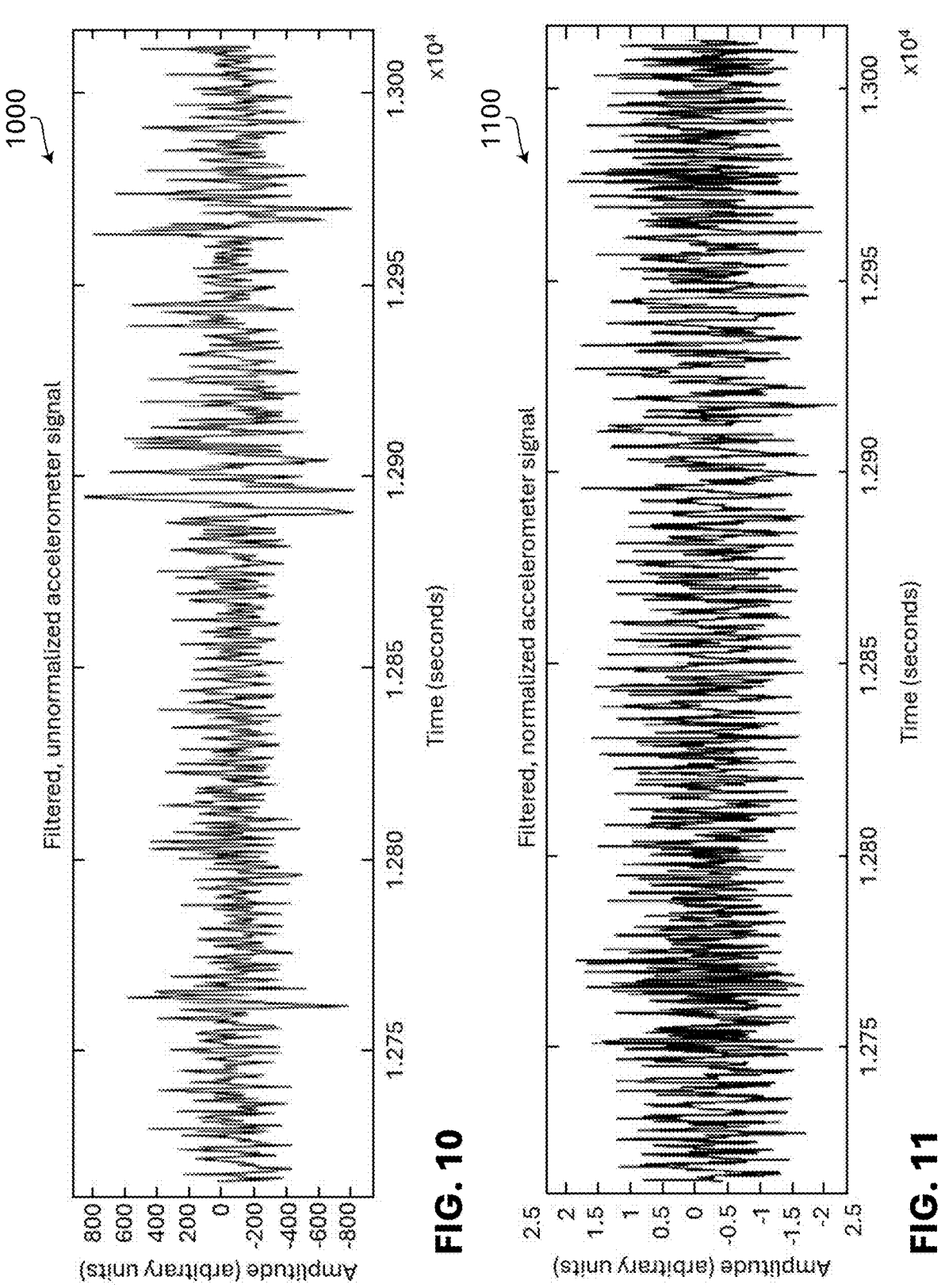
FIG. 10 shows an example accelerometer signal in accordance with one or more embodiments.
FIG. 11 shows an example normalized accelerometer signal in accordance with one or more embodiments.

The determined accelerometer signal may be the one shown in FIG. 10. The determining, using the machine learning model at the processor, the indication of the OSA event or the CSA event may further be based upon the normalized accelerometer signal. For example, the normalized accelerometer signal may be the one shown in FIG. 11.

In some cases, the method may further comprise determining, at the processor, a spectral peak of the accelerometer signal; generating, at the processor, a breathing signal based on a frequency and a phase of the spectral peak; and wherein the determining, using the machine learning model at the processor, the indication of the OSA event or the CSA event is further based upon the breathing signal.

In some cases, the breathing signal may comprise a sinusoidal breathing signal model.

In some cases, the method may further comprise receiving, at the processor, an oximeter signal; and wherein the determining, using the machine learning model at the processor, the indication of the OSA event or the CSA event is further based on the oximeter signal for the candidate time period.

Referring next to FIG. 7A there is shown a method diagram 700 of an example breathing event detection method in accordance with one or more embodiments. The method 700 may be a computer-implemented method for event detection of Obstructive Sleep Apnea (OSA) events and Central Sleep Apnea (CSA) events from recorded breath sounds of a subject. The method 700 may be performed at hub backend 234 (see FIG. 2B) or 428 (see FIG. 4) on the collected sensor data from the patch device. The method 700 may be performed at analysis engine 268 (see FIG. 2B) or 540 (see FIG. 5) on the collected sensor data from the patch device. The method 700 may be performed by a cloud service, or a hardware device separate from the other parts of the server infrastructure.

At 702, an audio signal for a candidate time period is received at a processor, and a corresponding accelerometer signal for the candidate time period is also received.

At 704, an input sequence is determined at the processor for a machine learning model based on a signal-to-noise ratio signal for a plurality of frequency bins of the audio signal for the candidate time period, the audio signal for the candidate time period, and the accelerometer signal for the candidate time period.

At 706, an occurrence of an OSA event or a CSA event is determined using the machine learning model at the processor based on the signal-to-noise ratio signal for each frequency bin of the candidate time periods, the audio signal for the candidate time period, and the accelerometer signal for the candidate time period.

The determining the occurrence of the OSA or CSA event may include determining one or more features of the audio signal, the accelerometer signal, and optionally, an oximetry signal, as described in FIG. 7B.

In some cases, the machine learning model may comprise: at least one neural network; at least one recurrent neural network; at least one dense layer; wherein the at least one neural network and the at least one recurrent neural network may receive the input sequence; wherein the at least one dense layer may receive a concatenated output of the at least one neural network and the at least one recurrent neural network; and wherein the occurrence of an OSA event or a CSA event may be determined based on the output of the at least one dense layer.

In some cases, the at least one neural network may comprise at least one convolutional neural network.

In some cases, the at least one recurrent neural network may comprise at least one long short-term memory (LSTM).

In some cases, the method may further comprise outputting, at an output device in communication with the processor, the occurrence of the OSA event or the CSA event.

In some cases, the method may further comprise receiving, at the processor, an oximetry signal for the candidate time period; and wherein the input sequence for the machine learning model is further based upon the oximetry signal for the candidate time period.

In some cases, the method may further comprise determining, at the processor, a sleep state of the subject, the sleep state determined using the audio signal and the accelerometer signal based on a statistical sleep model; and wherein the occurrence of an OSA event or a CSA event is determined based on the sleep state of the subject.

iii. Method for Breathing Event Inference and Prediction

Referring next to FIG. 7B there is shown an example method 750 of breathing event inference and prediction in accordance with one or more embodiments. The inference and prediction method 750 may be performed by automatic analysis engine 268 (see FIG. 2B), or 540 (see FIG. 5).

The inference and prediction method 750 may include receiving sensor data 752, stitching and converting the received sensor data 754 to generate processed recordings 756. The processed recordings 756 may have one or more features extracted 758 and stored 760.

The stitch and convert 754 may be used to stitch the recordings together if there are dropouts during a recording, and where pieces of the recordings are stored in file chunks and must be stitched back together for analysis.

The feature extraction 758 can include those described in FIGS. 12A, 12C, and 13.

The feature extraction 758 may include determining audio features such as Signal-to-Noise (SNR) ratio statistics, including but not limited to interquartile range (IQR), 95th percentile, kurtosis of SNR, time above an amplitude threshold such as −20 dB. The SNR ratio statistics may include an SNR determined using Cohen's method, as described herein. The SNR determined using Cohen's method may include determining noise and signal power every 100 ms, sliding a window over the calculated SNR values and calculating IQR where the SNR value is greater than −20 dB. The feature extraction 758 may further include determining a plurality of mel-frequency cepstrum coefficients (MFCC). The MFCC coefficients may be a spectrogram determined based on an FFT. The MFCCs may be determined using a sliding window for periods where the SNR is greater than −20 dB. A high pass filter may further be used in audio feature extraction.

The feature extraction 758 may further include determining audio features from audio data for the sleep detection model 768. This may include the SNR signals (as described above), kurtosis and 95th percentile may be calculated along with IQR, and the MFCC features (as described above).

The feature extraction 758 may further include determining position-based accelerometer features such as median phi and theta per 10 second window. The feature extraction 758 for accelerometer features may include the use of a low-pass filter or a band-pass filter. The feature extraction 758 may further include determining accelerometer features such as determining an RMS value of a moving average of each axis, including the x, y, and z axes. The feature extraction 758 may further include determining accelerometer features such as absolute rotation and pitch angles of accelerometer, the 95th percentile minus 5th percentile of the rotation angle of the accelerometer, the root-mean-squared (RMS) of each of the x, y, z axes after a high pass filter (HPF) with cutoff of 1.5 Hz. The accelerometer training data may have each subject's data normalized by 97.5th and 2.5th percentiles.

The feature extraction 758 may further include determining accelerometer features from accelerometer data for the sleep detection model 768. This may include using a high pass filter or a low pass filter for the accelerometer data. The accelerometer features from the accelerometer data for the sleep detection model 768 may include RMS values using upper/lower percentiles for each of the x, y, and z axis. This may further include a 5th to 95th percentile value of theta, an RMS change value of theta, and an RMS change value of phi.

The feature extraction 758 may further include determining oximeter features for a subject. This may include determining an absolute change by measuring troughs found using peak detection, and merging periods of oxygen level drops that are close to one another or too small. The oximeter values generated using feature extraction 758 may be represented using repeated values where a drop is located, i.e. [0, 0, 0, 5, 5, 5, 5, . . . , 5, 5, 0, 0, 0, 3, 3, 3 . . . ]. The feature extraction 758 for oximeter data may include determining a slope of oximeter data 1302 using the determined drops in the start of trough to it's nadir.

The feature extraction 758 may further include a portion of the SNR audio signal, the sinusoidal breathing signal determined from the accelerometer, statistics of the SNR signal, changes in the oximeter signal level, features derived from the rotation angles of the accelerometer signal, features derived from the activity (including the RMS) of the accelerometer signal.

The feature extraction 758 may generate features from the processed sensor data 756 and stored in feature database 760. Feature extraction may be the process of taking raw sensor data (oximetry, audio, accelerometry) and creating k new time series (features), i.e., $f_1[n]$, $f_2[n]$, . . . $f_k[n]$, to a) normalize the differences in sample rates between the three sources of sensor data and b) convert raw sensor data into feature sets which may be a more compact and informative representation for the model.

The feature processing 762 may prepare input sequences for the first event model 764, the second event model 766, the sleep detection model 768, and the effort/flow estimation model 770. The feature processing 762 may involve interpolation, feature normalization, and outlier removal of the processed recordings 756.

The first event model 764 may be the model 1200 in FIG. 12A and may operate to identify breathing events based on the input sensor data and associated features. The first event model 764 may predict events occurring within the sensor data 752 once per second.

The second event model 766 may be the model 1250 in FIG. 12C and may operate to identify breathing events based on the input sensor data and associated features. The second event model 766 may predict events occurring within the sensor data 752 once per second.

The sleep detection model 768 may be used to identify portions of sensor data when the subject is asleep and portions of sensor data when the subject is awake. For determinations of metrics such as an Apnea Hypopnea Index (AHI), the formula for determination of AHI may be the number of respiratory events/total sleep time. Without an accurate measure of both quantities (i.e., the number of apnea and hypopnea events and the length of sleep), generated AHI values will be less accurate if the calculations are made over time periods including sensor data from when the subject is awake. The sleep detection model 768 may predict a sleep state of a subject for a thirty second window. The sleep detection model 768 may be the reported detection probability of the model, which may be defined as the mean predicted class probabilities of the trees in the forest. The class probability of a single tree may be the fraction of samples of the same class in a leaf.

The effort/flow estimation model 770 may estimate the respiratory effort or airflow of a subject.

Once predictions are completed by the first event model 764, the second event model 766, the sleep detection model 768, and the flow estimation model 770, the predictions may be combined 772 to generate a final output including one or more sleep events 774, a sleep state 776, and a flow surrogate 778.

The combination of the predictions 772 may include the use of a logistic regression model to obtain the final output, and a set of heuristic rules may be applied to determine when the patient is awake vs. when the patient is asleep (sleep state 776) and breathing normally vs. when the patient is asleep and having a respiratory event (events 774).

The "combine predictions" step 772 may use a combination of the logistic regression and heuristic rules to combine the model outputs into the final output.

To achieve the final output, the output of the sleep detection model 768 is combined with the output of the logistic regression (LR) model 772 using the following parameters. The LR model 772 may combine the outputs of the two event models 764 and 766 and the sleep detection model 768 to determine an aggregate estimate of event probability at each time index.

The output of this LR model 772 may combine the output of the event models 764 and 766, and the sleep model 768, using heuristics, to come up with the final set of outputs 774, 776, and 778.

The combination of the outputs 772 may include some initial processing, including comparing the output of the LR model to an event_thresholds parameter to determine a binary time series. The initial processing may further comprise merging segments of output that are closer than the parameter min_dur_comb. The initial processing may further include removing segments that are shorter in length than the min_dur_remove parameter.

The wake_thresholds parameter may be one or more thresholds to process predicted wake probabilities and may contain two keys: min and max. The wake_thresholds parameter may define the minimum and maximum predicted probabilities of wake. In case the probability may be between minimum and maximum, a wake may be established in case there isn't an event at the same location. If the predicted probability is lower than the minimum, there may not be a wake at the location. In case the wake probability is higher than the maximum, wake may be established at this location and any event detected at the same position is removed.

The min_dur_comb parameter may be a minimum gap between events to be merged.

The min_dur_remove parameter may be a minimum duration of an event to be removed.

The event_thresholds parameter may be a probability threshold for the model to be processed. The event_thresholds parameter may define at each sample whether there is an event occurring.

The combination of model outputs 772 using an LR model may proceed as follows. The value n may be the index of the epoch (or time window), for epochs when n=0 to N−1, where N is the total number of epochs. The value k may be the index of the detected respiratory events, k=0 to K−1, where K may be the total number of identified respiratory events remaining after initial processing. The value $p_w[n]$ may be the probability of wake for time index n. The value W[n] may be an array containing the sleep/wake prediction, where 1 represents wake and 0 represents sleep. The value M[k] may be an array containing the midpoint, in seconds, of the $k^{th}$ event.

To combine the model outputs 772, the first step may be to determine if there are events in the epoch, i.e., if there is one or more instances of events (based on the midpoint) within the epoch |{k|30(n+1)>M[k]>30n}|>0, |M|>k>0.

The next step may be to determine if there are events in the epoch and the wake threshold is met, i.e. If there are events AND wake_thresholds ['min']<$p_w[n]$ <wake_thresholds['max']) then W[n] may be set to 0 and the subject may be identified as asleep.

The next step may be to determine if there are events in the epoch and the wake threshold is exceeded, i.e. If there are events in the epoch AND wake_thresholds['max']<$p_w[n]$ then W[n] is set to 1 and the subject may be identified as awake. In the case where the subject is identified as awake, then events may be removed from M which occur during this epoch.

The next steps may be to identify if there are no events in the epoch, then W[n] is set to 1 if wake_thresholds['min'] <$p_w[n]$ and set to 0 otherwise.

The stream of probabilities for events 774 and wakes 776 may be processed according to some of the above parameters.

Figure 8:
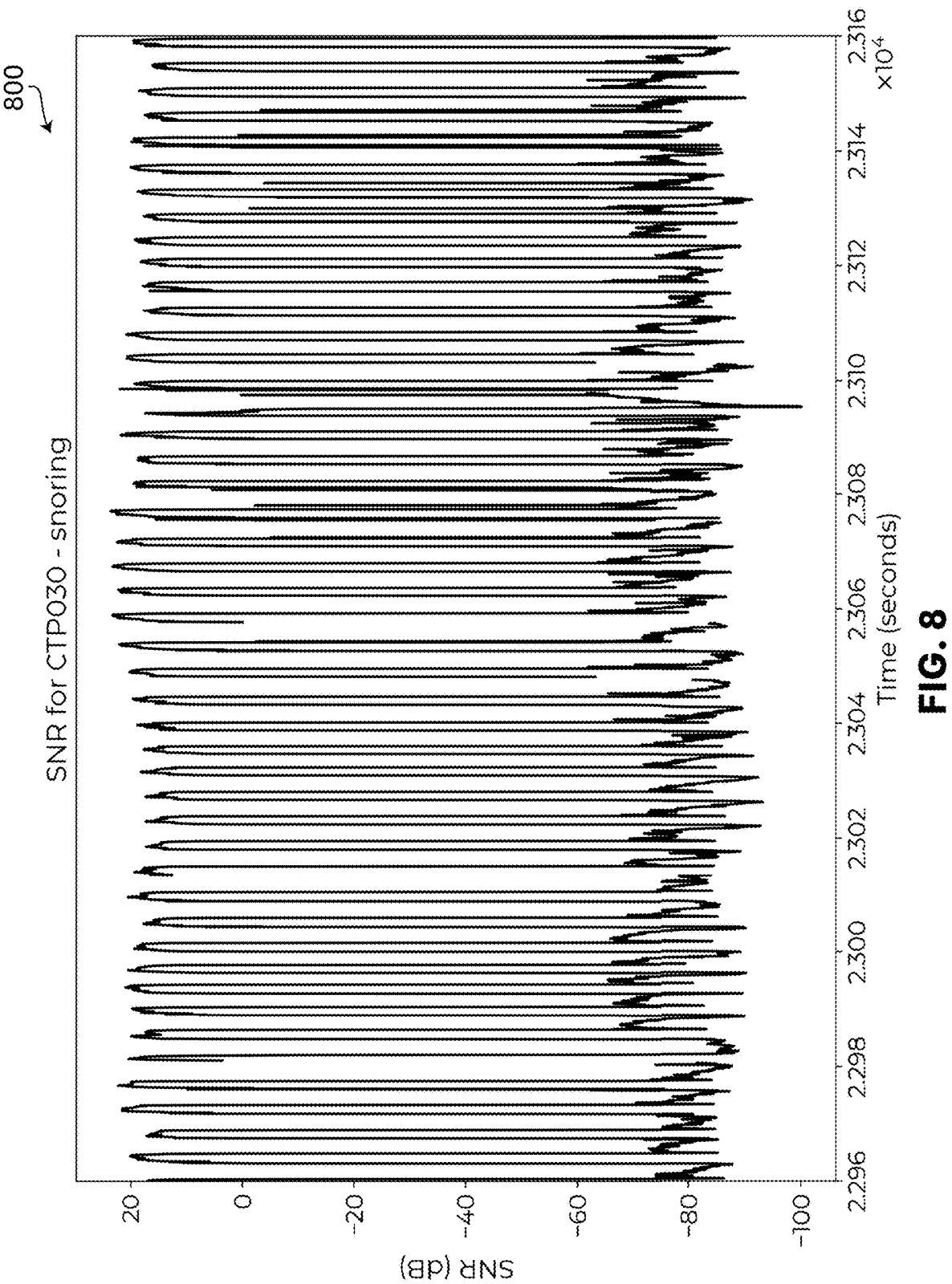
FIG. 8 shows an example Signal-to-Noise-Ratio (SNR) signal in accordance with one or more embodiments.

Referring next to FIG. 8 there is shown a signal diagram 800 of an example signal-to-noise-ratio (SNR) signal in accordance with one or more embodiments. The signal to noise ratio signal 800 may be determined as part of the signal analysis at one of the hub backend 234 (see FIG. 2B) or 428 (see FIG. 4), portal backend 258 (see FIG. 2B) or 528 (see FIG. 5), or analysis engine 268 (see FIG. 2B) or 540 (see FIG. 5).

Figure 9:
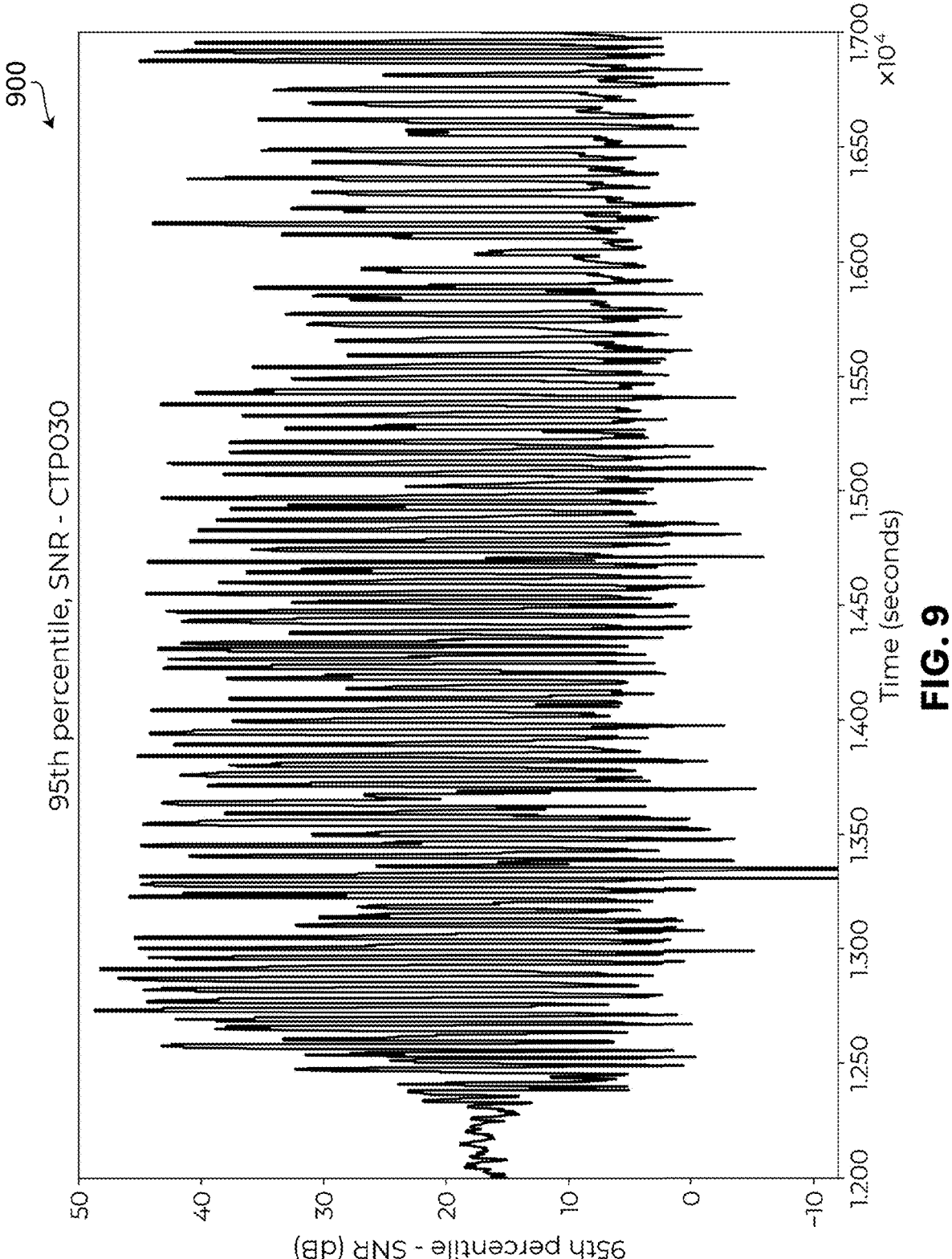
FIG. 9 shows an example $95^{th}$ percentile SNR signal in accordance with one or more embodiments.

Referring next to FIG. 9 there is shown another signal diagram 900 of an example 95th SNR signal in accordance with one or more embodiments. The signal 900 may be determined as part of the signal analysis at one of the hub backend 234 (see FIG. 2B) or 428 (see FIG. 4), portal backend 258 (see FIG. 2B) or 528 (see FIG. 5), or analysis engine 268 (see FIG. 2B) or 540 (see FIG. 5).

Referring next to FIG. 10 there is shown another signal diagram 1000 of an example accelerometer signal in accordance with one or more embodiments. The signal 1000 may be determined as part of the signal analysis at one of the hub backend 234 (see FIG. 2B) or 428 (see FIG. 4), portal backend 258 (see FIG. 2B) or 528 (see FIG. 5), or analysis engine 268 (see FIG. 2B) or 540 (see FIG. 5).

Referring next to FIG. 11 there is shown another signal diagram 1100 of an example normalized accelerometer signal in accordance with one or more embodiments. The signal 1100 may be determined as part of the signal analysis at one of the hub backend 234 (see FIG. 2B) or 428 (see FIG. 4), portal backend 258 (see FIG. 2B) or 528 (see FIG. 5), or analysis engine 268 (see FIG. 2B) or 540 (see FIG. 5).

iv. First Event Detection Model

Referring next to FIG. 12A there is shown a model diagram 1200 of an example event detection model in accordance with one or more embodiments. The model 1200 may be used by analysis engine 268 (see FIG. 2B) or 540 (see FIG. 5) to identify an event in a portion of sensor data that is indicative of OSA or CSA.

The event detection model 1200 may refer to model 764 in FIG. 7B. The event detection model may have a plurality of input sequences 1202 which may include portions of the collected sensor data. The input sequences 1202 may be sensor data such as oximeter data, accelerometer data, and audio data that may be combined. The input sequences 1202 may further include inputs such as a portion of the SNR audio signal, the sinusoidal breathing signal determined from the accelerometer, statistics of the SNR signal, changes in the oximeter signal level, features derived from the rotation angles of the accelerometer signal, features derived from the activity (including the RMS) of the accelerometer signal, or other signals or features herein (for example as described in 758 in FIG. 7B and 1308 in FIG. 13A). The input sequences may be for a particular time window in the analysis, and the data may be for a fixed time frame. The event detection model 1200 may include at least one neural network, such as first neural network 1204, second neural network 1206, and third neural network 1208. While three neural networks 1204, 1206, 1208 are shown, it is understood that any number of neural networks may be used. The event detection model 1200 may include a plurality of LSTMs 1220 and 1222.

The first neural network 1204, a second neural network 1206, and a third neural network 1208 may be in series, with the input of the first neural network 1204 receiving the input sequence 1202, the input of the second neural network 1206 receiving the output of the first neural network 1204, and the input of the third neural network 1208 receiving the output of the second neural network 1206.

The plurality of LSTMs may be in parallel with the at least one neural network.

The plurality of LSTMs may be in series as shown, i.e., the output of LSTM 1220a may be input for LSTM 1222a, the output of LSTM 1220b may be input for LSTM 1222b, the output of LSTM 1220n may be input for LSTM 1222n, etc.

A concatenation layer 1210 may receive the output from the plurality of LSTMs 1222 and the third neural network 1208.

At least one dense layer 1212, 1214, and 1216 may receive the output of the concatenation layer 1210. This may include a first dense layer 1212, a second dense layer 1214 and a third dense layer 1216. An output 1218 may be provided based on the at least one dense layer 1212, 1214 and 1216 for the given input sequence 1202 indicating a predictive result of an indication of a CSA or OSA event associated with the time window of the sensor data corresponding to a particular input sequence 1202. The output prediction may be received by the portal backend 258 (see FIG. 2B) or 528 (see FIG. 5) and stored in one or more databases 524 in association with the corresponding input sequence 1202 in the sensor data.

An event model such as model 1200 may incorporate two different approaches to identify events. The first event model may be a statistical mode such as a Convolutional Neural Net (with LSTM in parallel) as shown. The CNN/LSTM (DNNV1) may be trained based on samples collected by a sliding window of 61 seconds (input sequence).

Referring next to FIG. 12B there is shown a sliding window sampling technique diagram 1230 in accordance with one or more embodiments. As previously described, signal analysis may be performed on one or more of the audio signals, the accelerometer signal, and the oximeter signal. This may include analyzing a time-indexed 1232 set of input features 1234 in the signal using a sliding window 1236. For example, for a given time period of analysis, the candidate time period may comprise a sliding window and the indication of the OSA event or CSA event may be determined for a plurality of time periods. The input features, including the audio signal, accelerometer signal, and the oximeter signal and any determined features such as the SNR, may be analyzed using a sliding window. For example, a 61 second sliding window may be used, and an event detection method herein may be performed for each 61 second window in order to identify sleep apnea events. The windows may be subsampled, and every $5^{th}$ sliding window may be used (stride of 5).

v. Second Event Detection Model

Referring next to FIG. 12C there is shown a model diagram 1250 of another example event detection model in accordance with one or more embodiments. The model 1250 may be used by analysis engine 268 (see FIG. 2B) or 540 (see FIG. 5) to identify an event in a portion of sensor data that is indicative of OSA or CSA. The model diagram 1250 may be for the model 766 (see FIG. 7B).

The model diagram 1250 may be trained using a sliding window of 61 seconds. The training of model 1250 may include subsampling input sequences. This may include respiratory event segments with three samples: an event start, an event midpoint, and an event end. This may further include normal breathing segments: if smaller than 61 seconds, the midpoint of this segment may be sampled. Otherwise, sampling may occur at equally spaced intervals.

The model diagram 1250 may receive a plurality of input sequences 1252. The first neural network 1254 may receive the input sequences 1252 as input.

The first dense layer 1256 may receive the output of the first neural network 1254. The second dense layer 1258 may receive the output of the first dense layer 1256. The output 1260 may be the output of the second dense layer 1258.

The first neural network 1254 may be a convolutional neural network.

The model diagram 1250 may be a deep learning model trained over samples picked from event locations (start, midpoint, end) and sampled normal breathing in an equally spaced manner (see FIG. 12D). The model diagram 1250 may use the output of the first neural network 1254 and optionally one or more LSTMs as inputs, concatenate them, and then use several dense layers.

The input sequences 1252 of event detection model 1250 may include portions of the collected sensor data. The input sequences 1252 may be sensor data such as oximeter data, accelerometer data, and audio data that may be combined. The input sequences 1252 may further include inputs such as a portion of the SNR audio signal, the sinusoidal breathing signal determined from the accelerometer, statistics of the SNR signal, changes in the oximeter signal level, features derived from the rotation angles of the accelerometer signal, features derived from the activity (including the RMS) of the accelerometer signal, or other signals or features herein. The input sequences 1252 may be for a particular time window in the analysis, and the data may be for a fixed time frame.

Referring next to FIG. 12D there is shown a sampling technique diagram 1280 in accordance with one or more embodiments. The sampling technique 1280 may be performed to prepare training data for the model 1250 in FIG. 12C.

A user, for example, a user using manual scoring 270 (see FIG. 2B) may review sensor data from a sleep session of one or more individuals. The user may label or identify events for a training data set, including sleep sensor data collected over time axis 1292. This may include identifying an event 1290, having a start point 1282, a midpoint 1284, and an end point 1286. This may further include identifying a normal breathing portion 1288 of the sensor data along time axis 1292. This labelling may be used to determine a ground truth for the training dataset used to create the model.

vi. Sleep Detection Model

With reference to FIG. 7B, the sleep analysis for the sleep analysis model may begin by calculating some audio and accelerometer features from the collected sensor data. Assuming there are K features in total, this can involve calculating each over all N epochs, to give K times N feature values in total. For each epoch (time) index n, the feature values are defined as $f_1[n], f_2[n], \ldots, f_K[n], n=0 \ldots N$.

For inferring the sleep/wake status for epoch n, the input may consist of the features from indexes n–B, n–B+1, . . . , n–1, n, n+1, . . . , n+F–1, n+F, to give a total of (B+F+1) times K feature values. This may be a kind of "context", like what is done in wrist actigraphy.

The sleep detection model may be a Random Forest model, with M=30 trees. The probability output may be used as an input to the logistic regression model 772.

vii. Training of Models

Figure 13A:
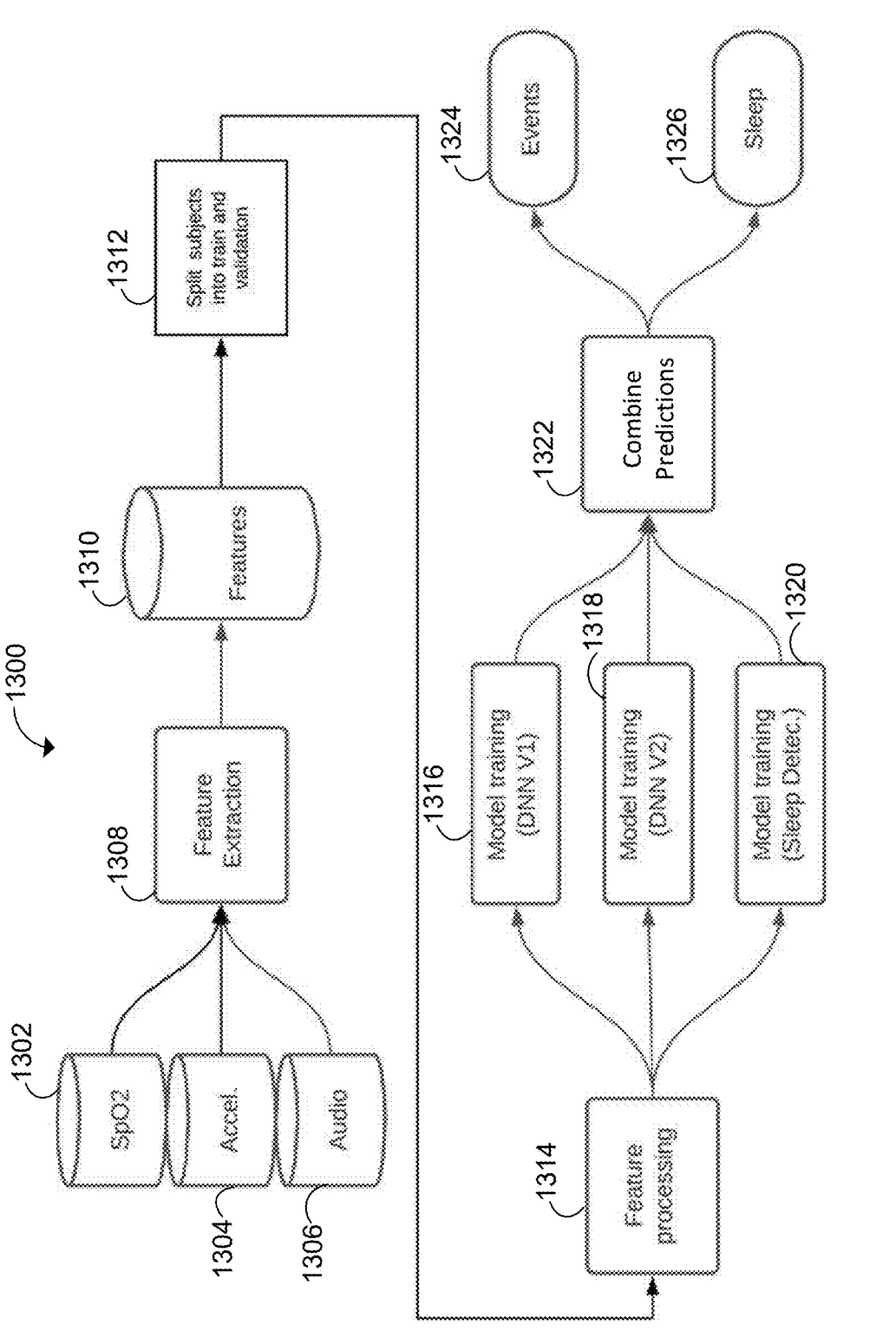
FIG. 13A shows an example event detection model training method in accordance with one or more embodiments.

Referring next to FIG. 13A there is shown a method diagram 1300 of an example event detection model training method in accordance with one or more embodiments. To determine a model for predicting OSA and CSA events in sensor data, the model training may be performed by the portal backend 258 (see FIG. 2B) or 528 (see FIG. 5), and the generated model may be stored in database 264.

The training data used, including oximeter training data 1302, accelerometer training data 1304, and audio training data 1306 may use clinician scored polysomnographic (PSG) data as labels. This may include data that is broken up into 30 second segments or windows. The scored PSG data may include oximetry data, audio data, and accelerometer data that has locations and types of apneas and hypopneas, scored continuously. The scored PSG data may further include sleep stage data (not shown), scored every 30 seconds. Each sleep stage value may be one of (REM, NREM1, NREM2, NREM3, Wake). Finally, the PSG data may include the locations of oxygen desaturations greater than or equal to 3%, often scored by the PSG software and vetted by the technician.

Some data preparation may be involved, including converting continuous event labels into discrete-time values. Further, labels for sleep state may be converted into a binary grouping, i.e., NREM(1, 2, 3) and REM may be converted to 'Sleep' and Wake may be converted to 'Wake'.

Feature extraction 1308 is performed on oximeter training data 1302, accelerometer training data 1304, and audio training data 1306 to generate and store features 1310 associated with training data. This may include a plurality of training sensor data records collected and scored according to the manual scoring interface 270 (see FIG. 2B). The feature extraction 1308 for oximeter training data 1302 may include determining drops in oximeter levels for a subject. This may include an absolute change by measuring troughs found using peak detection, and merging periods of oxygen level drops that are close to one another or too small. The oximeter values generated using feature extraction 1308 may be represented using repeated values where a drop is located, i.e. [0, 0, 0, 5, 5, 5, 5, . . . , 5, 5, 0, 0, 0, 3, 3, 3 . . . ]. The feature extraction 1308 for oximeter training data 1302 may include determining a slope of oximeter data 1302 using the determined drops in the troughs to the nadir.

The feature extraction 1308 may include determining audio features such as Signal-to-Noise (SNR) ratio statistics, including but not limited to interquartile range (IQR), 95th percentile, kurtosis of SNR, time above an amplitude threshold such as –20 dB. The SNR ratio statistics may include an SNR determined using Cohen's method, as described herein. The SNR determined using Cohen's method may include determining noise and signal power every 100 ms, sliding a window over the calculated SNR values and calculating IQR where the SNR value is greater than –20 dB. The feature extraction 1308 may further include determining a plurality of mel-frequency cepstrum coefficients (MFCC). The MFCC coefficients may be a spectrogram determined based on an FFT. The MFCCs may be determined using a sliding window for periods where the SNR is greater than –20 dB. A high pass filter may further be used in audio feature extraction.

The feature extraction 1308 may further include determining position-based accelerometer features such as median phi and theta per 10 second window. The feature extraction 1308 for accelerometer features may include the use of a low-pass filter or a band-pass filter. The feature extraction 1308 may further include determining accelerometer features such as determining an RMS value of a moving average of each axis, including the x, y, and z axes. The feature extraction 1308 may further include determining accelerometer features such as absolute rotation and pitch angles of accelerometer, the $95^{th}$ percentile minus $5^{th}$ percentile of the rotation angle of the accelerometer, the root-mean-squared (RMS) of each of the x, y, z axes after a high pass filter (HPF) with cutoff of 1.5 Hz. The accelerometer training data may have each subject's data normalized by $97.5^{th}$ and $2.5^{th}$ percentiles.

The feature extraction 1308 may further include determining audio features from audio data 1306 for the sleep detection model 1320. This may include the SNR signals (as described above), kurtosis and $95^{th}$ percentile values may be calculated along with IQR, and the MFCC features (as described above).

The feature extraction 1308 may further include determining accelerometer features from accelerometer data 1304 for the sleep detection model 1320. This may include using a high pass filter or a low pass filter for the accelerometer data 1304. The accelerometer features from the accelerometer data 1304 for the sleep detection model may include RMS values using upper/lower percentiles for each of the x, y, and z axis. This may further include a $5^{th}$ to $95^{th}$ percentile value of theta, an RMS change value of theta, and an RMS change value of phi.

At 1312, the training dataset including the determined features 1310 and the training data (including oximeter training data 1302, accelerometer training data 1304, and audio training data 1306) may be split into a validation dataset and a training dataset. The training dataset may be used to determine a model, and the validation dataset may be used to evaluate the model. The split subject step 1312 may comprise a stratified split of subjects according to their AHI (apnea-hypopnea index) severity (such as into 4 different groups) so each training/validation dataset pair has approximately the same AHI distribution.

At 1314, feature processing may be performed. The feature processing may comprise a normalization of the plurality of feature values, a removal of outliers of the plurality of feature values, and/or an interpolation of the plurality of feature values.

At 1316, model training may be conducted. This may include determining a sleep detection model using a random forest model training method 1320. This may include determining a first deep neural network 1316 and determining a second deep neural network 1318. The random forest training method 1320 may be one of those as known. The deep learning training method 1316 and 1318 may be a deep learning training method as known.

The sleep model training 1320 may use the converted sleep state labels in the training data. The training 1320 may determine context, i.e. For each epoch (time) index n of each training data sample, the feature values may be defined as $F[n]=[f_1[n], f_2[n], \ldots, f_K[n]], n=0 \ldots N-1, k=1 \ldots K$. To represent the sleep state at time index n, a new vector G may be created such that: $G[n]=[F[n-B], F[n-B+1], \ldots, F[n-1], F[n], F[n+1], \ldots, F[n+F-1], F[n+F]]$, where B, F>0. The G vectors may then be used to train a model to predict sleep state probabilities.

The sleep model training 1320 may generate a random forest model. This may involve tree bagging using feature subsets, and a random forest model that may have T=30 trees.

In some cases, predictions may be combined 1322 to determine the output of the prediction models (see FIGS. 12A and 12D). After training, the first event model 1316 and the second event model 1318 and the sleep detection model 1320, it may be necessary to consolidate or combine 1322 the final prediction into one prediction of asleep/awake or the presence of an event for the entire sensor data portion (such as the window, or alternatively, for the entire recording). This may involve training a logistic regression model.

This may be done by combining the probabilities from the event models. To do so, a logistic regression model may be trained using the output of cross-validation on training data to avoid overfitting. The inputs to the logistic regression may be the outputs of the other three models (the first event model 1316, the second event model 1318, and the sleep model 1320). The output of the sleep model 1320 may be upsampled by an upscaling factor (for example, upscaling by 30) to match the output rate of the first event model 1316 and the second event model 1318.

The first deep neural network, the second deep neural network, and the sleep detection model may be trained using the training dataset and evaluated based on the validation dataset.

The generated model, including the first neural network, the second neural network, and the sleep detection model may be used to predict events 1324 associated with the subject (for example, OSA and CSA events) in sensor data, as well as an awake/asleep state of the subject 1326.

The method for evaluating the generated first deep neural network, second deep neural network, and sleep detection model is described in further detail in FIG. 14.

Referring next to FIG. 13B there is shown another method diagram 1350 of an example event detection model training method in accordance with one or more embodiments.

At 1352, training data comprising a plurality of audio signals and a plurality of accelerometer signals corresponding to the plurality of audio signals is received.

At 1354, extracting a plurality of feature values from the training data, the plurality of feature values corresponding to a plurality of predetermined features.

At 1356, training the at least one machine learning model for event detection of Obstructive Sleep Apnea (OSA) events and Central Sleep Apnea (CSA) events from recorded breath sounds based on the plurality of feature values.

In some cases, the method may further comprise: wherein the at least one machine learning model may comprise: at least one neural network; at least one recurrent neural network; and at least one dense layer, and wherein the training the machine learning model may further comprise: training, at the processor, the at least one neural network based on the plurality of feature values; training, at the processor, the at least one recurrent neural network based on the plurality of feature values; and training, at the processor, the at least one dense layer based on the plurality of feature values.

In some cases, the method may further comprise processing, at the processor, the plurality of feature values corresponding to the plurality of predetermined features, wherein the feature processing comprises at least one selected from the group of a normalization of the plurality of feature values, a removal of outliers of the plurality of feature values, and an interpolation of the plurality of feature values.

In some cases, the training data may further comprise a plurality of oximetry signals.

In some cases, the training data may further comprise a plurality of signal-to-noise ratio signals for a corresponding plurality of frequency bins for each audio signal in the plurality of audio signals in the training data.

In some cases, the training data may further comprise a plurality of breathing signals corresponding to the plurality of accelerometer signals.

In some cases, the method may further comprise wherein the at least one machine learning model further comprises a statistical sleep model for predicting a sleep state of a subject; determining, at the processor, a plurality of sleep feature values corresponding to a plurality of sleep features; and training, at the processor, the statistical sleep model based on the plurality of sleep feature values.

In some cases, the plurality of sleep features may comprise at least one selected from the group of an audio signal-to-noise ratio signal statistic, an audio signal MFCC coefficient, an accelerometer signal absolute rotation angle and pitch angle, and an accelerometer signal statistic.

viii. Effort/Flow Estimation Models

Referring briefly back to FIG. 7B, the method for breathing event inference and prediction may also include an effort/flow estimation model 770 for estimating respiratory effort and/or respiratory flow for a subject.

(a) Effort Estimation Model

Respiratory effort is a measure of the effort exerted by a subject during breathing cycles. During laboratory polysomnography (PSG) studies, respiratory effort is often estimated indirectly through the use of "surrogate" signals, as direct sensory measurements are typically not readily available.

One technique for estimating respiratory effort is through the use of esophageal balloon manometry. Esophageal balloon manometry involves inserting an empty balloon through the subject's nose, and into the subject's esophagus via a flexible tube catheter. The inserted balloon is inflated and one or more coupled pressure sensors record the subject's esophageal pressure throughout their breathing cycles. The recorded pressure data is then used as a surrogate signal for the subject's respiratory effort. While the use of esophageal balloon manometry has been considered the gold standard for monitoring respiratory effort, its primary disadvantage has been its highly invasive nature.

Another common technique for generating surrogate respiratory effort signals, and which may be considered less invasive than esophageal balloon manometry, is through the use of thoracic and abdominal RIP (respiratory inductive plethysmography) belts. In this technique, a first belt is positioned around the subject's thoracic area, while a second belt is positioned around the subject's abdominal area. Each belt contains a conductor that forms a wire loop to generate an inductance proportional to the absolute cross-sectional area of the body part that the belt surrounds. The use of the two belts allows detection of relative changes in the tidal volume of the subject's chest during inspiration and expiration. The calibrated weighted sum of the signals, generated by each belt, is then used as the surrogate signal for estimating the subject's respiratory effort, and can be used to detect sleep-based events (i.e., hypopnea and apnea events). Measurements based on traditional RIP techniques are, however, subject to numerous inaccuracies. For example, slippage of the belts or positional changes of the subject during sleep can result in erroneous measurements.

In view of the foregoing, in embodiments provided herein, to overcome at least some of abovementioned drawbacks of conventional methods for estimating respiratory effort, a method has been realized for deriving respiratory flow estimates using surrogate accelerometer signals—i.e., generated by a patch sensor device 100, 210, 300 positioned, for example, over a subject's suprasternal notch 156 (FIG. 1F)—and which can be used to detect various sleep-based events.

Figure 14A:
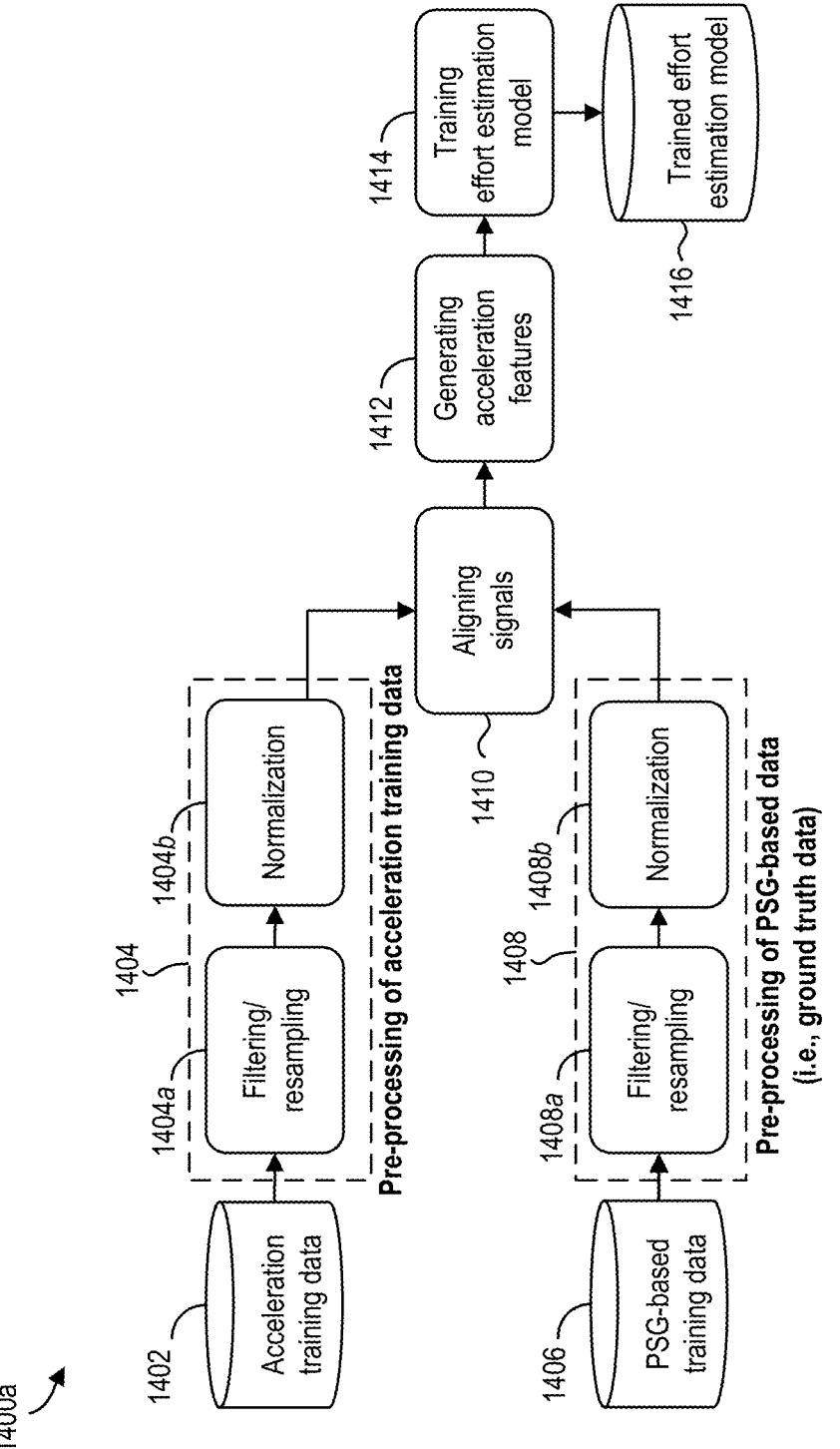
FIG. 14A shows an example method for training an acceleration-based respiratory effort model, in accordance with one or more embodiments.
Figure 14B:
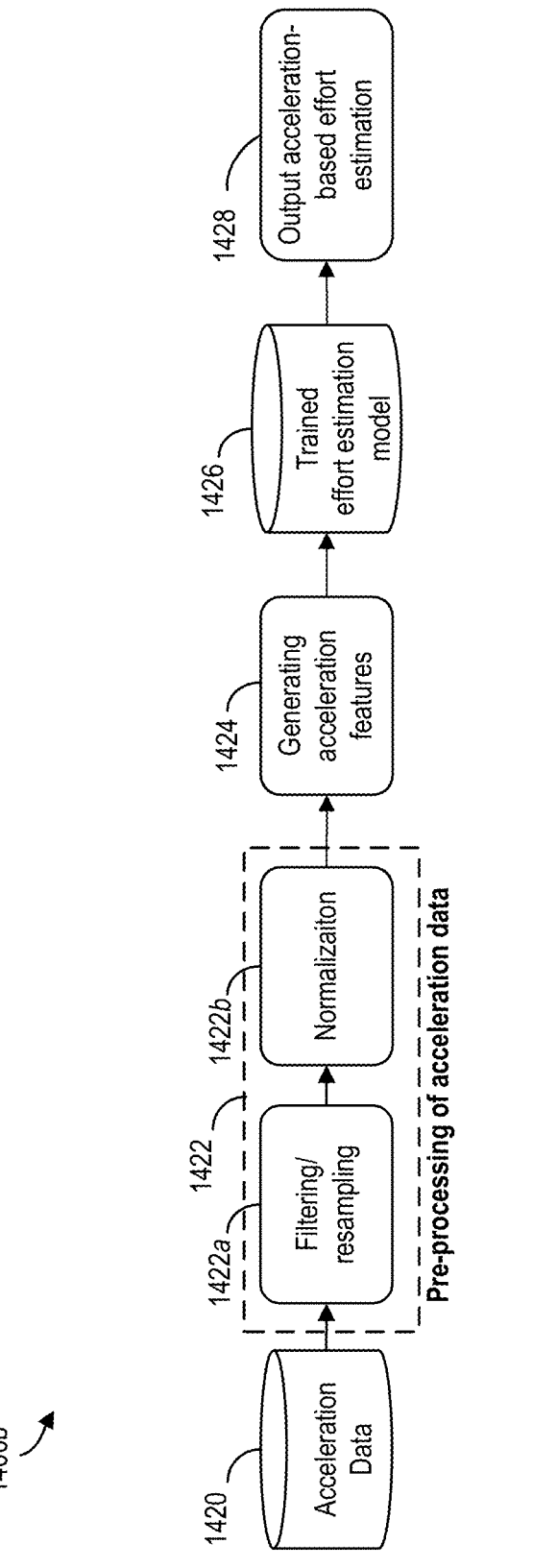
FIG. 14B shows an example method for applying an acceleration-based respiratory effort model, in accordance with one or more embodiments.

Reference is now made to FIGS. 14A and 14B, which show method diagrams of example embodiments of methods for training an acceleration-based respiratory effort model (see FIG. 14A), and applying the trained model to generate acceleration-based effort estimates (see FIG. 14B).

Reference is first made to FIG. 14A, which shows a method diagram of an example method 1400a for training an acceleration-based respiratory effort prediction model in accordance with one or more embodiments. The trained model may be used in 770 of FIG. 7B. The model training may be performed, e.g., on the server 206 (offline) (FIG. 2A), and the generated model may be stored in database 264. Method 1400a is initially described at a high level and then subsequently described at a more detailed level.

At a high level, the method 1400a comprises two parallel method sequences: (i) a first sequence involving pre-processing of acceleration training data (acts 1402-1404) and (ii) a second sequence involving pre-processing of PSG-based data (acts 1406-1408). The method proceeds to combine the pre-processed data from each flow to train the respiratory effort model (acts 1410-1416).

In the first sequence, the acceleration training data can correspond to previously acquired acceleration data from one or more sleeping subjects, i.e., acceleration data acquired from a patch sensor device 100, 210, 300 positioned on test sleeping subjects (FIG. 1F).

In the second sequence, the PSG-based data can correspond to surrogate signals acquired concurrently with the acceleration data, from the same subjects, during a PSG study. In at least one embodiment, the PSG data can correspond to the sum of signals generated by the positioning of the two RIP belts on subjects, as previously described (also known as a RIP sum). In other cases, the PSG data may also correspond to one or more of the individual signals generated by the thoracic and abdominal belts (i.e., without summing the signals). As explained in greater detail, method 1400a uses the PSG-based data as "ground-truth" data to train a model to estimate respiratory effort from patterns in the accelerometer data. Accordingly, the accelerometer data, e.g., acquired from a patch device 100, 210, 300, can be subsequently input into the trained model to generate acceleration-based respiratory effort estimates without the necessity of relying on the PSG data.

Method 1400a is now described in greater detail. Referring initially to the pre-processing of accelerometer data—at 1402, an acceleration training dataset may be accessed and/or retrieved. In some cases, the training dataset may be stored on the server's database 524 (FIG. 5) and accessed therefrom. As stated, the acceleration training data can correspond to previously collected data from one or more sleeping subjects that are equipped with a patch 100, 210, 300 having an accelerometer 338. In some embodiments, separate acceleration training data can be acquired from separate test subjects, and in respect of separate sleeping periods for each test subject.

In at least one embodiment, the obtained accelerometer training data can include two data channels—an "x"-axis accelerometer channel and a "z"-axis accelerometer channel (i.e., FIG. 1F). These channels can correspond to acceleration movements that are likely to vary during a subject's breathing cycle. In some embodiments, the accelerometer training data may be a time-series signal that is acquired by the patch device at a frequency of 100 Hz to provide for sufficient accuracy.

At 1404, the obtained accelerometer data may be pre-processed. The pre-processing of accelerometer data may involve one or more of: (a) filtering and/or re-sampling of the data (act 1404a), and (b) data normalization (act 1404b). For each dataset, the pre-processing may be performed on both the x-channel and z-channel subsets.

The filtering and/or re-sampling at act 1404a may remove bias or direct current (DC) frequencies from the signals, as well as removing very high frequency noise content. In some embodiments, the filtering is achieved by applying a band-pass filter having a passband range of 0.2 Hz to 5 Hz.

In some cases, at act 1404a, the accelerometer signals (i.e., the filtered accelerometer signal) may be further re-sampled, or down sampled. The down sampling may reduce the number of data points in the signal and may make the problem more tractable. In some cases, the accelerometer data is down sampled from a frequency of 100 Hz to 10 Hz.

At 1404b, each accelerometer signal (i.e., x- and z-channel signals) may be normalized.

In at least one embodiment, a change point detection (CPD) method may be used to normalize each accelerometer dataset. CPD is a technique for identifying significant or abrupt changes in time series signals, and can be applied to detect abrupt changes in the acceleration data that result from non-respiratory events (i.e., resulting from external biases introduced into the signal).

Figure 15A:
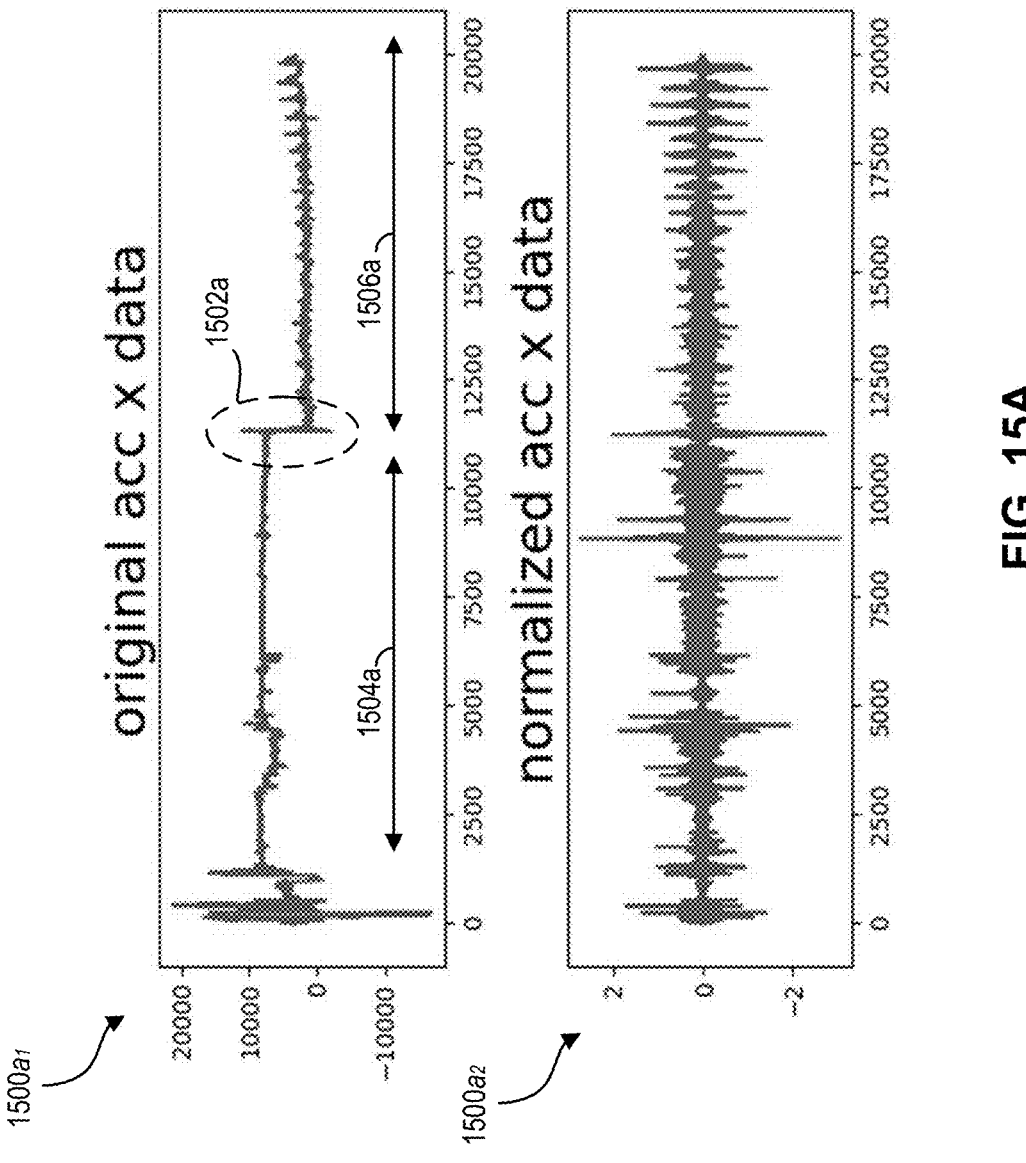
FIG. 15A shows example plots for acceleration time signals before and after normalization.

FIG. 15A shows an example of an applied CPD technique. More specifically, FIG. 15A shows an example time-domain plot 1500a₁ of an x-channel accelerometer signal whereby a CPD technique has identified an abrupt shift at point 1502a. While any know CPD method can be used at 1404b, in at least one embodiment, a pruned exact linear time (PELT) method may be used.

Once the shift points are identified using a CPD method, the signal can be segmented into one or more subsegments 1504a, 1505a of steady breathing movement that occur around, and between the shift points. Each subsegment (1504a, 1506a) may then be normalized to remove any evident bias and to regulate the data signal into a consolidated and unified range across the spectrum of the signal recording (i.e., removing the abrupt changes to normalize the signal). In at least some cases, the normalization may occur by using the difference between the $98^{th}$ and $2^{nd}$ percentiles. Plot $1500a_2$ in FIG. 15A illustrates the same signal plotted in plot $1500a_1$, but post-normalization.

In other embodiments, any other suitable technique can be used at 1404b to normalize the accelerometer data. For example, one or more features may be developed to provide for self-normalization. For example, a threshold coefficient of variation, or a local range or mean, may be determined. If the signal values exceeds the threshold or local range/mean, this can indicate an abrupt change in acceleration values, thereby prompting a normalization of the acceleration signal. In another example, a pre-filtered signal can be used to detect changes in the subject's body position based on the recorded accelerometer data. Once a change has been detected, this may also indicate that the accelerometer data requires normalization.

At 1408b, the accelerometer signals (i.e., filtered, resampled and/or normalized signals) may be further smoothened using a smoothing filter. In at least one embodiment, a Savitzky-Golay filter can be applied to smoothen the normalized accelerometer data (i.e., separate Savitzky-Golay filters may be applied to each of the x-channel and z-channel accelerometer signals).

Acts 1406-1408 may be analogous to acts 1402-1404, but may involve pre-processing obtained (or retrieved) PSG-based data, i.e., obtained or retrieved from the server's database 524. The PSG data can correspond to RIP signals comprising weighted sums of measured thoracic and abdominal signals for various subjects. In other embodiment, any other suitable PSG-based respiratory effort surrogate signal may be used. In at least one embodiment, each acceleration training dataset (i.e., x-channel and z-channel acceleration data pairs) may have a corresponding PSG data signal. The corresponding PSG-based signal may have been acquired concurrently at the same time the acceleration dataset was acquired from each test subject (i.e., using RIP belts). At act 1408, each PSG-based dataset may be pre-processed at 1408a and 1408b in a manner analogous to acts 1404a and 1404b.

While method 1400a illustrates pre-processing of both the acceleration and PSG data signals, in other embodiments such pre-processing may not always be necessary (i.e., depending on the quality of the original retrieved signals). In still other embodiments, any combination of the one or more above-described pre-processing acts may be performed on one or both of the acceleration and/or PSG datasets.

At 1410, each set of acceleration signals (i.e., pre-processed x-channel and z-channel signal pairs) may be temporally aligned with the corresponding PSG data signal (i.e., pre-processed PSG signals). As explained herein, aligning the signals can facilitate training a model to identify patterns between the acceleration data and the corresponding PSG data.

Figure 16:
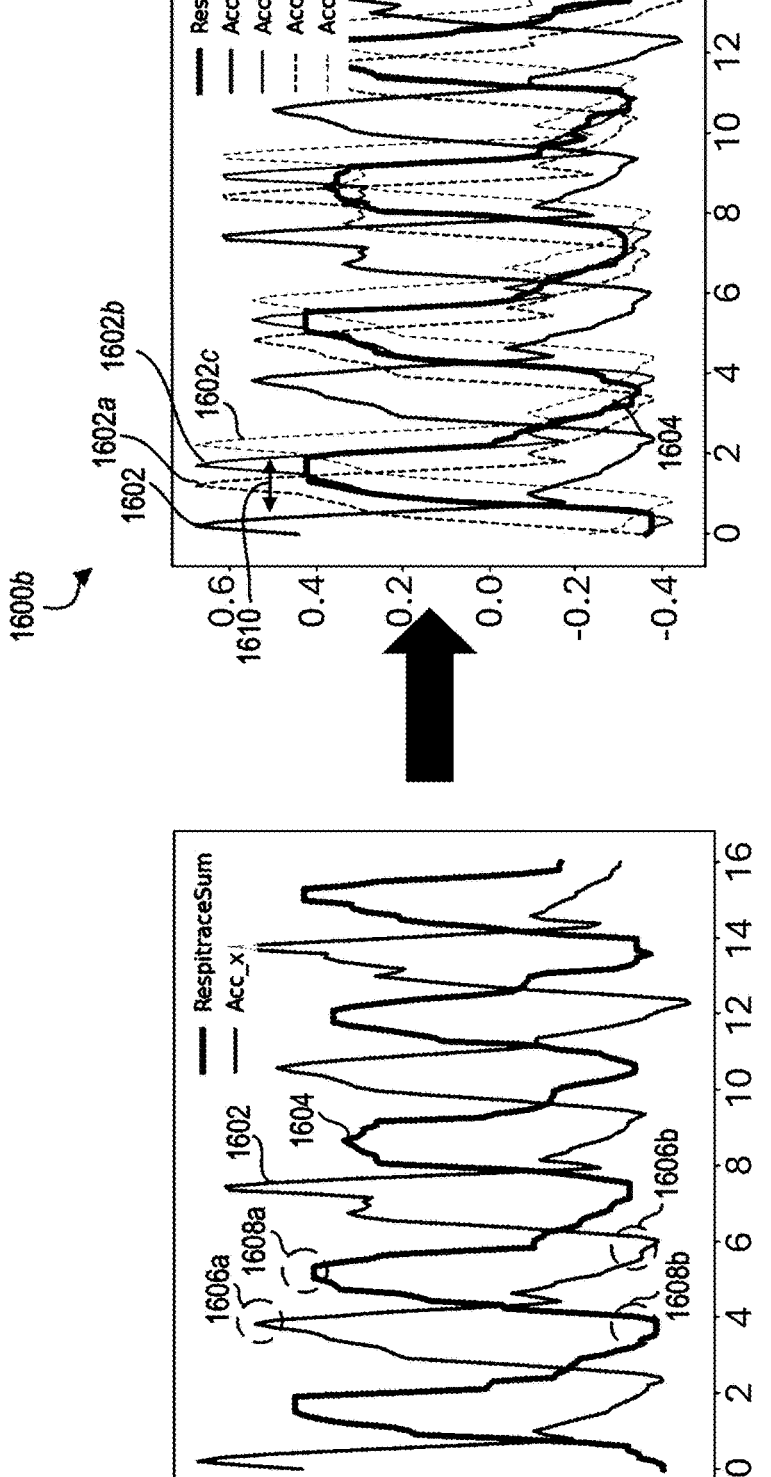
FIG. 16 shows example plots for acceleration time signals and PSG-based time signals before and after alignment.

To better illustrate the concept of signal aligning, FIG. 16 shows an example plot 1600a of an example x-channel accelerometer signal 1602, and its corresponding PSG data signal 1604. Plotted in the time domain, the two signals 1602, 1604 are observably phase mismatched. This mismatching is visually demonstrated at least by the peaks and troughs in the acceleration signal (i.e., peak 1606a and trough 1606b) which are unsynchronized with the corresponding peaks and troughs in the PSG signal (i.e., peak 1608a and trough 1608b). In various cases, the mismatching can results from signal acquisition errors.

To align the signals, at 1410, a cross-correlation technique can be used. The cross-correlation technique may involve selecting a signal (i.e., the acceleration signal), and incrementally shifting that signal in the positive and negative time directions until a cross-correlation value between the acceleration and PSG signals is maximized. Any cross-correlation function (CCF) known in the art may be used at act 1410 to achieve the signal alignment.

To further clarify this concept, plot 1600b in FIG. 16B illustrates the x-channel acceleration signal 1602 and corresponding PSG signal 1604. As shown, the acceleration signal 1602 is incrementally shifted in the positive time domain direction. For example, as shown, the acceleration signal 1602 may be shifted to positions 1602a, 1602b and 1602c in the positive time direction. With each time increment shift, a cross-correlation value is determined as between the shifted acceleration signal 1602 and the static PSG signal 1604. The method then determines the shift position that maximizes the cross-correlation between the two signals.

In the illustrated example, the cross-correlation value is maximized at the shift position 1602b, which corresponds to a match between the acceleration and PSG signals. An offset time value 1610 is then determined as between the original position of the acceleration signal 1602 and the shifted signal position 1602b which maximizes the cross-correlation value. This offset time value is then applied to correct all data points in the acceleration signal. The output of 1410 may be a new acceleration time series i.e., a1[n], a2[n], . . . ak[n] based on the offset time alignment.

In at least one embodiment, only the x-channel acceleration signal is initially used for determining the offset 1610. Once the offset 1610 is determined, it may then be applied retroactively to correct the corresponding z-channel signal, i.e., as the x- and z-channel signals share the same time offset. Additionally or alternatively, the z-channel signal can be used for determining the offset 1610, and the offset may then be applied retroactively to correct the x-channel signal. In other embodiments, it may be the PSG signal that is shifted to determine the offset, rather than the acceleration signal.

In some embodiments, the offset 1610 is determined by shifting the relevant signal within a range of ±5 seconds, and with shift increments as small as 0.001 seconds.

In some cases, a moving window is employed (e.g., a five minute moving window), whereby in each window, a derived offset 1610 is determined and the offset is applied to the relevant data signal portions in that window. For example, for each window, an offset is initially determined for the x-channel acceleration signal (i.e., in the manner explained above). Once the offset is determined, the offset is then retroactively applied to the data points in the same window in the z-channel signal. The window is then moved, and the process is iterated until the signals are entirely aligned. In various cases, the use of a moving window may reduce the computational complexity of the alignment process, and may also offer higher accuracy alignment between the signals.

In other embodiments, in addition or in the alternative to using a cross-correlation function (CCF), other techniques for aligning signals (i.e., time-domain signals) at 1410 can be used (see e.g., techniques as explained in Coakley, K. J. and Hale P., "Alignment of Noisy Signals", IEEE Transactions on Instrumentation and Measurement, Vol. 50, No. 1, February 2001, pages 141-149).

At 1412, acceleration features may be extracted from the aligned acceleration signals, i.e., features can be extracted from the x-channel and z-channel signals. In some embodiment, the acceleration features determined at 1412 may simply correspond to nothing more than the aligned acceleration time signals (i.e., x and z channels).

At 1416, the generated acceleration features (i.e., the aligned acceleration time domain values in the x- and z-channels), as well as a time domain representation of the PSG-based signal, can be input into an untrained model. The model may be trained to determine and predict PSG-based respiratory flow based on input acceleration data (i.e., x-channel and z-channel acceleration data). For example, where the PSG-based data at 1406 is a RIP sum, then the trained model can predict RIP sum values based on input acceleration data. In this manner, the trained model can generate estimate respiratory effort surrogate signals using only input acceleration data.

In at least one embodiment, the trained model may be a regression model. For example, this may be a simple fitting model expressed as y=Ax+b (or y=Ax+b+penalty), wherein the coefficients "A" and "b" are solved in training the model using the input data. The regression model can be trained using feature input data (i.e., aligned accelerometer data) and target features (i.e., the PSG RIP sum), so as to generate correlative estimates between the two value sets.

Various methods that can be used to train the regression model include, for example, (i) using regularization (i.e., L2 or ridge-regression, and/or L1 or lasso regression) for solving collinearity between features; (ii) expanding the feature series to include context to extend. For example, this may involve, for each input acceleration value x[n], inputting a feature series x[n−b], x[n−b+1], . . . , x[n], x[n+1], . . . x[n+f], where b and f are forwards and backwards context, respectively (i.e., thereby allowing prediction of the RIP sum from the acceleration data at time index "n" based on a number of past and future time steps); (iii) using a bootstrap method for training to cope with large size of data sets; and/or (iv) capping the feature or target value by a mean of ±3 x standard of deviation to suppress impact of outlier entries. In cases where ridge regression technique is used, the ridge regression may have a 0.01 penalty term.

The trained model may be trained using an iterative or a non-iterative solver. In the case of an iterative solver, this can include a solver such as an sklearn library solver (i.e., an sklearn.linear_model.LogisticRegression library code). The sklearn solver may use n*10 as the default maximum number of training iterations, wherein "n" is the length of the output "y" (i.e., assuming y=Ax+b is the problem to solve), and using a default tolerance of $1 \times 10^{-3}$, i.e., which means that the iteration will stop either: (a) when the error reaches tolerance; and/or (b) when the iteration reaches the maximum iteration limit. In the case of a non-iterative solver, this may involve any known close-form solver known in the art.

At 1416, a trained model is generated (i.e., a trained regression model). In some cases, the parameters of the trained model may be stored in the server database 524. For example, the parameters for a trained ridge regression model (i.e., a basic fitting equation, such as y=Ax+b+penalty term) can include: the "A" co-efficient value in the format of an array of shape [n_targets, n_features] (i.e., n_target is 1), the "b" co-efficient value (i.e., intercept) having an array of shape [n_target, 1], and the selected penalty term.

Referring now to FIG. 14B, which shows a method diagram of an example method 1400b for applying the acceleration-based respiratory effort prediction model generated in method 1400a (i.e., 770 of FIG. 7B).

At 1420, new acceleration data may be collected from a subject. For example, this may include x-channel and z-channel acceleration data acquired from an accelerometer 338 in a patch 100, 210, 300 located on the subject (FIG. 1F).

At 1422, in some cases, the acceleration data may be pre-processed by applying filtering and/or resampling (1422a) and/or performing normalization (1422b). Acts 1422a and 1422b are generally analogous to acts 1404a and 1404b in method 1400a.

At 1424, one or more features may be extracted from the acceleration data signals. Act 1424 may be analogous to act 1412 in method 1400a. In some cases, the extracted features may be simply nothing more than the pre-processed acceleration data points.

At 1426, the extracted features may be input into the stored trained effort estimation model.

At 1428, an acceleration-based effort estimation can be generated. The acceleration-based effort estimation model can estimate PSG surrogate effort values (i.e., RIP sum values) based on input acceleration values (i.e., x- and/or z-channel acceleration).

Figure 15B:
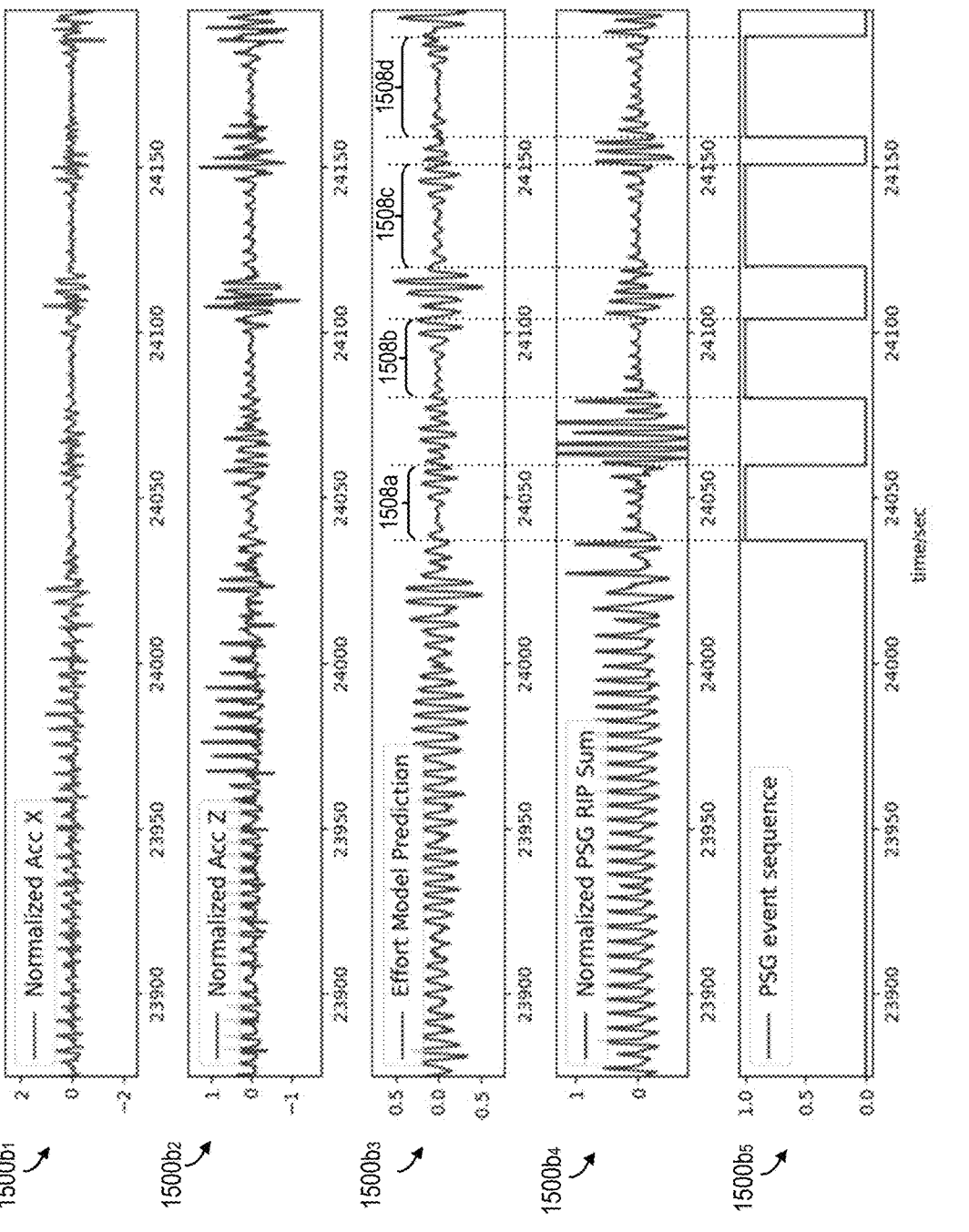
FIG. 15B shows example normalized accelerometer plots, an output signal for an acceleration-based effort prediction model and a normal polysomnographic (PSG) respiratory inductive plethysmography (RIP) sum plot.

Referring briefly to FIG. 15B, which shows time-domain plots 1500$b_1$ and 1500$b_2$ of acquired and normalized accelerometer signals (i.e., output of act 1422b in FIG. 14B), including a normalized x-channel accelerometer signal (plot 1500$b_1$) and a normalized z-channel accelerometer signal (plot 1500$b_2$). The output accelerometer-based effort prediction signal (i.e., as a result of the method 1400b (act 1428)), responsive to the input signals of plots 1500$b_1$ and 1500$b_2$, is illustrated in the plot 1500$b_3$.

For comparative purposes, a time-domain plot 1500$b_4$ of a normalized PSG RIP sum signal, i.e., captured concurrently with the accelerometer signals in plots 1500$b_1$ and 1500$b_2$, is provided, as well as a plot 1500$b_5$ of determined sleep events based on the PSG RIP plot 1500$b_4$ (i.e., wherein a magnitude of "1.0" corresponds to a detected sleep event, a magnitude of "0.0" corresponds to no detected sleep event). It can be observed that the plots 1500$b_3$ and 1500$b_4$ are visually analogous (i.e., the signal subsides in the same regions 1508a-1508d), confirming the ability of the trained effort estimation model (i.e., act 1426 in method 1400b) to generate predictions of a subject's PSG RIP sum using input accelerometer data. In other words, the accelerometer-based effort prediction can be used as a surrogate respiratory effort signal in place of the PSG RIP sum signal. In various cases, the acceleration-based effort prediction model can be used in place of the PSG RIP sum to determine the occurrence of various sleep events (i.e., apnea and hypopnea) (i.e., based on a technician observing and analyzing the plot 1500$b_3$, or otherwise through the use of computerized software that analyzes the plot). For example, events 1508a-1508d are visually indicated as extended reduced signals both in the plots 1500$b_3$ and 1500$b_4$.

(b) Flow Estimation Model

Similar to the respiratory effort model, a model may be generated to estimate respiratory flow based on accelerometer data. Respiratory flow refers to the volumetric flow rate of air inhaled and exhaled by a subject. In general, nasal pressure/pressure transducer systems are often used in PSG studies to generate surrogate signals to estimate a subject's respiratory flow. The use of nasal cannula's can, however, provide a discomforting experience for subjects. A method has therefore been realized for estimating a subject's respiratory flow based on accelerometer data, i.e., acquired from an accelerometer 338 inside patch 100, 210, 300. To this end, FIG. 17A shows an example method of training an acceleration-based respiratory flow estimation model, and FIGS. 17B and 17C show example methods of applying the model.

Figure 17A:
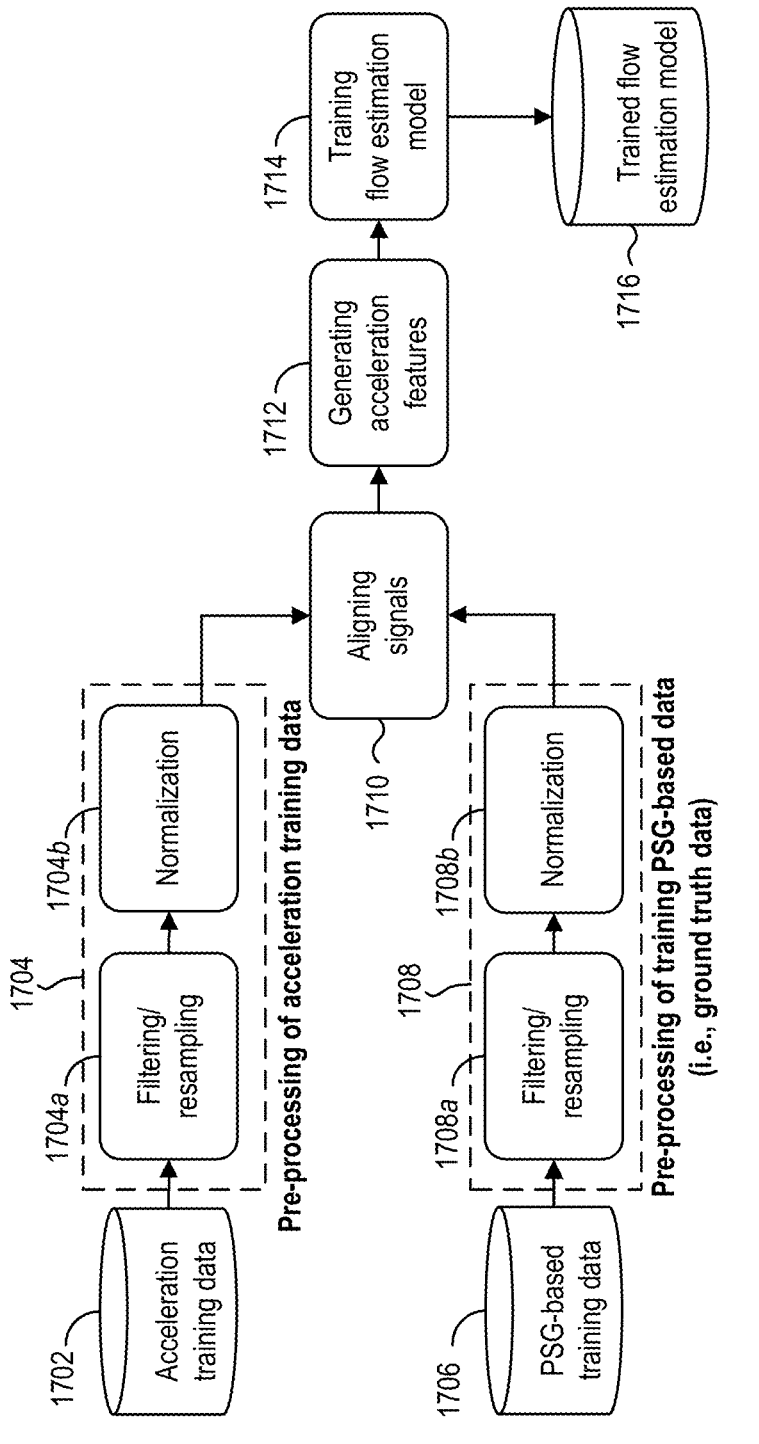
FIG. 17A shows an example method for training an acceleration-based respiratory flow model, in accordance with one or more embodiments.

Reference is now made to FIG. 17A, which shows a method diagram 1700a for an example method for training an acceleration-based respiratory flow estimation model in accordance with one or more embodiments. The trained flow model may be used in 770 of FIG. 7B, and can be used to predict respiratory flow from accelerometer data. The model training may be performed, e.g., on the server 206 (offline) (FIG. 2A), and the generated model may be stored in database 264.

Method 1700a is generally analogous to method 1400a of FIG. 14A (i.e., acts 1702-1716 are generally analogous to acts 1402-1416), with the exception that the PSG-based data at 1706 corresponds to surrogate flow data from a PSG-based study. For example, this can include nasal pressure data from a PSG study (i.e., as acquired from pressure transducer sensors).

Figure 17B:
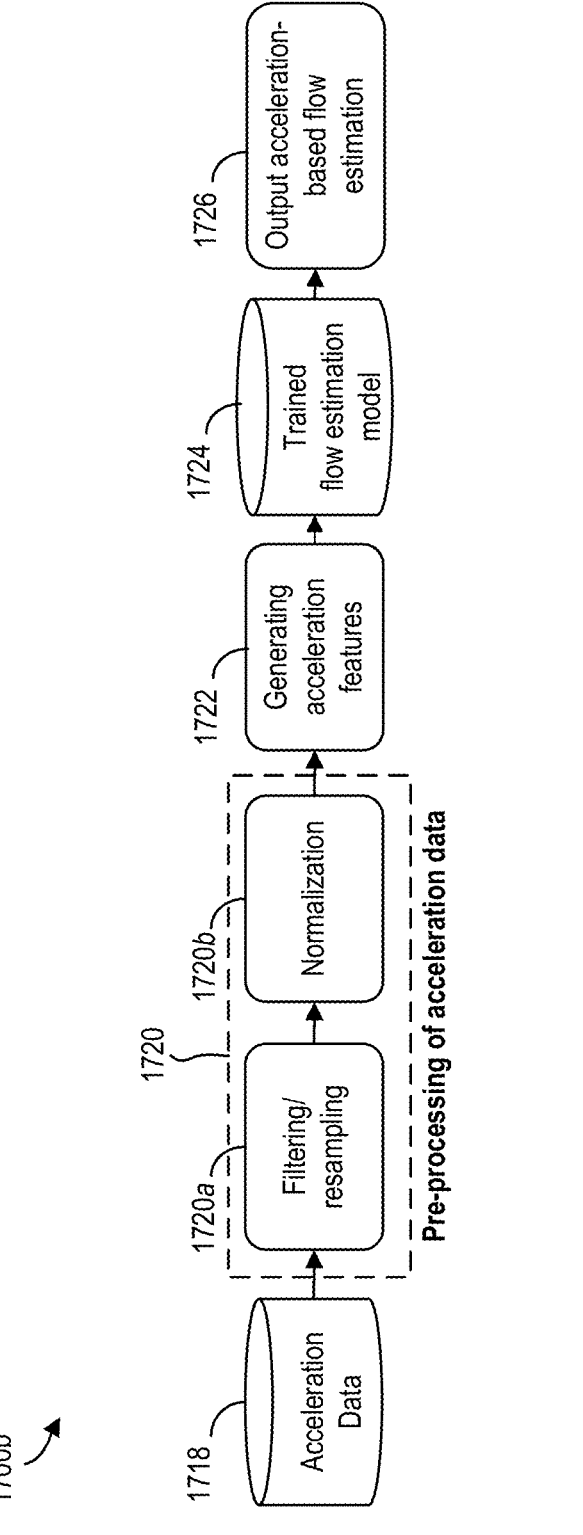
FIG. 17B shows an example method for applying an acceleration-based respiratory flow model, in accordance with some embodiments.
Figure 17C:
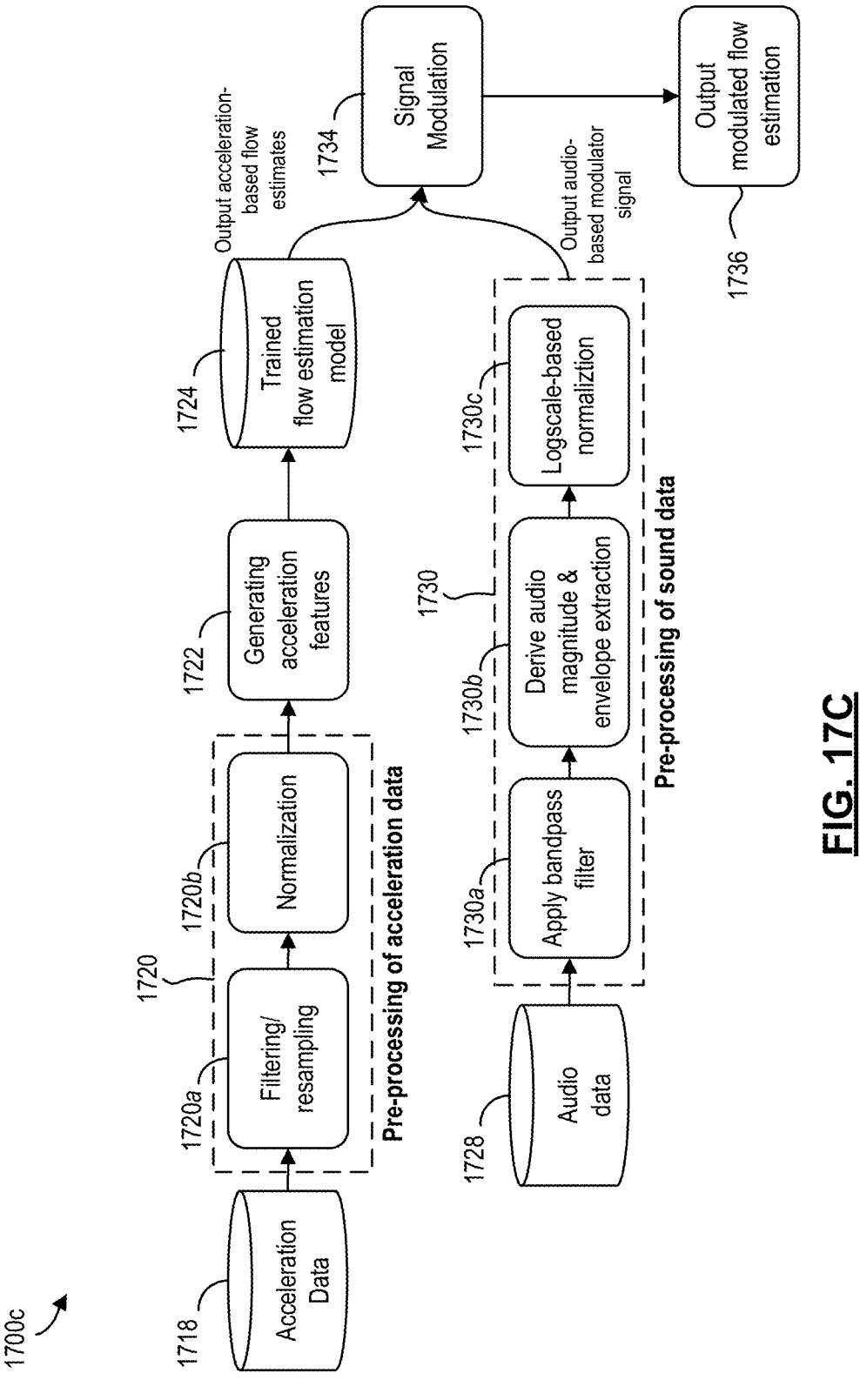
FIG. 17C shows an example method for applying an acceleration-based respiratory flow model, in accordance with some other embodiments.
Figure 18:
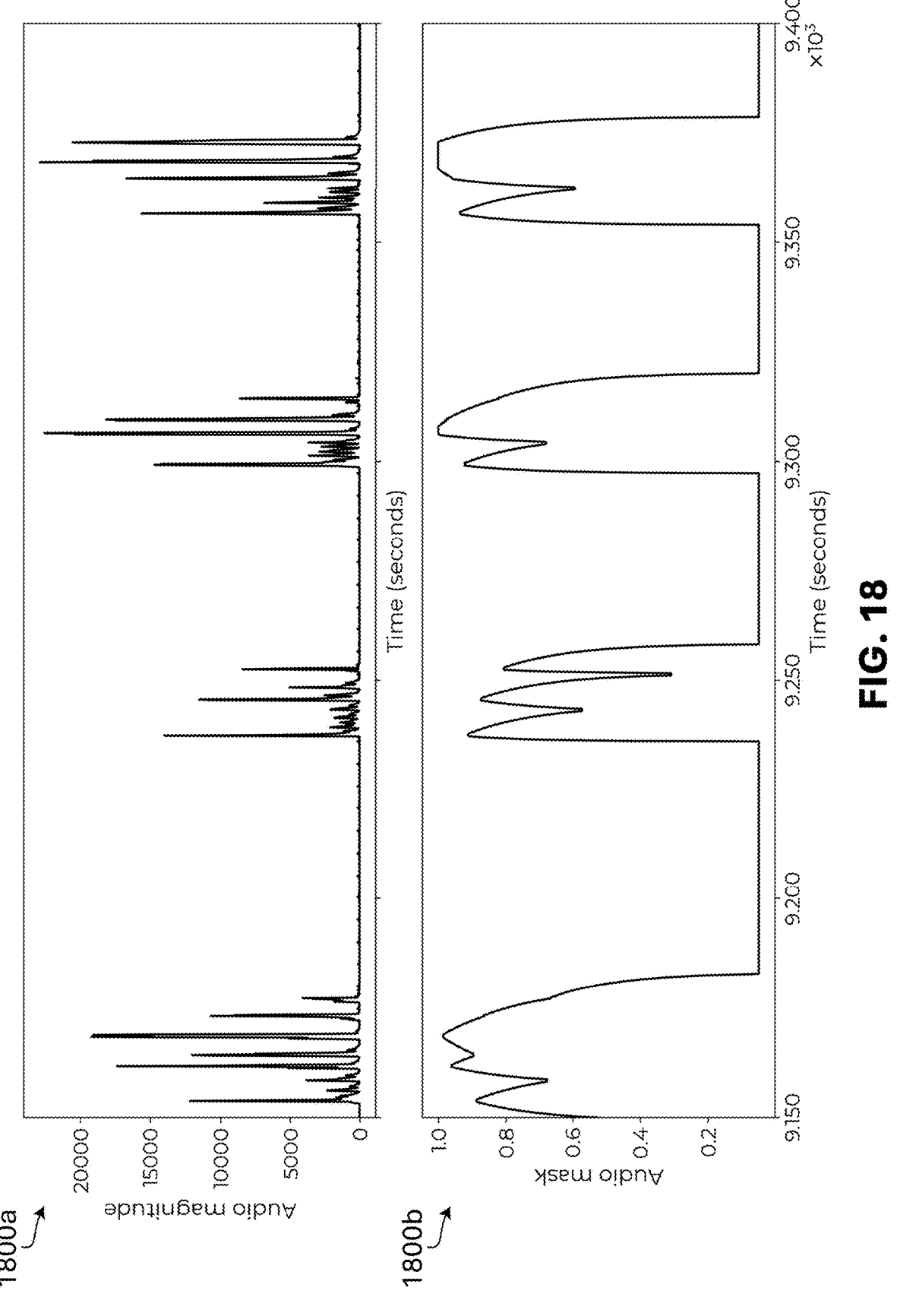
FIG. 18 shows example plots of audio signals after deriving magnitude and performing envelope extraction.

Reference is now made to FIG. 17B, which shows an example embodiment of a method diagram 1700b for generating output acceleration-based flow estimates. The method 1700b is generally analogous to the method 1400b of FIG. 14B (i.e., acts 1718-1726 are generally analogous to acts 1420-1428), with the exception that method 1700b generates respiratory flow estimates at act 1726 based on acceleration data (i.e., x- and z-channel) input into the model generated in method 1700a at act 1716.

Reference is now made to FIG. 17C, which shows an example embodiment of a method diagram 1700c for generating output acceleration-based flow estimates. The method 1700c is generally analogous to the method 1700b, but may generate enhanced flow estimate predictions by modulating the acceleration-based flow estimates at 1724 with an audio-based modulator signal.

As shown, at 1728, audio data may be acquired concurrently with the acceleration data. For example, the audio data may be acquired from the patch audio sensor 336, and can correspond to a subject's generated tracheal sound.

In some embodiments, at 1730, the audio data may undergo pre-processing. For example, the pre-processing can include one or more of: (i) at 1730a, filtering the audio data to generate filtered audio data. The filtering may involve applying a bandpass filter to remove high frequency noise (i.e., a bandpass filter having a passband of 200 Hz-2,000 Hz); (ii) at 1730b, an audio magnitude signal may be derived and a signal envelope may be further extracted. For example, plot 1800a shows an example audio signal after deriving the audio magnitude. Further, plot 1800b shows an example extracted signal envelope from the magnitude signal in plot 1800a. and (iii) at 1730c, the extracted envelope can undergo a logscale-based normalization. In some cases, the normalization is performed by taking the $5^{th}$ and $95^{th}$ percentile difference. In some embodiments, the normalized log-envelope is further gated, i.e., to between 0.05 and 1 and performing median filtering.

In respect of the derivation of the audio magnitude at 1730b, this may be performed by: (i) segmenting the audio signal into one or more audio segments (i.e., audio segments of 0.1 seconds in length); (ii) determining the mean-absolute value of each audio segment (i.e., corresponding to the magnitude of that segment).

As a result of 1730b, an output signal may be generated which comprises a plurality of mean-absolute values for each segment of the original audio signal. This output signal can correspond to the audio magnitude signal. In some cases, the length of the audio segment can be selected in view of the accelerometer data frequency (i.e., after down sampling). For example, where the accelerometer data signal is down-sampled at act 1720a to 10 Hz frequency, the audio signal may be segmented into segments of 0.1 seconds in length. In this manner, the audio magnitude sequence may also have a 10 Hz frequency. In at least some embodiments, this can improve modulation of the acceleration data using the audio signal as explained at act 1734 by synchronizing the frequencies such as to allow for one-to-one modulation (i.e., multiplication) between the acceleration and audio signals.

At act 1730b, determining the signal envelope from the audio magnitude signal may performed using various methods including, for example, using rectification techniques and/or Hilbert transforms. Envelope extraction can be used to remove strong high-frequency components, i.e., fast variations, from the audio magnitude sequence. These fast variation may be undesirable when the signal is used to detect breathing and/or event patterns, which are normally expressed below ½ Hz (or even lower). The envelope extraction may therefore remove the high-frequency components from the audio magnitude, while maintaining slow-changing patterns.

At act 1730c, the log-scale based normalization can assist in generating log-scale tracheal sound statistics that are "well fitted" with the measured airflow (see e.g., Yadollahi A, Moussavi Z M "Acoustical respiratory flow. A review of reliable methods for measuring air flow", IEEE Eng Med Biol Mag. 2007 January-February; 26(1):56-61.doi: 10.1109/memb.2007.289122. PMID: 17278773). In other embodiments, any suitable method of signal normalization may be used.

As mentioned previously, the normalized signal can also be further gated at 1730c. Gating can prepare the audio signal for modulating the acceleration-based flow estimate, i.e., at act 1734. The purpose for gating the log-normalized audio signal at the lower end (i.e., gating at 0.05) may be to prevent zeroing-out of the acceleration-based flow estimates during modulation. For example, gating the audio signal at the lower end can remove—from the normalized audio signals—values of audio at "zero" magnitude. This is because when modulating the flow estimate 1734, an audio value of "zero" will simply result in a modulated output of zero (i.e., when multiplying the signals), irrespective of the value of the flow estimate being modulated (i.e., thereby causing a loss of data). The selection of a small positive value at the lower end (i.e., gating at 0.05) may also be sufficient to help reveal (or prevent concealing) target events (e.g. revealing apnea which is typically at 10% of baseline airflow for no less than 10 seconds). In respect of gating at the high end (i.e., gating at a high-end value of '1')—during modulation, this may prevent amplifying the acceleration-based flow estimate, even when the audio signal is very loud (which may or may not relate to a sleep disorder).

At 1734, the output audio-based modulator signal (i.e., that results from acts 1730a-1730c) is used to modulate the output acceleration-based flow estimate generated at act 1724. The modulation may involve multiplying the two signals to generate an output modulated flow estimation at act 1736.

In various cases, the modulation, at act 1734, is used to emphasize (or amplify) the 'contrast' of airflow between periods of high and low possibility of existence of disorder events. This, in turn, may make it easier to identify events in the output flow estimation. That is, by amplifying low and high detected airflow periods, this may assist in detecting: (i) the start of an occurrence of an event (i.e., corresponding to a low airflow period) and/or (ii) the ending of the event (i.e., corresponding to a high detected airflow period). As such, the use of the audio data (i.e., tracheal sound data) to modulate the flow estimate signal facilitates enhanced clarity in identifying events (i.e., visually) in the modulated flow estimation signal. Further, the tracheal sound data is used as the modulator as it is an indirect indicator of the subject's airflow, and can therefore be used to emphasize the contrast of airflow in the flow estimates.

In at least some embodiments, if there is high confidence that certain periods of the accelerometer and/or noise recording demonstrates regular and steady sleep, these periods can be excluded from modulation because they are not needed to emphasize sleep events.

In some embodiments, prior to performing the modulation at act 1734—the acceleration-based flow estimate may undergo further processing (i.e., further processing that occurs between acts 1724 and 1734). This processing may involve a time and frequency analysis to exclude, from modulation, pre-defined portions of the acceleration flow estimates that are not required for event detection (i.e., pre-defined portions corresponding to regular steady sleep).

In at least one embodiment, this further processing may involve frequency-domain processing (i.e., applying a Fast Fourier Transform (FFT) to the output flow estimate signal at act 1724) to generate a power spectral density signal. From the spectral density signal, a ratio of low frequency components can be derived. If the ratio is higher than a pre-determined threshold, then this portion of the signal can be considered to correspond to a regular steady sleep (i.e., due to there being a high ratio of low frequency components thereby indicating a steady sleep cycle), and can be excluded from modulation. In at least one embodiment, the ratio is determined for frequency components 1/7.5 to ½ Hz, and the pre-determined threshold may be around ⅓.

Alternatively or in addition, in at least one other embodiment, the abovementioned further processing may also include time-domain processing of the output flow estimate signal (i.e., at act 1724) to identify portions of the signal that comprise a flat envelope. This may involve determining portions of the time-domain output acceleration-based flow estimate signal that exceed a pre-determined threshold of a flatness-based metric. In at least one embodiment, the flatness-based metric is determined based on a spectral flatness calculation (i.e., calculating a Wiener entropy of signal portions), which expresses the flatness in a range of '0.0' to '1.0', wherein '1.0' expresses a flatter sequence. The pre-determined threshold for determining a flat envelope may be a flatness metric between, e.g., 0.8 to 1.0, or above 0.5.

The excluded portions of the acceleration-based flow estimate signal (i.e., based on the aforementioned frequency and time domain analysis), can represent portions of steady sleep that may be excluded from the modulation. That is, these are portions of the output signal that are unlikely to correspond to target sleep events (i.e., apnea or hypopnea), and therefore, are of less relevance to the output flow estimate signal and can therefore remain unmodulated. In some cases, this processing may be performed in windowed-sequences (i.e., each five minute window of flow estimate data may be processed in this manner to find windows which meet the conditions of: (i) flat envelope and (ii) dominant frequencies in the pre-defined range).

Figure 19:
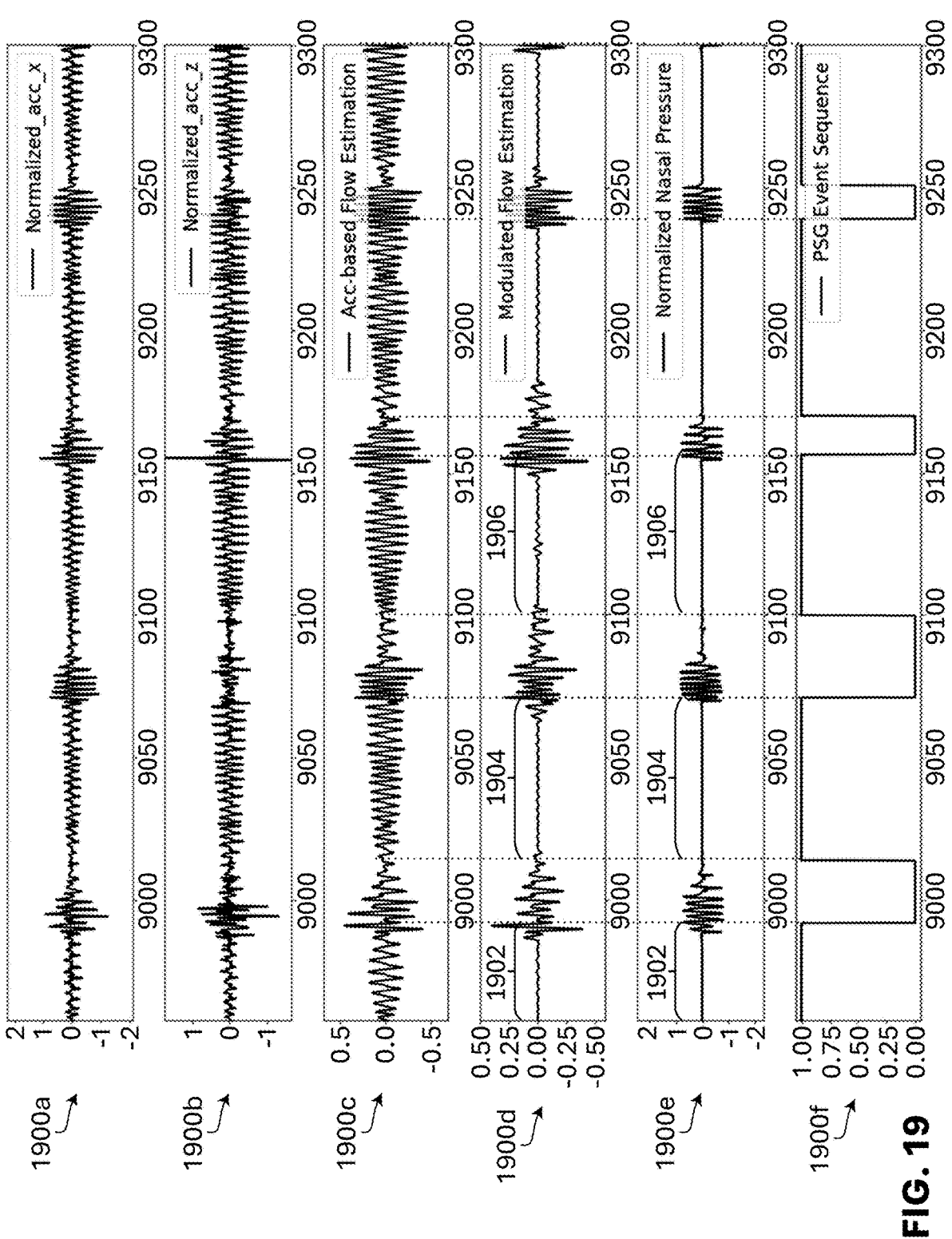
FIG. 19 shows example plots of normalized nasal pressure, modulated flow estimates and PSG event sequences.

Reference is now made to FIG. 19, which shows various example plots that may result from the method 1700c in FIG. 17C.

Plot 1900a and 1900b illustrate example normalized x-channel and z-channel accelerometer data, respectively, that may result from acts 1718-1722 in FIG. 17C, i.e., based on acceleration data captured from a patch device 100, 210, 300. Plot 1900c shows an example acceleration-based flow estimate that is generated as a result of act 1724 in method 1700c based on the input normalized x- and z-acceleration data in plots 1900a and 1900b. Plot 1900d shows a modulated version of the acceleration-based flow estimate in plot 1900c that can result from act 1734 in method 1700c.

For comparative purposes, FIG. 19 also shows plot 1900e, illustrating normalized nasal pressure data that may have been captured concurrently from a test subject (i.e., via traditional nasal pressure/pressure transducer systems) with the acceleration data in plots 1900a and 1900b. Further, plot 1900f shows event detection as a result of a PSG-based study (i.e., using the nasal pressure data), whereby a magnitude of "1.0" indicates a detected sleep event (i.e., apnea or hypopnea) and a magnitude of "0.0" indicates a non-event.

As shown, the plots 1900d and 1900e demonstrate a high level of analogous visual similarity. For example, the signal portions 1902 to 1906 in the nasal pressure signal 1900e correspond to time periods of low respiratory flow, and can indicate (i.e., in a PSG-based study) a sleep event (i.e., apnea or hypopnea event) (see e.g., see plot 1900f, whereby signal portions 1902-1906 align with detected events). These same events are visually observable in the modulated flow estimation in plot 1900d, thereby confirming the ability of the method 1700c to generate acceleration-based modulated flow signals that visually mimic the flow surrogate signal ordinarily generated by PSG-based studies (i.e., via nasal pressure systems). Accordingly, the signal 1900d can act as respiratory flow surrogate signal that can be used by a technician (or a computer software), to observe or detect sleep events based on acceleration data generated by a patch device.

ix. Model Evaluation

Figure 20:
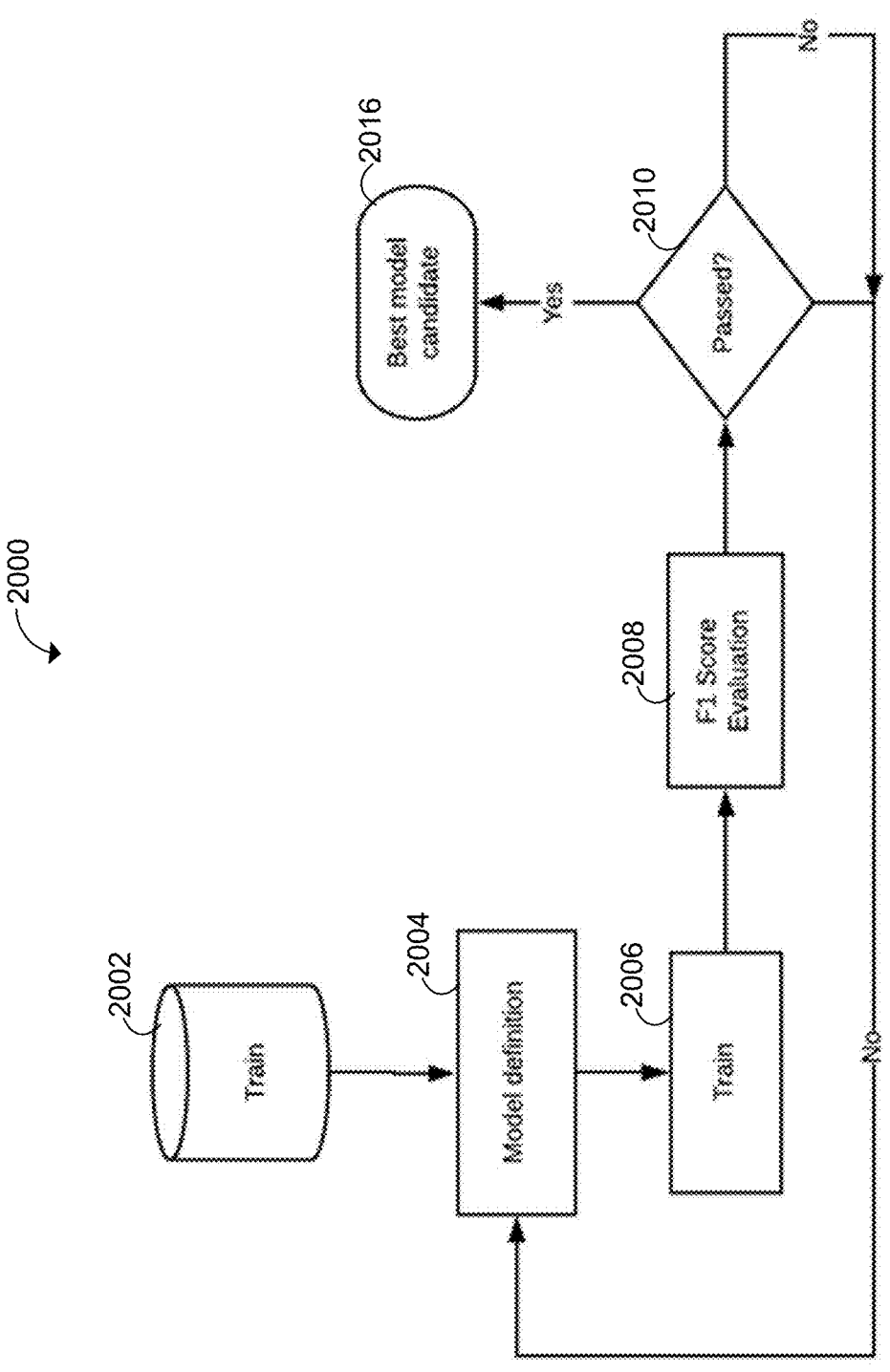
FIG. 20 shows an example event detection model evaluation method in accordance with one or more embodiments.

Referring next to FIG. 20 there is shown a method diagram 2000 of an example event detection model evaluation method in accordance with one or more embodiments.

Once a first deep learning model, a second deep learning model, a sleep detection model and/or a flow and/or effort model are generated, they may be evaluated using the validation dataset.

To generate the deep learning models, neural networks, sleep models and/or flow and/or effort models, training data 2002 is supplied. The training data may be historical sensor data that may have been scored manually by clinicians, for example, using manual scoring interface 270 (see FIG. 2B). The manual scoring may include reviewing sensor data and identifying CSA or OSA events.

At 2004, a model definition configuration is received. This may include specific details about how feature extraction could work, what fields are used for training, the format of any data within the training dataset 2002, etc.

At 2006, model training is executed, included determining a model from the training data 2002 and the model definition 2004. This may include using a deep learning model training method, a random forest model training method, another machine learning training method as known, and/or a regression model.

At 2008, the validation dataset is used with the generated model to determine an F1 score. The F1 score may be the harmonic mean of the precision and recall. This may determine the efficiency and accuracy of the generated model based on the validation dataset. The highest possible value of an F1 score may be 1.0, indicating perfect precision and recall, and the lowest possible value is 0, if either the precision or the recall is zero. The F1 score is also known as the Sørensen-Dice coefficient or Dice similarity coefficient (DSC). In cases where the validation set is used with the flow and/or effort model, act 2008 may involve determining a mean square error (MSE), rather than an F1 score.

At 2010, the determined F1 score may be compared to a threshold and it may be determined whether the generated model F1 score passes the threshold.

If the model passes, then the model may be identified as the best model candidate 2016.

x. Graphical User Interface (GUI) Configurations

Figure 21A:
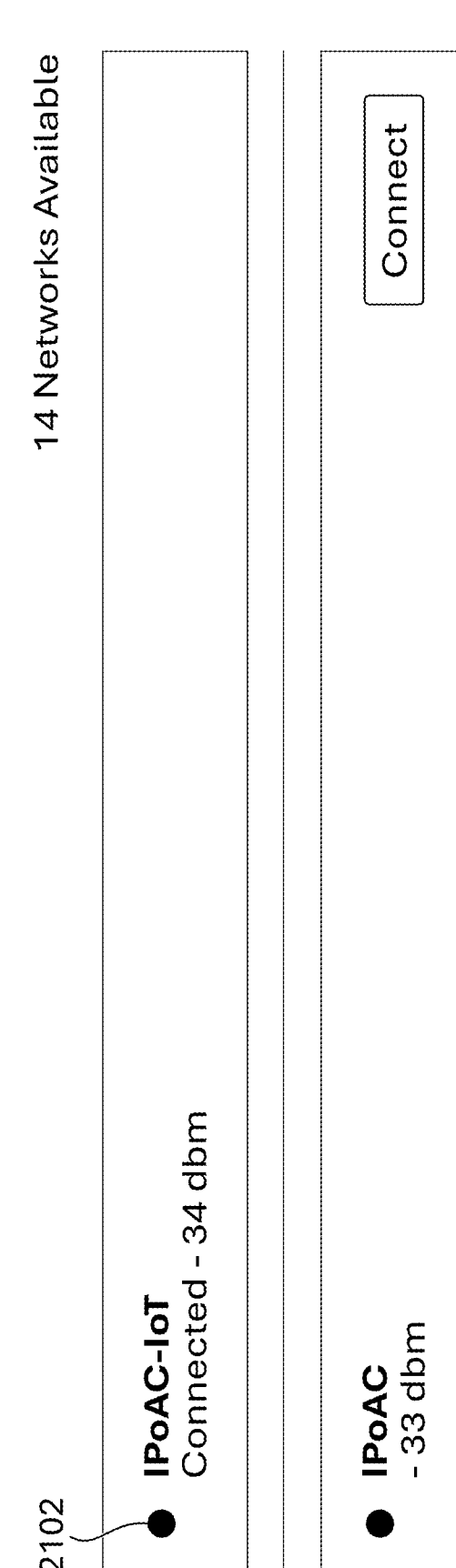
FIG. 21A shows an example user interface for hub device and patch device setup in accordance with one or more embodiments.

Referring next to FIG. 21A there is shown an example user interface 2100 for hub device and patch device setup in accordance with one or more embodiments. The user interface 2100 may be provided by hub frontend 236 via web server 272 (see e.g., FIG. 2B).

A clinician or a subject may use their device with wireless capabilities to connect to a wireless network provided by the hub device.

The subject or clinician may use a web browser on their device to access the web server of the hub device. The clinician or subject may specify a separate wireless network for the hub device to use when it is situated in the sleeping locale of the subject. For example, the hub device in interface 2100 may be connected to the IPoAC-IoT network 2102. This may allow for the configuration of the hub device and its connection to the internet.

Once connected to the internet via the wireless network, a clinician may link the hub device with the server using a user account of the server.

Figure 21B:
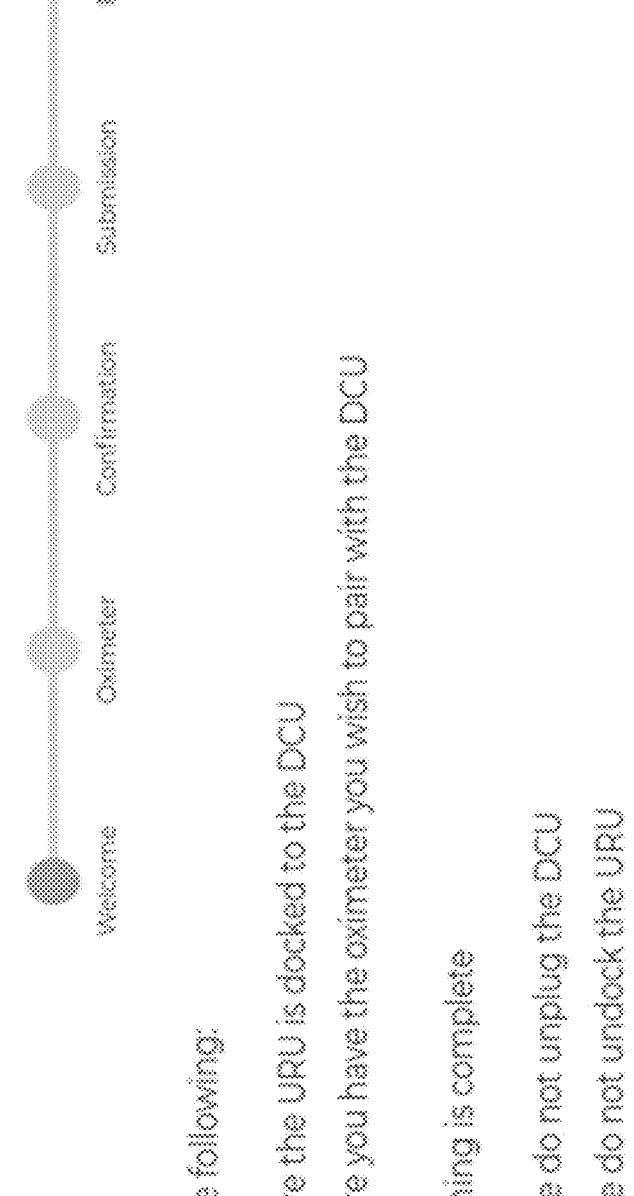
FIG. 21B shows another example user interface for hub device and patch device setup in accordance with one or more embodiments.

Referring next to FIGS. 21B and 21C, there are shown example user interfaces 2110 and 2120 for hub device and patch device setup in accordance with one or more embodiments. The user interfaces 2110 and 2120 may be provided by hub frontend 236 via web server 272 (see e.g., FIG. 2B).

A clinician or subject may access the web server of the hub device to pair the patch device and optionally an oximeter with the hub device. This may be initiated by docking the patch device in the hub device, accessing the web server of the hub device, and then clicking next 2112.

The clinician or subject may "prime" the devices in an initial configuration step as shown in interface 2120 where the patch and optionally the oximeter are paired with the hub using the web server of the hub device, by clicking the prime button 2122.

The clinician may perform the pairing of the hub device, patch device, and optionally the oximeter and then provide the hub, patch and optionally the oximeter to a subject.

Referring next to FIG. 21D there is shown an example user interface 2130 for subject sleep session recording control in accordance with one or more embodiments. The user interface 2130 may be provided by hub frontend 236 via web server 272 (see e.g., FIG. 2B).

A subject who accesses the web interface 2130 on the hub device may control the sleep sensor recording. The interface 2130 may show connected sensor equipment such as the patch device and the oximeter device, may show recording state (either active or inactive), and may show an elapsed recording time once the sensor data collection has begun. The subject may access the interface and select the start button 2132 to initiate the sensor data collection from the patch and oximeter. They may attach the patch device and the oximeter to their body before or after selecting the start button 2132. Responsive to the initiation of the sensor data collection, the hub device may begin collecting audio data, accelerometer data, and oximeter data as disclosed herein.

The subject may access the interface 2130 at the end of their sleep session and select the stop button 2134 to end the sensor data collection.

Referring next to FIG. 21E there is shown an example user interface 2140 for uploading sleep session recording data in accordance with one or more embodiments. The user interface 2140 may be provided by hub frontend 236 via web server 272 (see e.g., FIG. 2B).

Once the subject has completed the prescribed number of sleep session data recordings, the hub, patch, and oximeter devices may be returned to a clinician who may access the interface 2140 on the hub device and review and upload the collected sensor data. Alternatively, the subject themself may access the interface 2140 and upload the sleep sensor recording data.

The clinician or subject may access the recording history interface 2140 and select the test(s) they wish to upload to the cloud-based recording storage for analysis. For example, sleep session 2142 may be selected for upload by clicking upload button 2144. The selection of upload button 2144 may trigger the upload of the accelerometer, audio, and oximeter data to the cloud for analysis. This may include requesting authorization to upload data to cloud-based recording storage. Authorization may involve verifying a user account linked to the hub device.

Upon sleep session data upload completion, the portal backend may place the test in a first-in-first-out processing queue for analysis. The analysis algorithm may take tests from a queue, download recording data from recording storage and perform analysis as described herein (for example, automatic analysis 268 in FIG. 2B).

Referring next to FIG. 21F there is shown an example clinician interface 2150 in accordance with one or more embodiments. The user interface 2150 may be provided by clinician frontend 254 (see e.g., FIG. 2B).

A clinician user may connect to the clinician frontend and login using user credentials. A clinician may review uploaded tests from subjects, including analysis status 2154, sharing of the test result and corresponding analysis data 2156, and a view/edit button 2158 that may allow for a clinician user to open the interface in FIG. 21G to view and edit the test data and annotations.

For example, a test such as test 2152 with 'Analysis Complete' as its status 2154 may be one that has been processed by the automatic analysis algorithm as described herein.

A user can click the View/Edit button 2158 of test 2152 to see a summary of the test's information and results. The user may create new test revisions by editing the test information and results as shown in FIG. 21G.

Figure 21G:
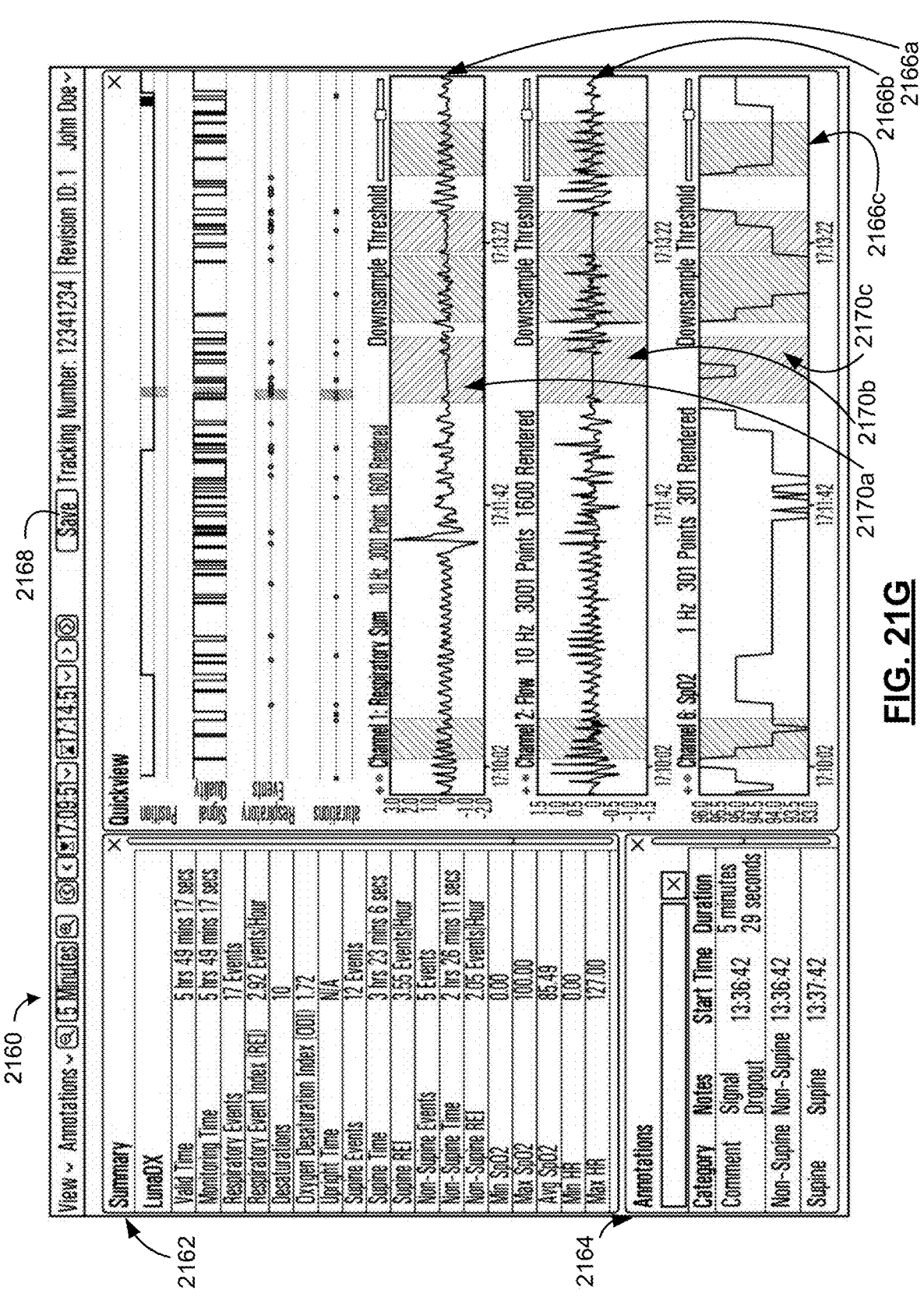
FIG. 21G shows an example clinician interface in accordance with one or more embodiments.

Referring next to FIG. 21G, there is shown an example clinician interface 2160 in accordance with one or more embodiments. The user interface 2160 may be provided by clinician frontend 254. The user interface 2160 may include a summary panel 2162, an annotation panel 2164, and one or more sensor data channels 2166, for example a first channel 2166a, a second channel 2166b and a third channel 2166c.

The summary panel 2162 may include summary data determined from the sensor data of the sleep session of the subject, such as monitoring time, number of respiratory events, a respiratory event index, a number of oxygen desaturations, a rate of oxygen desaturations, a period of upright time, a number of supine events, a period of supine time, a supine REI, a minimum oxygen value (SpO2), a maximum oxygen value (SpO2), an average oxygen value (SpO2), minimum heart rate values, maximum heart rate values, etc.

The annotation panel 2164 may include automatically generated event annotations and clinician annotations. The annotations may be associated with a time index and one or more sensor data channels. The annotations may each include a category, notes, a start time, and a duration.

The manual scoring and review interface 2160 may allow a clinician user to review subject sleep data collected from the hub, patch, and oximeter devices. The manual scoring and review interface 2160 may allow a clinician to modify the automatically identified sleep events, or "score" a revision of the sensor data. The clinician may also select the "View Revisions" button to choose another revision for review. A user may be redirected to a manual scoring application to edit or change the annotations or detected events in the sensor data channels 2166. The sensor data channels 2166 may include a respiratory channel 2166a, a flow channel 2166b and an oximeter channel 2166c.

The interface 2160 may show events automatically identified in the sleep sensor data, such as event 2170. Event 2170 may indicate an identified sleep event (for example an apnea or hypopnea), including a highlighted respiratory regions 2170a, a highlighted flow region 2170b, and a highlighted oximeter region 2170c in the interface.

The scoring application may communicate with the portal backend to obtain authorization to download EDF and annotations data for the given revision from cloud recording storage. The clinician may view the data and annotations and make modifications with real-time feedback.

When a clinician user finalizes the annotations of the sensor data, they may save the annotations in a new revision by clicking Save button 2168 in the manual scoring application.

The clinician user may review the changes against the starting revision and may include comments describing their changes.

The health care provider may then submit the changes, and the updated annotations may be uploaded to the cloud recording storage and the rescored results may be saved in the portal backend database.

The present invention has been described herein by way of example only. Various modification and variations may be made to these exemplary embodiments without departing from the spirit and scope of the invention, which is limited only by the appended claims.

We claim:

1. A computer-implemented method for breathing signal analysis for characterizing at least one recorded signal as indicative of one of Obstructive Sleep Apnea (OSA) and Central Sleep Apnea (CSA), the method comprising:

receiving, at a processor, an audio signal and a corresponding accelerometer signal;

determining, at the processor, a frequency domain representation of the audio signal;

sorting, at the processor, at least one frequency interval component of the frequency domain representation of the audio signal into at least one corresponding frequency bin;

determining, at the processor, a signal-to-noise ratio (SNR) signal for each frequency bin during a candidate time period; and determining, using a machine learning model at the processor, an indication of an OSA event or a CSA event based on the SNR signal for each frequency bin during the candidate time period, the audio signal for the candidate time period, and the accelerometer signal for the candidate time period.

2. The method of claim 1, further comprising:

determining a local minima for each frequency bin during the candidate time period; and wherein the determining the SNR signal for each frequency bin comprises performing a minima controlled recursive averaging of the local minima for each frequency bin with a corresponding local minima for each frequency bin in at least one preceding time period.

3. The method of claim 2, wherein minima controlled recursive averaging comprises Cohen's method.

4. The method of claim 1, further comprising:

sampling the audio signal and the accelerometer signal based on a sliding window;

wherein the candidate time period comprises the sliding window and the indication of the OSA event or CSA event is determined for each of a plurality of time periods.

5. The method of claim 4, wherein the sliding window is 61 seconds long.

6. The method of claim 1, further comprising:

applying, at the processor, a band-pass filter to the audio signal, the band-pass filter allowing frequencies between 200 Hz and 4000 Hz.

7. The method of claim 1, further comprising:

outputting, at a user interface device in communication with the processor, the indication of the OSA event or the CSA event.

8. The method of claim 1, further comprising:

determining, at the processor, a Hilbert envelope of the accelerometer signal;

normalizing, at the processor, the accelerometer signal using the Hilbert envelope; and wherein the determining, using the machine learning model at the processor, the indication of the OSA event or the CSA event is further based upon the normalized accelerometer signal.

9. The method of claim 8, further comprising:

determining, at the processor, a spectral peak of the accelerometer signal;

generating, at the processor, a breathing signal based on a frequency and a phase of the spectral peak; and wherein the determining, using the machine learning model at the processor, the indication of the OSA event or the CSA event is further based upon the breathing signal.

10. The method of claim 9, wherein the breathing signal comprises a sinusoidal breathing signal model.

11. The method of claim 1, wherein the determining, using the machine learning model at the processor, the indication of the OSA event or the CSA event further comprises:

determining, at the processor, a plurality of sleep feature values based on the audio signal and the accelerometer signal, the plurality of sleep feature values corresponding to a plurality of sleep features; and wherein the plurality of sleep features comprises at least one selected from the group of one or more audio features, and one or more accelerometer features.

12. The method of claim 11, wherein the one or more audio feature comprises an audio signal-to-noise ratio signal statistic and an audio signal MFC coefficient.

13. The method of claim 11, wherein the one or more accelerometer features comprise an accelerometer signal absolute rotation angle and pitch angle, and an accelerometer signal statistic.

14. The method of claim 11, further comprising:
receiving, at the processor, an oximeter signal; and
wherein the plurality of sleep features comprises at least
one oximeter feature, and the at least one oximeter
feature comprises an oximeter signal drop and an
oximeter signal slope.

15. The method of claim 1, wherein the determining the signal-to-noise ratio (SNR) signal for each frequency bin further comprises:
determining a total signal energy;
determining a total noise energy; and
determining the SNR based on a log of the ratio of the
total signal energy to the total noise ratio.

\* \* \* \* \*